(12) United States Patent
Koolman et al.

(10) Patent No.: US 9,169,253 B2
(45) Date of Patent: Oct. 27, 2015

(54) TRICYCLIC QUINOLINE AND QUINOXALINE DERIVATIVES

(71) Applicant: AbbVie Deutschland GmbH & Co. KG, Wiesbaden (DE)

(72) Inventors: Hannes Koolman, North Chicago, IL (US); Wilfried Braje, Ludwigshafen (DE); Helmut Mack, Ludwigshafen (DE); Andreas Haupt, Ludwigshafen (DE); Ana Lucia Relo, Ludwigshafen (DE); Karla Drescher, Ludwigshafen (DE); Margaretha Henrica Maria Bakker, Ludwigshafen (DE); Viktor Lakics, Ludwigshafen (DE); Carolin Hoft, Ludwigshafen (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 0 days.

(21) Appl. No.: 13/838,788

(22) Filed: Mar. 15, 2013

(65) Prior Publication Data
US 2014/0080814 A1    Mar. 20, 2014

Related U.S. Application Data

(60) Provisional application No. 61/701,514, filed on Sep. 14, 2012, provisional application No. 61/701,531, filed on Sep. 14, 2012.

(51) Int. Cl.
| C07D 471/06 | (2006.01) |
| C07D 487/02 | (2006.01) |
| C07D 221/20 | (2006.01) |
| C07D 221/18 | (2006.01) |
| C07D 487/06 | (2006.01) |

(52) U.S. Cl.
CPC ............ *C07D 471/06* (2013.01); *C07D 487/06* (2013.01)

(58) Field of Classification Search
CPC .. C07D 471/06; C07D 487/06; C07D 221/20; C07D 221/18
USPC .............. 514/219, 220; 540/556, 559; 546/18
See application file for complete search history.

(56) References Cited

U.S. PATENT DOCUMENTS

| 7,511,013 | B2 | 3/2009 | Molino et al. |
| 7,514,068 | B2 | 4/2009 | Tung |
| 7,521,421 | B2 | 4/2009 | Naicker et al. |
| 7,528,131 | B2 | 5/2009 | Persichetti et al. |
| 7,531,685 | B2 | 5/2009 | Czarnik |
| 7,534,814 | B2 | 5/2009 | Ascher et al. |
| 7,538,189 | B2 | 5/2009 | Naicker et al. |
| 2007/0225274 | A1 | 9/2007 | Jacobson |
| 2007/0225277 | A1 | 9/2007 | Rosenzweig-Lipson |
| 2008/0146583 | A1 | 6/2008 | McMurray et al. |
| 2009/0082471 | A1 | 3/2009 | Czarnik |
| 2009/0088416 | A1 | 4/2009 | Czarnik |
| 2009/0093422 | A1 | 4/2009 | Tung et al. |
| 2009/0105147 | A1 | 4/2009 | Masse |
| 2009/0105307 | A1 | 4/2009 | Galley et al. |
| 2009/0105338 | A1 | 4/2009 | Czarnik |
| 2009/0111840 | A1 | 4/2009 | Herold et al. |
| 2009/0118238 | A1 | 5/2009 | Czarnik |
| 2009/0131363 | A1 | 5/2009 | Harbeson |
| 2009/0131485 | A1 | 5/2009 | Liu et al. |
| 2009/0137457 | A1 | 5/2009 | Harbeson |

FOREIGN PATENT DOCUMENTS

| WO | WO-9507271 A1 | 3/1995 |
| WO | WO-9710223 A1 | 3/1997 |
| WO | WO-03091250 A1 | 11/2003 |
| WO | WO-2005099353 A2 | 10/2005 |
| WO | WO-2006008754 A1 | 1/2006 |

OTHER PUBLICATIONS

Sheridan, R.P. "The Most Common Chemical Replacement in drug-Like Compounds", J. Chem. Inf. Comput. Sci., 2002, vol. 42, pp. 103-108.*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Arjona A.A., et al., "Effect of a 5-Ht(2C) Serotonin Agonist, Dexnorfenfluramine, on Amyloid Precursor Protein Metabolism in Guinea Pigs," Brain Research, 2002, vol. 951 (1), pp. 135-140.
Barr A.M., et al., "The Selective Serotonin-2A Receptor Antagonist M100907 Reverses Behavioral Deficits in Dopamine Transporter Knockout Mice," Neuropsychopharmacology, 2004, vol. 29 (2), pp. 221-228.
Berge, S. M. et al., "Pharmaceutical Salts," Journal of Pharmaceutical Sciences, 1977, vol. 66 (1), pp. 1-19.
Beylot, M. et al., "In Vivo Studies of Intrahepatic Metabolic Pathways," Diabetes Metabolism, 1997, vol. 23 (3), pp. 251-257.
Blagojevic, N. et al., "Role of heavy water in Boron Neutron Capture Therapy," Topics in Dosimetry & Treatment Planning for Neutron Capture Therapy, 1994, pp. 125-134.
Blake, M. I. et al., "Studies With Deuterated Drugs," Journal of Pharmaceutical Sciences, 1975, vol. 64 (3), pp. 367-391.
Brennan P.E., et al., "Discovery of a Novel Azepine Series of Potent and Selective 5-Ht2C Agonists as Potential Treatments for Urinary Incontinence," Bioorganic * Medicinal Chemistry Letters, 2009, vol. 19 (17), pp. 4999-5003.
Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.

(Continued)

*Primary Examiner* — Kendra D Carter
(74) *Attorney, Agent, or Firm* — Lisa V. Mueller; Michael Best & Friedrich LLP

(57) ABSTRACT

The present invention relates to tricyclic quinoline and quinoxaline derivatives, to a pharmaceutical composition containing such compounds, to their use as modulators, especially agonists or partial agonists, of the 5-HT$_{2C}$ receptor, their use for preparing a medicament for the prevention or treatment of conditions and disorders which respond to the modulation of 5-HT$_{2C}$ receptor, and to a method for preventing or treating conditions and disorders which respond to the modulation of 5-HT$_{2C}$ receptor.

23 Claims, No Drawings

(56) References Cited

OTHER PUBLICATIONS

Brus R., et al., "Influence of 5,7-Dihydroxytryptamine (5,7-DHT) on the Antinociceptive Effect of Serotonine (5-HT) 5-HT 2C Receptor Agonist in Male and Female Rats," Medical Science & Monitoring, 1997, vol. 3 (5), pp. 654-656.

Bubar M.J., et al., "Prospects for Serotonin 5-HT2R Pharmacotherapy in Psychostimulant Abuse," Progress in Brain Research, 2008, vol. 172, pp. 319-346.

Butte N.F., et al., "Measurement of Milk Intake: Tracer-To-Infant Deuterium Dilution Method," British Journal of Nutrition, 1991, vol. 65, pp. 3-14.

Chou-Green J.M., et al., "Compulsive Behavior in the 5-HT2C Receptor Knockout Mouse," Physiology & Behavior, 2003, vol. 78 (4-5), pp. 641-649.

Chou-Green J.M., et al., "Repeated Stress in Young and Old 5-HT(2C) Receptor Knockout Mice," Physiology & Behavior, 2003, vol. 79 (2), pp. 217-226.

Coward W.A., et al., "New Method for Measuring Milk Intakes in Breast-Fed Babies," The Lancet, 1979, pp. 13-14.

Cryan J.F., et al., "Antidepressant-Like Behavioral Effects Mediated by 5-Hydroxytryptamine(2C) Receptors," The Journal of Pharmacology and Experimental Therapeutics, 2000, vol. 295 (3), pp. 1120-1126.

Czajka, D. M. et al., "Effect of Deuterium Oxide on the Reproductive Potential of Mice," Annals of the New York Academy of Sciences, 1960, vol. 84, pp. 770-779.

Czajka, D. M. et al., "Physiological Effects of Deuterium on Dogs," American Journal of Physiology, 1961, vol. 201 (2), pp. 357-362.

Davis K.L., et al., "Dopamine in Schizophrenia: A Review and Reconceptualization," The American Journal of Psychiatry, 1991, vol. 148 (11), pp. 1474-1486.

Dekeyne A., et al., "S32006, A Novel 5-HT2C Receptor Antagonist Displaying Broad-Based Antidepressant and Anxiolytic Properties in Rodent Models," Psychopharmacology, 2008, pp. 199 (4), pp. 549-568.

Denkewalter et al., Fortschritte der Arzneimittelforschung Progress in Drug Research Progres des receherches pharmaceutiques, 1996, 10, 224-285.

Di Giovanni G., et al., "Preferential Modulation of Mesolimbic vs. Nigrostriatal Dopaminergic Function by Serotonin(2C/2B) Receptor Agonists: A Combined in Vivo Electrophysiological and Microdialysis Study," Synapse, 2000, vol. 35 (1), pp. 53-61.

Di Matteo V., et al., "SB 242084, A Selective Serotonin2C Receptor Antagonist, Increases Dopaminergic Transmission in the Mesolimbic System," Neuropharmacology, 1999, vol. 38 (8), pp. 1195-1205.

Du Y., et al., "Editing of the Serotonin 2C Receptor Pre-mRNA: Effects of the Morris Water Maze," Gene, 2007, vol. 391 (1-2), pp. 186-197.

Dunlop J., et al., "Pharmacological Profile of the 5-HT2C Receptor Agonist Way-163909; Therapeutic Potential in Multiple Indications," CNS Drug Reviews, 2006, vol. 12 (3-4), pp. 167-177.

Dunlop J., et al., "Way-163909 [(7bR,10aR)-1,2,3,4,8,9,10,10a-Octahydro-7bHcyclopenta-[b][1,4]Diazepino[6,7,1Hi]Indole], A Novel 5-Hydroxytryptamine 2C Receptor-Selective Agonist with Anorectic Activity," The Journal of Pharmacology and Experimental Therapeutics, 2005, vol. 313 (2), pp. 862-869.

Esposito E., et al., "Role of central 5-HT2C receptor in the control of basal ganglia functions," The Basal Ganglia Pathophysiology, 2007, pp. 97-127.

Fletcher P.J., et al., "Serotonin Receptors as Potential Targets for Modulation of Nicotine Use and Dependence," Progress in Brain Research, 2008, vol. 172, pp. 361-383.

Foster, A. B. et al., "Deuterium Isotope Effects in the Metabolism of Drugs and Xenobiotics: Implications for Drug Design," Advances in Drug Research, 1985, vol. 14, pp. 2-36.

Frank M.G., et al., "Sleep and Sleep Homeostasis in Mice Lacking the 5-HT2C Receptor," Neuropsychopharmacology, 2002, vol. 27 (5), pp. 869-873.

Gatta F., et al., "Sur Quelques Derives De La Phenyl-1 Methyl-2 Dihydr0-4.5 6H-Pyrrolo (3.2.1-IJ)-Quinoleinone-6. 2. Synthese De Pyrido (3.2.1-JK)-Benzodiazepines-1.4//Derivatives of 1-Phenyl-2-Methyl-4.5-Dihydro-6H-Pyrrold-A3.2.1-IJU—Quinolin-6-0NE. 2. Synthesis of Pyrridoa3.2.1-Jku-1.4-Benzodiazepines," European Journal of Medicinal Chemistry, 1974, vol. 9 (2), pp. 133-135.

Greene T.W., et al., in: Protective Groups in Organic Synthesis, 3rd Edition, John Wiley and Sons, Inc., 1999, Preface, Table of Contents, Abbreviations.

International Search Report for Application No. PCT/EP2013/069036, mailed on Feb. 13, 2014, 8 pages.

Isaac M., "Serotonergic 5-HT2C Receptors as a Potential Therapeutic Target for the Design Antiepileptic Drugs," Current Topic in Medicinal Chemistry, 2005, vol. 5 (1), pp. 59-67.

Iwamoto K., et al., "Altered RNA Editing of Serotonin 2C Receptor in a Rat Model of Depression," Neuroscience Search, 2005, vol. 53 (1), pp. 69-76.

Iwamoto K., et al., "RNA Editing of Serotonin 2C Receptor in Human Postmortem Brains of Major Mental Disorders," Neuroscience Letters, 2003, vol. 346 (3), pp. 169-172.

Kao T., et al., "Role of the 5-HT2C Receptor in Improving Weight-Supported Stepping in Adult Rats Spinalized as Neonates," Brain Research, 2006, vol. 1112 (1), pp. 159-168.

Kato, S. et al., "Synthesis of Deuterated Mosapride Citrate," Journal of Labelled Compounds and Radiopharmaceuticals, 1995, vol. 36 (10), pp. 927-932.

Kaufman M.J., et al., "Cyclic Gmp Inhibits Phosphoinositide Turnover in Choroid Plexus: Evidence for Interactions between Second Messengers Concurrently Triggered by 5-HT2C Receptors," Neuroscience Letters, 1996, vol. 206 (2-3), pp. 153-156.

Kukla M.J., et al., "Synthesis and Anti-HIV-1 Activity of 4,5,6,7-Tetrahydro-5-Methylimidazo[4,5,1-jk][1,4]Benzodiazepin-2(1H)-one (TIBO) Derivatives. 2.," Journal of Medicinal Chemistry, 1991, vol. 34 (11), pp. 3187-3197.

Kushner D.J., et al., "Pharmacological Uses and Perspectives of Heavy Water and Deuterated Compounds.," Canadian Journal of Physiology and Pharmacology, 1999, vol. 77 (2), pp. 79-88.

Leone M., et al., "The Serotonergic System in Migraine," Journal of Headache Pain, 2001, vol. 2, pp. S43-S46.

Lidstrom P., et al., Microwave Assisted Organic Synthesis—A Review, Tetrahedron, 2001, vol. 57, pp. 9225-9283.

Lizondo, J. et al., "Linezolid: Oxazolidinone antibacterial," Drugs of the Future, 1996, vol. 21 (11), pp. 1116-1123.

Lopez-Gimenez J.F., et al., "Regional Distribution and Cellular Localization of 5-HT2C Receptor MRNA in Monkey Brain: Comparison with [3H]Mesulergine Binding Sites and Choline Acetyltransferase MRNA," Synapse, 2001, vol. 42 , pp. 2010-12-26.

MacLennan A.H., et al., "Neonatal Body Water Turnover: A Putative Index of Perinatal Morbidity," American Journal of Obstetrics & Gynecology , 1981, vol. 139 (8), pp. 948-952.

Mallesham, B. et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.

Marquis K.L., et al., "Way-163909 [(7bR,10aR)-1,2,3,4,8,9,10,10a-Octahydro-7bH-Cyclopenta-[b][1,4]Diazepino[6,7,1Hi]Indole]: A Novel 5-Hydroxytryptamine 2C Receptor-Selective Agonist with Preclinical Antipsychotic-Like Activity," The Journal of Pharmacology and Experimental Therapeutics, 2007, vol. 320 (1), pp. 486-496.

Mbaki Y., et al., "Investigation of the Role of 5-HT2 Receptor Subtypes in the Control of the Bladder and the Urethra in the Anaesthetized Female Rat," British Journal of Pharmacology, 2008, vol. 155 (3), pp. 343-356.

Motofei I.G., "A Dual Physiological Character for Sexual Function: The Role of Serotonergic Receptors," BJU International, 2008, vol. 101 (5), pp. 531-534.

Nakae A., et al., "Serotonin2C Receptor MRNA Editing in Neuropathic Pain Model," Neuroscience Research, 2008, vol. 60 (2), pp. 228-231.

Nakae A., et al., "The Role of RNA Editing of the Serotonin 2C Receptor in a Rat Model of Oro-Facial Neuropathic Pain," The European Journal of Neuroscience, 2008, vol. 27 (9), pp. 2373-2379.

(56) References Cited

OTHER PUBLICATIONS

Niswender C.M., et al., "RNA Editing of the Human Serotonin 5-HT2C Receptor. Alterations in Suicide and Implications for Serotonergic Pharmacotherapy," Neuropsychopharmacology, 2001, vol. 24 (5), pp. 478-491.

Nunes-De-Souza V., et al., "5-HT2 Receptor Activation in the Midbrain Periaqueductal Grey (PAG) Reduces Anxiety-Like Behaviour in Mice," Behavioural Brain Research, 2008, vol. 187 (1), pp. 72-79.

Obata H., et al., "Antiallodynic Effects of Intrathecally Administered 5-HT(2C) Receptor Agonists in Rats with Nerve Injury," Pain, 2004, vol. 108 (1-2), pp. 163-169.

Obata H., et al., "Possible Involvement of Spinal Noradrenergic Mechanisms in the Antiallodynic Effect of Intrathecally Administered 5-HT2C Receptor Agonists in the Rats with Peripheral Nerve Injury," European Journal of Pharmacology, 2007, vol. 567 (1-2), pp. 89-94.

Perreux L., et al., "A Tentative Rationalization of Microwave Effects in Organic Synthesis According to the Reaction Medium and Mechanistic Considerations," Tetrahedron, 2001, vol. 57, pp. 9199-9223.

Pompeiano M., et al., "Distribution of the Serotonin 5-HT2 Receptor Family mRNAs: Comparison between 5-HT2A and 5-HT2C Receptors," Molecular Brain Research, 1994, vol. 23 (1-2), pp. 163-178.

Pons G., et al., "Stable Isotopes Labeling of Drugs in Pediatric Clinical Pharmacology," Pediatrics, 1999, vol. 104 (3 Pt 2), pp. 633-639.

Prescott, Ed., Methods in Cell Biology, vol. XIV, Academic Press, New York, 1976, pp. 33.

Remington G., et al., "Atypical antipsychotics: are some more atypical than others", Psychopharmacology, 2000, vol. 148, pp. 3-15.

Rocha B.A., et al., "Enhanced Locomotor, Reinforcing, and Neurochemical Effects of Cocaine in Serotonin 5-Hydroxytryptamine 2C Receptor Mutant Mice," The Journal of Neuroscience, 2002, vol. 22 (22), pp. 10039-10045.

Rodewald L.E., et al., "Deuterium Oxide as a Tracer for Measurement of Compliance in Pediatric Clinical Drug Trials," Journal of Pediatrics, 1989, vol. 114 (5), 885-891.

Rosenzweig-Lipson S., et al., "5-HT2C Receptor Agonists as an Innovative Approach for Psychiatric Disorders," Drug News & Perspectives, 2007, vol. 20 (9), pp. 565-571.

Rosenzweig-Lipson S., et al., "Antidepressant-Like Effects of the Novel, Selective, 5-HT2C Receptor Agonist Way-163909 in Rodents," Psychopharmacology, 2007, vol. 192 (2), pp. 159-170.

Rosenzweig-Lipson S., et al., "Antiobesity-Like Effects of the 5-HT2C Receptor Agonist WAY-161503," Brain Research, 2006, vol. 1073-1074, pp. 240-251.

Schmauss C., "Serotonin 2C Receptors: Suicide, Serotonin, and Runaway RNA Editing," The Neuroscientist, 2003, vol. 9 (4), pp. 237-242.

Schwarcz H.P., "Use of Stable Isotopes to Determine Compliance," Controlled Clinical Trials, 1984, vol. 5 (Suppl 4), 573-575.

Sharif N.A., et al., "AL-34662: A Potent, Selective, and Efficacious Ocular Hypotensive Serotonin-2 Receptor Agonist," Journal of Ocular Pharmacology and Therapeutics, 2007, vol. 23 (1), pp. 1-13.

Shimada I., et al., "Synthesis and Structure-Activity Relationships of a Series of Benzazepine Derivatives as 5-HT2C Receptor Agonists," Bioorganic & Medicinal Chemistry, 2008, vol. 16 (6), pp. 3309-3320.

Siuciak J.A., et al., "CP-809,101, A Selective 5-HT2C Agonist, Shows Activity in Animal Models of Antipsychotic Activity," Neuropharmacology, 2007, vol. 52 (2), pp. 279-290.

Smith B.M., et al., "Discovery and Structure-Activity Relationship of (1R)-8-Chloro-2,3,4,5-Tetrahydro-1-Methyl-1H-3-Benzazepine (Lorcaserin), A Selective Serotonin 5-HT2C Receptor Agonist for the Treatment of Obesity," Journal of Medicinal Chemistry, 2008, vol. 51 (2), pp. 305-313.

Tecott L.H., et al., "Eating Disorder and Epilepsy in Mice Lacking 5-HT2C Serotonin Receptors," Nature, 1995, vol. 374 (6522), pp. 542-546.

Thomsen W.J., et al., "Lorcaserin, A Novel Selective Human 5-Hydroxytryptamine2C Agonist: In Vitro and In Vivo Pharmacological Characterization," The Journal of Pharmacology and Experimental Therapeutics, 2008, vol. 325 (2), pp. 577-587.

Thomson, J.F., "Physiological Effects of D2O in Mammals," Annals of the New York Academy of Sciences, 1960, vol. 84, pp. 736-744.

Thorslund K., et al., "Serotonergic Drugs—A Possible Role in the Treatment of Psoriasis", Drug News & Perspectives, 2007, vol. 20 (8), pp. 521-525.

Weinberger D.R., et al., "Prefrontal Function in Schizophrenia: Confounds and Controversies," Philosophical Transactions of the Royal Society of London, 1996, vol. 351 (1346), pp. 1495-1503.

Werry T.D., et al., "RNA Editing of the Serotonin 5HT2C Receptor and its Effects on Cell Signalling, Pharmacology and Brain Function," Pharmacology & Therapeutics, 2008, vol. 119 (1), pp. 7-23.

\* cited by examiner

TRICYCLIC QUINOLINE AND QUINOXALINE DERIVATIVES

RELATED APPLICATION INFORMATION

This application claims the benefit of U.S. Patent Application No. 61/701,514 filed on Sep. 14, 2012 and U.S. Patent Application No. 61/701,531 filed on Sep. 14, 2012, the contents of each of which are herein incorporated by reference.

FIELD OF THE INVENTION

The present invention relates to tricyclic quinoline and quinoxaline derivatives, to a pharmaceutical composition containing such compounds, to their use as modulators, especially agonists or partial agonists, of the 5-HT$_{2C}$ receptor, their use for preparing a medicament for the prevention or treatment of conditions and disorders which respond to the modulation of 5-HT$_{2C}$ receptor, to a method for preventing or treating conditions and disorders which respond to the modulation of 5-HT$_{2C}$ receptor, and processes for preparing such compounds and compositions.

BACKGROUND OF THE INVENTION

Diseases, disorders and conditions where 5-HT$_{2C}$ modulation is desired are for example depression, anxiety, schizophrenia, bipolar disorder, obsessive compulsive disorder, migraine, pain, epilepsy, substance abuse, eating disorders, obesity, diabetes, erectile dysfunction and others.

Serotonin (5-hydroxytryptamine, 5-HT), a monoamine neurotransmitter and local hormone, is formed by the hydroxylation and decarboxylation of tryptophan. The greatest concentration is found in the enterochromaffin cells of the gastrointestinal tract, the remainder being predominantly present in platelets and in the Central Nervous System (CNS). 5-HT is implicated in a vast array of physiological and pathophysiological pathways. In the periphery, it contracts a number of smooth muscles and induces endothelium-dependent vasodilation. In the CNS, it is believed to be involved in a wide range of functions, including the control of appetite, mood, anxiety, hallucinations, sleep, vomiting and pain perception.

Neurons that secrete 5-HT are termed serotonergic. The function of 5-HT is exerted upon its interaction with specific (serotonergic) neurons. Seven types of 5-HT receptors have been identified: 5-HT$_1$ (with subtypes 5-HT$_{1A}$, 5-HT$_{1B}$, 5-HT$_{1D}$, 5-HT$_{1E}$ and 5-HT$_{1F}$), 5-HT$_2$ (with subtypes 5-HT$_{2A}$, 5-HT$_{2B}$ and 5-HT$_{2C}$), 5-HT$_3$, 5-HT$_4$, 5-HT$_5$ (with subtypes 5-HT$_{5A}$ and 5-HT$_{5B}$), 5-HT$_6$ and 5-HT$_7$. Most of these receptors are coupled to G-proteins that affect the activities of adenylate cyclase or phospholipase Cγ.

Alterations in the activity of multiple neurotransmitter receptor systems (dopamine, serotonin, glutamate, GABA, acetylcholine) have been implicated in the manifestation of the symptoms of schizophrenia. The most widely accepted "Dopamine Hypothesis of Schizophrenia" in its simplest form states that the positive symptoms of this pathology relate to a functional hyperactivity of the mesolimbic dopaminergic system, while the negative and cognitive aspects can be traced to a functional hypoactivity of the mesocortical dopaminergic projections. Atypical antipsychotics block the mesolimbic dopaminergic neurotransmission, thereby controlling positive symptoms, with little or no effect on the nigrostriatal system, leading to less induction of extrapyramidal side effects (EPS).

Primary negative and cognitive symptoms of schizophrenia reflect a dysfunction of the frontal cortex ("hypofrontality"), which is thought to be induced by a decreased tone in the mesocortical dopaminergic projection field [Davis K L, Kahn R S, Ko G and Davidson M (1991). Dopamine in schizophrenia: a review and re-conceptualization. *Am J Psychiatry* 148: 1474-86. Weinberger D R and Berman K F (1996). Prefrontal function in schizophrenia: confounds and controversies. *Philos Trans R Soc Lond B Biol Sci* 351: 1495-503]. Agents that selectively enhance dopamine levels in the cortex have the potential to address the negative symptoms of this disorder. Atypical antipsychotics lack robust efficacy against negative and cognitive components of the schizophrenic syndrome.

The schizophrenic symptomatology is further complicated by the occurrence of drug-induced so-called secondary negative symptoms and cognitive impairment, which are difficult to distinguish from primary negative and cognitive symptoms [Remington G and Kapur S (2000). Atypical antipsychotics: are some more atypical than others? *Psychopharmacol* 148: 3-15]. The occurrence of secondary negative symptoms not only limits therapeutic efficacy but also, together with these side effects, negatively affects patient compliance.

It may thus be hypothesized that a novel mechanistic approach that blocks dopaminergic neurotransmission in the limbic system but does not affect the striatal and pituitary projection fields, and stimulates frontocortical projection fields, would provide an efficacious treatment for all parts of the schizophrenic pathology, including its positive, negative and cognitive symptoms. Moreover, a selective compound that is substantially free of the ancillary pharmacology that characterizes current agents would be expected to avoid a variety of off-target side effects that plague current treatments such as extrapyramidal side effects (EPS) and weight gain.

The 5-HT$_{2C}$ receptor, previously named 5-HT1C, is a G-protein-coupled receptor, which couples to multiple cellular effector systems including the phospholipase C, A and D pathways. It is found primarily in the brain and its distribution is particularly high in the plexus choroideus, where it is assumed to control cerebrospinal fluid production [Kaufman M J, Hirata F (1996) Cyclic GMP inhibits phosphoinositide turnover in choroid plexus: evidence for interactions between second messengers concurrently triggered by 5-HT$_{2C}$ receptors. *Neurosci Lett* 206:153-156]. Very high levels were also found in the retrosplenial, piriform and entorhinal cortex, anterior olfactory nucleus, lateral septal nucleus, subthalamic nucleus, amygdala, subiculum and ventral part of CA3, lateral habenula, substantia nigra pars compacta, several brainstem nuclei and the whole grey matter of the spinal cord [Pompeiano M, Palacios J M, Mengod G (1994). Distribution of the serotonin 5-HT2 receptor family mRNAs: comparison between 5-HT$_{2A}$ and 5-HT$_{2C}$ receptors. *Brain Res Mol Brain Res* 23:163-178]. A comparison of the distribution of 5-HT$_{2C}$ mRNA with that of 5-HT$_{2C}$ protein in monkey and human brains has revealed both pre- and postsynaptic localization [Lopez-Gimenez J F, Mengod G, Palacios J M, Vilaro M T (2001) Regional distribution and cellular localization of 5-HT$_{2C}$ receptor mRNA in monkey brain: comparison with [$^3$H]mesulergine binding sites and choline acetyltransferase mRNA. *Synapse* 42:12-26].

It is anticipated that modulation of the 5-HT$_{2C}$ receptor will improve disorders such as depression, anxiety, schizophrenia, cognitive deficits of schizophrenia, obsessive compulsive disorder, bipolar disorder, migraine, epilepsy, substance abuse, eating disorders, obesity, diabetes, sexual dysfunction/erectile dysfunction, sleep disorders, psoriasis, Parkinson's disease, pain conditions and disorders, and spinal cord injury, smoking cessation, ocular hypertension and Alzheimer's disease. Modulators of the 5-$HT_{2C}$ receptor are also shown to be useful in the modulation of bladder function, including the prevention or treatment of urinary incontinence.

There is an ongoing need for providing compounds having high affinity and selectivity for the 5-$HT_{2C}$ receptor. In particular the compounds should have low affinity to adrenergic receptors, such as the $\alpha_1$-adrenergic receptor, histamine receptors, such as the $H_1$-receptor, and dopaminergic receptors, such as the $D_2$-receptor, in order to avoid or reduce side effects associated with modulation of these receptors, such as postural hypotension, reflex tachycardia, potentiation of the antihypertensive effect of prazosin, terazosin, doxazosin and labetalol or dizziness associated with the blockade of the $\alpha_1$-adrenergic receptor, weight gain, sedation, drowsiness or potentiation of central depressant drugs associated with the blockade of the $H_1$-receptor, or extrapyramidal movement disorder, such as dystonia, parkinsonism, akathisia, tardive dyskinesia or rabbit syndrome, or endocrine effects, such as prolactin elevation (galactorrhea, gynecomastia, mentstrual changes, sexual dysfunction in males), associated with the blockade of the $D_2$-receptor.

The present invention provides compounds which have an affinity for the 5-$HT_{2C}$, thus allowing the treatment of disorders related to or affected by the 5-$HT_{2C}$ receptor.

SUMMARY OF THE INVENTION

The invention is directed to tricyclic qunioline and quinoxaline derivatives, compositions comprising such compounds, their use as modulators, especially agonists or partial agonists, of the 5-$HT_{2C}$ receptor, their use for preparing a medicament for the prevention or treatment of conditions and disorders which respond to the modulation of 5-$HT_{2C}$ receptor, to a method for preventing or treating conditions and disorders which respond to the modulation of 5-$HT_{2C}$ receptor, and processes for preparing such compounds and compositions.

In one aspect, the present invention relates to compounds of the formula (I):

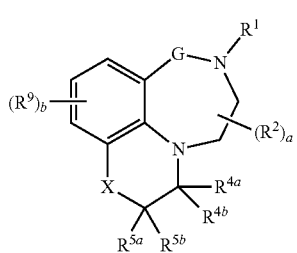

(I)

wherein
G is $(CR^{3a}R^{3b})_n$;
X is $NR^6$ or $CR^7R^8$;
$R^1$ is selected from the group consisting of hydrogen, cyano, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, —C(=O)$R^{10}$, phenyl, phenyl-$C_1$-$C_2$-alkyl and a 3-, 4-, 5-, 6-, 7- or 8-membered saturated, partially unsaturated or maximally unsaturated heterocyclic ring containing 1, 2, 3 or 4 heteroatoms or heteroatom groups independently selected from N, O, S, NO, SO and $SO_2$ and optionally also 1 or 2 C=O and/or C=S groups as ring members, where the cyclic moieties in the three last-mentioned radicals may be substituted with one or more substituents $R^{11}$;

each $R^2$ is independently selected from the group consisting of cyano, nitro, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, —$NR^{12a}R^{12b}$, —$CH_2NR^{12a}R^{12b}$, —$NR^{12a}C(O)R^{10}$, —C(=O)$R^{10}$, $SO_2NR^{12a}R^{12b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{11}$;

$R^{3a}$ and $R^{3b}$, independently of each other, are selected from the group consisting of hydrogen, cyano, nitro, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, —$NR^{12a}R^{12b}$, —$CH_2NR^{12a}R^{12b}$, —$NR^{12a}C(O)R^{10}$, —C(=O)$R^{10}$, $SO_2NR^{12a}R^{12b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{11}$;

$R^{4a}$ and $R^{4b}$, independently of each other, are selected from the group consisting of hydrogen, cyano, nitro, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl,
—$NR^{12a}R^{12b}$, —$CH_2NR^{12a}R^{12b}$, —$NR^{12a}C(O)R^{10}$, —C(=O)$R^{10}$, $SO_2NR^{12a}R^{12b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{11}$; or $R^{4a}$ and $R^{4b}$ form together a group =O or =S;

$R^{5a}$ and $R^{5b}$, independently of each other, are selected from the group consisting of hydrogen, deuterium, halogen, cyano, nitro, hydroxy, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, —$NR^{12a}R^{12b}$, —$CH_2NR^{12a}R^{12b}$,
—$NR^{12a}C(O)R^{10}$, —$C(=O)R^{10}$, $SO_2NR^{12a}R^{12b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{11}$; or $R^{5a}$ and $R^{5b}$, together with the carbon atom they are bound to, form a 3-, 4-, 5-, 6-, 7- or 8-membered saturated, partially unsaturated or maximally unsaturated ring, where the ring may contain 1, 2, 3 or 4 heteroatoms or heteroatom-containing groups selected from O, S, N, SO, $SO_2$, C=O and C=S as ring members, and where the ring may be substituted with one or more substituents $R^{11}$; or $R^{5a}$ and $R^6$, together with the atoms they are bound to, form a 3-, 4-, 5-, 6-, 7- or 8-membered saturated, partially unsaturated or maximally unsaturated heterocyclic ring, where the ring may further contain 1, 2, 3 or 4 heteroatoms or heteroatom-containing groups selected from O, S, N, SO, $SO_2$, C=O and C=S as ring members, and where the ring may be substituted with one or more substituents $R^{11}$; or $R^{5a}$ and $R^7$, together with the carbon atoms they are bound to, form a 3-, 4-, 5-, 6-, 7- or 8-membered saturated, partially unsaturated or maximally unsaturated ring, where the ring may contain 1, 2, 3 or 4 heteroatoms or heteroatom-containing groups selected from O, S, N, SO, $SO_2$, C=O and C=S as ring members, and where the ring may be substituted with one or more substituents $R^{11}$;

$R^6$ is selected from the group consisting of hydrogen, cyano, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_3$-$C_8$-cycloalkyl-$C_1$-$C_4$-alkyl, fluorinated $C_3$-$C_8$-cycloalkyl-$C_1$-$C_4$-alkyl, $C_1$-$C_6$-alkoxy, fluorinated $C_1$-$C_6$-alkoxy, —$C(=O)R^{10}$, —$SO_2R^{10}$, phenyl, phenyl-$C_1$-$C_2$-alkyl and a 3-, 4-, 5-, 6-, 7- or 8-membered saturated, partially unsaturated or maximally unsaturated heterocyclic ring containing 1, 2, 3 or 4 heteroatoms or heteroatom groups independently selected from N, O, S, NO, SO and $SO_2$ and optionally also 1 or 2 C=O and/or C=S groups as ring members, where the cyclic moieties in the three last-mentioned radicals may be substituted with one or more substituents $R^{11}$;

$R^7$ and $R^8$, independently of each other, are selected from the group consisting of deuterium, halogen, cyano, nitro, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, —$NR^{12a}R^{12b}$, —$CH_2NR^{12a}R^{12b}$,
—$NR^{12a}C(O)R^{10}$, —$C(=O)R^{10}$, $SO_2NR^{12a}R^{12b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{11}$; or $R^7$ and $R^8$, together with the carbon atom they are bound to, form a 3-, 4-, 5-, 6-, 7- or 8-membered saturated, partially unsaturated or maximally unsaturated ring, where the ring may contain 1, 2, 3 or 4 heteroatoms or heteroatom-containing groups selected from O, S, N, SO, $SO_2$, C=O and C=S as ring members, and where the ring may be substituted with one or more substituents $R^{11}$;

each $R^9$ is independently selected from the group consisting of halogen, cyano, nitro, hydroxy, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_3$-$C_8$-cycloalkenyl, fluorinated $C_3$-$C_8$-cycloalkenyl, $C_1$-$C_6$-alkoxy, fluorinated $C_1$-$C_6$-alkoxy, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, —$NR^{12a}R^{12b}$, —$CH_2NR^{12a}R^{12b}$,
—$NR^{12a}C(O)R^{10}$, —$C(=O)R^{10}$, $SO_2NR^{12a}R^{12b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{11}$; or two radicals $R^9$ bound on neighbouring carbon atoms, together with the carbon atoms they are bound to, form a 3-, 4-, 5-, 6-, 7- or 8-membered partially unsaturated or maximally unsaturated ring, where the ring may contain 1, 2, 3 or 4 heteroatoms or heteroatom-containing groups selected from O, S, N, SO, $SO_2$, C=O and C=S as ring members, and where the ring may be substituted with one or more substituents $R^{11}$;

each $R^{10}$ is independently selected from the group consisting of hydrogen, cyano, hydroxy, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, —$NR^{12a}R^{12b}$, —$CH_2NR^{12a}R^{12b}$, phenyl, phenyl-$C_1$-$C_2$-alkyl, phenoxy, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the five last-mentioned radicals may be substituted with one or more substituents $R^{11}$;

each $R^{11}$ is independently selected from the group consisting of halogen, cyano, nitro, hydroxy, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, —COOH, —$NR^{12a}R^{12b}$, —$CH_2NR^{12a}R^{12b}$, $C_1$-$C_6$-alkylcarbonyl, fluorinated $C_1$-$C_6$-alkylcarbonyl, $C_1$-$C_6$-alkoxycarbonyl, fluorinated $C_1$-$C_6$-alkoxycarbonyl, $SO_2NR^{12a}R^{12b}$, $C_1$-$C_6$-alkylcarbonyloxy and fluorinated $C_1$-$C_6$-alkylcarbonyloxy;

$R^{12a}$ and $R^{12b}$, independently of each other and independently of each occurrence, are selected from the group consisting of hydrogen, cyano, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkylcarbonyl, fluorinated $C_1$-$C_6$-alkylcarbonyl, $C_1$-$C_6$-alkoxycarbonyl, fluorinated $C_1$-$C_6$-alkoxycarbonyl, phenyl and benzyl, where the phenyl moieties in the two last-mentioned radicals may carry 1, 2 or 3 substituents selected from halogen, cyano nitro, $C_1$-$C_6$-alkyl, fluorinated $C_1$-$C_6$-alkyl, $C_1$-$C_6$-alkoxy and fluorinated $C_1$-$C_6$-alkoxy; or, if $R^{12a}$ and $R^{12b}$ are bound to the same nitrogen atom, together with this nitrogen atom may form a 3-, 4-, 5-, 6-, 7- or 8-membered saturated, partially unsaturated or maximally unsaturated heterocyclic ring, where the ring may further contain 1, 2, 3 or 4 heteroatoms or heteroatom-containing groups selected from O, S, N, SO, $SO_2$, C=O and C=S as ring members, and where the ring may be substituted with one or more substituents selected from halogen, cyano nitro, $C_1$-$C_6$-alkyl, fluorinated $C_1$-$C_6$-alkyl, $C_1$-$C_6$-alkoxy and fluorinated $C_1$-$C_6$-alkoxy;

a is 0, 1 or 2;
b is 0, 1, 2 or 3; and
n is 1 or 2;

and the N-oxides, tautomeric forms, stereoisomers and pharmaceutically acceptable salts thereof, and the compound of the general formula I, wherein at least one of the atoms has been replaced by its stable, non-radioactive isotope.

In another aspect, the invention relates to compounds of formula I

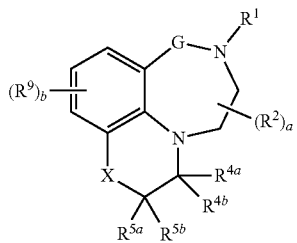

wherein
G is $(CR^{3a}R^{3b})_n$;
X is $NR^6$ or $CR^7R^8$;
$R^1$ is selected from the group consisting of hydrogen, cyano, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, —C(=O)$R^{10}$, phenyl, phenyl-$C_1$-$C_2$-alkyl and a 3-, 4-, 5-, 6-, 7- or 8-membered saturated, partially unsaturated or maximally unsaturated heterocyclic ring containing 1, 2, 3 or 4 heteroatoms or heteroatom groups independently selected from N, O, S, NO, SO and $SO_2$ and optionally also 1 or 2 C=O and/or C=S groups as ring members, where the cyclic moieties in the three last-mentioned radicals may be substituted with one or more substituents $R^{11}$;

each $R^2$ is independently selected from the group consisting of cyano, nitro, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, —$NR^{12a}R^{12b}$, —$CH_2NR^{12a}R^{12b}$, —$NR^{12a}C(O)R^{10}$, —C(=O)$R^{10}$, $SO_2NR^{12a}R^{12b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{11}$;

$R^{3a}$ and $R^{3b}$, independently of each other, are selected from the group consisting of hydrogen, cyano, nitro, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, —$NR^{12a}R^{12b}$, —$CH_2NR^{12a}R^{12b}$, —$NR^{12a}C(O)R^{10}$, —C(=O)$R^{10}$, $SO_2NR^{12a}R^{12b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{11}$;

$R^{4a}$ and $R^{4b}$, independently of each other, are selected from the group consisting of hydrogen, cyano, nitro, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, —$NR^{12a}R^{12b}$, —$CH_2NR^{12a}R^{12b}$, —$NR^{12a}C(O)R^1$, —C(=O)$R^{10}$, $SO_2NR^{12a}R^{12b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{11}$; or $R^{4a}$ and $R^{4b}$ form together a group =O or =S;

$R^{5a}$ and $R^{5b}$, independently of each other, are selected from the group consisting of hydrogen, deuterium, halogen, cyano, nitro, hydroxy, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, —$NR^{12a}R^{12b}$, —$CH_2NR^{12a}R^{12b}$, —$NR^{12a}C(O)R^{10}$, —C(=O)$R^{10}$, $SO_2NR^{12a}R^{12b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{11}$; or $R^{5a}$ and $R^{5b}$, together with the carbon atom they are bound to, form a 3-, 4-, 5-, 6-, 7- or 8-membered saturated, partially unsaturated or maximally unsaturated ring, where the ring may contain 1, 2, 3 or 4 heteroatoms or heteroatom-containing groups selected from O, S, N, SO, $SO_2$, C=O and C=S as ring members, and where the ring may be substituted with one or more substituents $R^{11}$; or $R^{5a}$ and $R^6$, together with the atoms they are bound to, form a 3-, 4-, 5-, 6-, 7- or 8-membered saturated, partially unsaturated or maximally unsaturated heterocyclic ring, where the ring may further contain 1, 2, 3 or 4 heteroatoms or heteroatom-containing groups selected from O, S, N, SO, $SO_2$, C=O and C=S as ring members, and where the ring may be substituted with one or more substituents $R^1$; or $R^{5a}$ and $R^7$, together with the carbon atoms they are bound to, form a 3-, 4-, 5-, 6-, 7- or 8-membered saturated, partially unsaturated or maximally unsaturated ring, where the ring may contain 1, 2, 3 or 4 heteroatoms or heteroatom-containing groups selected from O, S, N, SO, $SO_2$, C=O and C=S as ring members, and where the ring may be substituted with one or more substituents $R^{11}$;

$R^6$ is selected from the group consisting of hydrogen, cyano, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, —C(=O)$R^{10}$, —$SO_2R^{10}$, phenyl, phenyl-$C_1$-$C_2$-alkyl and a 3-, 4-, 5-, 6-, 7- or 8-membered saturated, partially unsaturated or maximally unsaturated heterocyclic ring containing 1, 2, 3 or 4 heteroatoms or heteroatom groups independently selected from N, O, S, NO, SO and $SO_2$ and optionally also 1 or 2 C=O and/or C=S groups as ring members, where the cyclic moieties in the three last-mentioned radicals may be substituted with one or more substituents $R^{11}$;

$R^7$ and $R^8$, independently of each other, are selected from the group consisting of deuterium, halogen, cyano, nitro, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, —$NR^{12a}R^{12b}$, —$CH_2NR^{12a}R^{12b}$, —$NR^{12a}C(O)R^{10}$, —C(=O)$R^{10}$, $SO_2NR^{12a}R^{12b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{11}$; or $R^7$ and $R^8$, together with the carbon atom they are bound to, form a 3-, 4-, 5-, 6-, 7- or 8-membered saturated, partially unsaturated or maximally unsaturated ring, where the ring may contain 1, 2, 3 or 4 heteroatoms or heteroatom-containing groups selected from O, S, N, SO, $SO_2$, C=O and C=S as ring members, and where the ring may be substituted with one or more substituents $R^{11}$;

each $R^9$ is independently selected from the group consisting of halogen, cyano, nitro, hydroxy, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_3$-$C_8$-cycloalkenyl, fluorinated $C_3$-$C_8$-cycloalkenyl, $C_1$-$C_6$-alkoxy, fluorinated $C_1$-$C_6$-alkoxy, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, —$NR^{12a}R^{12b}$, —$CH_2NR^{12a}R^{12b}$, —$NR^{12a}C(O)R^1$, —C(=O)$R^{10}$, $SO_2NR^{12a}R^{12b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{11}$; or two radicals $R^9$ bound on neighbouring carbon atoms, together with the carbon atoms they are bound to, form a 3-, 4-, 5-, 6-, 7- or 8-membered partially unsaturated or maximally unsaturated ring, where the ring may contain 1, 2, 3 or 4 heteroatoms or heteroatom-containing groups selected from O, S, N, SO, $SO_2$, C=O and C=S as ring members, and where the ring may be substituted with one or more substituents $R^{11}$;

each $R^{10}$ is independently selected from the group consisting of hydrogen, cyano, hydroxy, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, —$NR^{12a}R^{12b}$, —CH$_2$NR$^{12a}$R$^{12b}$, phenyl, phenyl-C$_1$-C$_2$-alkyl, phenoxy, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, SO$_2$, C=O and C=S as ring members, where the cyclic moieties in the five last-mentioned radicals may be substituted with one or more substituents R$^{11}$;

each R$^{11}$ is independently selected from the group consisting of halogen, cyano, nitro, hydroxy, C$_1$-C$_6$-alkyl, fluorinated C$_1$-C$_6$-alkyl, C$_1$-C$_6$-hydroxyalkyl, C$_2$-C$_6$-alkenyl, fluorinated C$_2$-C$_6$-alkenyl, C$_2$-C$_6$-alkynyl, fluorinated C$_2$-C$_6$-alkynyl, C$_3$-C$_8$-cycloalkyl, fluorinated C$_3$-C$_8$-cycloalkyl, C$_1$-C$_6$-alkoxy, fluorinated C$_1$-C$_6$-alkoxy, C$_1$-C$_6$-alkoxy-C$_1$-C$_4$-alkyl, C$_1$-C$_6$-hydroxyalkoxy, C$_1$-C$_6$-alkoxy-C$_1$-C$_4$-alkoxy, C$_1$-C$_6$-alkylthio, fluorinated C$_1$-C$_6$-alkylthio, C$_1$-C$_6$-alkylsulfinyl, fluorinated C$_1$-C$_6$-alkylsulfinyl, C$_1$-C$_6$-alkylsulfonyl, fluorinated C$_1$-C$_6$-alkylsulfonyl, —COOH, —NR$^{12a}$R$^{12b}$, —CH$_2$NR$^{12a}$R$^{12b}$, C$_1$-C$_6$-alkylcarbonyl, fluorinated C$_1$-C$_6$-alkylcarbonyl, C$_1$-C$_6$-alkoxycarbonyl, fluorinated C$_1$-C$_6$-alkoxycarbonyl, SO$_2$NR$^{12a}$R$^{12b}$, C$_1$-C$_6$-alkylcarbonyloxy and fluorinated C$_1$-C$_6$-alkylcarbonyloxy;

R$^{12a}$ and R$^{12b}$, independently of each other and independently of each occurrence, are selected from the group consisting of hydrogen, cyano, C$_1$-C$_6$-alkyl, fluorinated C$_1$-C$_6$-alkyl, C$_2$-C$_6$-alkenyl, fluorinated C$_2$-C$_6$-alkenyl, C$_2$-C$_6$-alkynyl, fluorinated C$_2$-C$_6$-alkynyl, C$_3$-C$_8$-cycloalkyl, fluorinated C$_3$-C$_8$-cycloalkyl, C$_1$-C$_6$-alkoxy, fluorinated C$_1$-C$_6$-alkoxy, C$_1$-C$_6$-alkylcarbonyl, fluorinated C$_1$-C$_6$-alkylcarbonyl, C$_1$-C$_6$-alkoxycarbonyl, fluorinated C$_1$-C$_6$-alkoxycarbonyl, phenyl and benzyl, where the phenyl moieties in the two last-mentioned radicals may carry 1, 2 or 3 substituents selected from halogen, cyano nitro, C$_1$-C$_6$-alkyl, fluorinated C$_1$-C$_6$-alkyl, C$_1$-C$_6$-alkoxy and fluorinated C$_1$-C$_6$-alkoxy; or, if R$^{12a}$ and R$^{12b}$ are bound to the same nitrogen atom, together with this nitrogen atom may form a 3-, 4-, 5-, 6-, 7- or 8-membered saturated, partially unsaturated or maximally unsaturated heterocyclic ring, where the ring may further contain 1, 2, 3 or 4 heteroatoms or heteroatom-containing groups selected from O, S, N, SO, SO$_2$, C=O and C=S as ring members, and where the ring may be substituted with one or more substituents selected from halogen, cyano nitro, C$_1$-C$_6$-alkyl, fluorinated C$_1$-C$_6$-alkyl, C$_1$-C$_6$-alkoxy and fluorinated C$_1$-C$_6$-alkoxy;

a is 0, 1 or 2;
b is 0, 1, 2 or 3; and
n is 1 or 2;

and the N-oxides, tautomeric forms, stereoisomers and pharmaceutically acceptable salts thereof, and the compound of the general formula I, wherein at least one of the atoms has been replaced by its stable, non-radioactive isotope.

In another aspect, the invention relates to a pharmaceutical composition comprising a therapeutically effective amount of at least one compound of formula I or an N-oxide, a tautomeric form, a stereoisomer or a pharmaceutically acceptable salt thereof, or comprising at least one compound as defined above or below wherein at least one of the atoms has been replaced by its stable, non-radioactive isotope, preferably wherein at least one hydrogen atom has been replaced by a deuterium atom, in combination with at least one pharmaceutically acceptable carrier and/or auxiliary substance.

In yet another aspect, the invention relates to a compound of formula I or an N-oxide, a tautomeric form, a stereoisomer or a pharmaceutically acceptable salt thereof for use as a medicament.

In yet another aspect, the invention relates to a compound of formula I or an N-oxide, a tautomeric form, a stereoisomer or a pharmaceutically acceptable salt thereof for the treatment of disorders which responds to the modulation of the 5-HT$_{2c}$ receptor.

In yet another aspect, the invention relates to the use of a compound of formula I or of an N-oxide, a tautomeric form, a stereoisomer or a pharmaceutically acceptable salt thereof for the manufacture of a medicament for the treatment of disorders which respond to the modulation of the 5-HT$_{2c}$ receptor.

In yet another aspect, the invention relates to the use of a compound of formula I or of an N-oxide, a tautomeric form, a stereoisomer or a pharmaceutically acceptable salt thereof for the manufacture of a medicament for the treatment of disorders selected from the group consisting of damage of the central nervous system, disorders of the central nervous system, eating disorders, ocular hypertension, cardiovascular disorders, gastrointestinal disorders and diabetes, and especially from the group consisting of bipolar disorder, depression, atypical depression, mood episodes, adjustment disorders, anxiety, panic disorders, post-traumatic syndrome, psychoses, schizophrenia, cognitive deficits of schizophrenia, memory loss, dementia of aging, Alzheimer's disease, behavioral disorders associated with dementia, social phobia, mental disorders in childhood, attention deficit hyperactivity disorder, organic mental disorders, autism, mutism, disruptive behavior disorder, impulse control disorder, borderline personality disorder, obsessive compulsive disorder, migraine and other conditions associated with cephalic pain or other pain, raised intracranial pressure, seizure disorders, epilepsy, substance use disorders, alcohol abuse, cocaine abuse, tobacco abuse, smoking cessation, sexual dysfunction/erectile dysfunction in males, sexual dysfunction in females, premenstrual syndrome, late luteal phase syndrome, chronic fatigue syndrome, sleep disorders, sleep apnoea, chronic fatigue syndrome, psoriasis, Parkinson's disease, spinal cord injury, trauma, stroke, pain, bladder dysfunction/urinary incontinence, encephalitis, meningitis, eating disorders, obesity, bulimia, weight loss, anorexia nervosa, ocular hypertension, cardiovascular disorders, gastrointestinal disorders, diabetes insipidus, diabetes mellitus, type I diabetes, type II diabetes, type III diabetes, diabetes secondary to pancreatic diseases, diabetes related to steroid use, diabetes complications, hyperglycemia and insulin resistance.

In yet another aspect, the invention relates to a method for treating disorders which respond to the modulation of the 5-HT$_{2c}$ receptor, which method comprises administering to a subject in need thereof at least one compound of formula I or an N-oxide, a tautomeric form, a stereoisomer or a pharmaceutically acceptable salt thereof.

In yet another aspect, the invention relates to a method for treating disorders selected from the group consisting of damage of the central nervous system, disorders of the central nervous system, eating disorders, ocular hypertension, cardiovascular disorders, gastrointestinal disorders and diabetes, and especially from the group consisting of bipolar disorder, depression, atypical depression, mood episodes, adjustment disorders, anxiety, panic disorders, post-traumatic syndrome, psychoses, schizophrenia, cognitive deficits of schizophrenia, memory loss, dementia of aging, Alzheimer's disease, behavioral disorders associated with dementia, social phobia, mental disorders in childhood, attention deficit hyperactivity disorder, organic mental disorders, autism, mutism, disruptive behavior disorder, impulse control disorder, borderline personality disorder, obsessive compulsive disorder, migraine and other conditions associated with cephalic pain or other pain, raised intracranial pressure, seizure disorders, epilepsy, substance use disorders, alcohol abuse, cocaine abuse, tobacco abuse, smoking cessation, sexual dysfunction/erectile dysfunction in males, sexual dysfunction in females, premenstrual syndrome, late luteal phase syndrome, chronic fatigue syndrome, sleep disorders, sleep apnoea, chronic fatigue syndrome, psoriasis, Parkinson's disease, spinal cord injury, trauma, stroke, pain, bladder dysfunction/urinary incontinence, encephalitis, meningitis, eating disorders, obesity, bulimia, weight loss, anorexia nervosa, ocular hypertension, cardiovascular disorders, gastrointestinal disorders, diabetes insipidus, diabetes mellitus, type I diabetes, type II diabetes, type III diabetes, diabetes secondary to pancreatic diseases, diabetes related to steroid use, diabetes complications, hyperglycemia and insulin resistance, which method comprises administering to a subject in need thereof at least one compound of formula I or an N-oxide, a tautomeric form, a stereoisomer or a pharmaceutically acceptable salt thereof.

DETAILED DESCRIPTION

The compounds of the formula I may exist in different spatial arrangements. For example, if the compounds possess one or more centers of asymmetry, polysubstituted rings or double bonds, or as different tautomers, the present invention contemplates the possible use of enantiomeric mixtures, in particular racemates, diastereomeric mixtures and tautomeric mixtures, such as the respective essentially pure enantiomers, diastereomers and tautomers of the compounds of formula I and/or their salts.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, acetic acid, trifluoroacetic acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 et seq., Birkhä user Verlag, Basel and Stuttgart, 1966.

The compounds of formula I may also be present in the form of tautomers. In one aspect, tautomery may be present in compounds I wherein $R^{4a}$ and $R^{4b}$ form together a group =O and $R^{5a}$ or $R^{5b}$ is H. For example, the compounds of formula I may have the following tautomeric formulae:

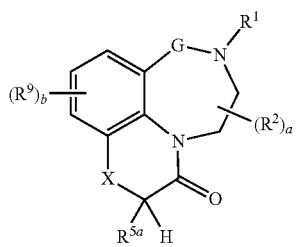

-continued

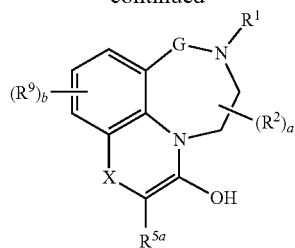

In another aspect, tautomery may be present in compounds I containing rings which have one or more C=O groups as ring members which are neighbored to a $CH_2$ group.

The organic moieties mentioned in the above definitions of the variables are, like the term halogen, collective terms for individual listings of the individual group members. The prefix $C_n$-$C_m$ indicates in each case the possible number of carbon atoms in the group.

The term "halogen" denotes in each case fluorine, bromine, chlorine or iodine. In one aspect, the halogen may be fluorine, chlorine or bromine.

The term "alkyl" as used herein and in the alkyl moieties of alkoxy, alkylthio, alkylsulfinyl, alkylsulfonyl, alkylcarbonyl, alkoxycarbonyl and the like refers to saturated straight-chain or branched hydrocarbon radicals having 1 to 2 ("$C_1$-$C_2$-alkyl"), 1 to 3 ("$C_1$-$C_3$-alkyl"), 1 to 4 ("$C_1$-$C_4$-alkyl") or 1 to 6 ("$C_1$-$C_6$-alkyl") carbon atoms. $C_1$-$C_2$-Alkyl is methyl or ethyl. $C_1$-$C_3$-Alkyl is additionally propyl and isopropyl. $C_1$-$C_4$-Alkyl is additionally butyl, 1-methylpropyl(sec-butyl), 2-methylpropyl(isobutyl) or 1,1-dimethylethyl(tert-butyl). $C_1$-$C_6$-Alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "fluorinated alkyl" as used herein refers to straight-chain or branched alkyl groups having 1 to 2 ("fluorinated $C_1$-$C_2$-alkyl"), 1 to 3 ("fluorinated $C_1$-$C_3$-alkyl"), 1 to 4 ("fluorinated $C_1$-$C_4$-alkyl") or 1 to 6 ("fluorinated $C_1$-$C_6$-alkyl") carbon atoms (as mentioned above), where some or all of the hydrogen atoms in these groups are replaced by fluorine atoms. Fluorinated $C_1$-$C_2$-alkyl is an alkyl group having 1 or 2 carbon atoms (as mentioned above), where at least one of the hydrogen atoms, e.g. 1, 2, 3, 4 or 5 hydrogen atoms in these groups are replaced by fluorine atoms, such as difluoromethyl, trifluoromethyl, 1-fluoroethyl, (R)-1-fluoroethyl, (S)-1-fluoroethyl, 2-fluoroethyl, 2,2-difluoroethyl, 2,2,2-trifluoroethyl, or pentafluoroethyl. Fluorinated $C_1$-$C_4$-alkyl is a straight-chain or branched alkyl group having 1 to 4 carbon atoms (as mentioned above), where at least one of the hydrogen atoms, e.g. 1, 2, 3, 4 or 5 hydrogen atoms in these groups are replaced by fluorine atoms. Examples are, apart those listed above for $C_1$-$C_2$-fluoroalkyl, 1-fluoropropyl, (R)-1-fluoropropyl, (S)-1-fluoropropyl, 2-fluoropropyl, (R)-2-fluoropropyl, (S)-2-fluoropropyl, 3-fluoropropyl, 1,1-difluoropropyl, 2,2-difluoropropyl, 1,2-difluoropropyl, 2,3-difluoropropyl, 1,3-difluoropropyl, 3,3-difluoropropyl, 1,1,2-trifluoropropyl, 1,2,2-trifluoropropyl, 1,2,3-trifluoropropyl, 2,2,3-trifluoropropyl, 3,3,3-trifluoropropyl, 1,1,1-trifluoroprop-2-yl, 2-fluoro-1-methylethyl, (R)-2-fluoro-1-methylethyl, (S)-2-fluoro-1-methylethyl, 2,2-difluoro-1-methylethyl, (R)-2,2-difluoro-1-methylethyl, (S)-2,2-difluoro-1-methylethyl, 1,2-difluoro-1-methylethyl, (R)-1,2-difluoro-1-methylethyl, (S)-1,2-difluoro-1-methylethyl, 2,2,2-trifluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-(trifluoromethyl)-2,2,2-trifluoroethyl, 1-(trifluoromethyl)-1,2,2,2-tetrafluoroethyl, 1-fluorobutyl, (R)-1-fluorobutyl, (S)-1-fluorobutyl, 2-fluorobutyl, (R)-2-fluorobutyl, (S)-2-fluorobutyl, 3-fluorobutyl, (R)-3-fluorobutyl, (S)-3-fluorobutyl, 4-fluorobutyl, 1,1-difluorobutyl, 2,2-difluorobutyl, 3,3-difluorobutyl, 4,4-difluorobutyl, 4,4,4-trifluorobutyl and the like. Fluorinated $C_1$-$C_6$-alkyl is a straight-chain or branched alkyl group having 1 to 6 carbon atoms (as mentioned above), where at least one of the hydrogen atoms, e.g. 1, 2, 3, 4 or 5 hydrogen atoms in these groups are replaced by fluorine atoms. Additionally examples include for $C_1$-$C_4$-fluoroalkyl, 1-fluoropentyl, (R)-1-fluoropentyl, (S)-1-fluoropentyl, 2-fluoropentyl, (R)-2-fluoropentyl, (S)-2-fluoropentyl, 3-fluoropentyl, (R)-3-fluoropentyl, (S)-3-fluoropentyl, 4-fluoropentyl, (R)-4-fluoropentyl, (S)-4-fluoropentyl, 5-fluoropentyl, (R)-5-fluoropentyl, (S)-5-fluoropentyl, 1-fluorohexyl, (R)-1-fluorohexyl, (S)-1-fluorohexyl, 2-fluorohexyl, (R)-2-fluorohexyl, (S)-2-fluorohexyl, 3-fluorohexyl, (R)-3-fluorohexyl, (S)-3-fluorohexyl, 4-fluorohexyl, (R)-4-fluorohexyl, (S)-4-fluorohexyl, 5-fluorohexyl, (R)-5-fluorohexyl, (S)-5-fluorohexyl, 6-fluorohexyl, (R)-6-fluorohexyl, (S)-6-fluorohexyl, and the like.

The term "alkenyl" as used herein refers to monounsaturated straight-chain or branched hydrocarbon radicals having 2 to 3 ("$C_2$-$C_3$-alkenyl"), 2 to 4 ("$C_2$-$C_4$-alkenyl") or 2 to 6 ("$C_2$-$C_6$-alkenyl") carbon atoms and a double bond in any position, such as $C_2$-$C_3$-alkenyl, such as ethenyl, 1-propenyl, 2-propenyl or 1-methylethenyl; $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; and $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like.

The term "fluorinated alkenyl" as used herein refers to unsaturated straight-chain or branched hydrocarbon radicals having 2 to 3 ("fluorinated $C_2$-$C_3$-alkenyl"), 2 to 4 ("fluorinated $C_2$-$C_4$-alkenyl") or 2 to 6 ("fluorinated $C_2$-$C_6$-alkenyl") carbon atoms and a double bond in any position (as mentioned above), where some or all of the hydrogen atoms in these groups are replaced by fluorine atoms, such as, fluorovinyl, fluoroallyl and the like.

The term "alkynyl" as used herein refers to straight-chain or branched hydrocarbon groups having 2 to 3 ("$C_2$-$C_3$-alkynyl"), 2 to 4 ("$C_2$-$C_4$-alkynyl") or 2 to 6 ("$C_2$-$C_6$-alkynyl") carbon atoms and one or two triple bonds in any position, such as $C_2$-$C_3$-alkynyl, such as ethynyl, 1-propynyl or 2-propynyl; $C_2$-$C_4$-alkynyl, such as ethynyl, 1-propynyl, 2-propynyl, 1-butynyl, 2-butynyl, 3-butynyl, 1-methyl-2-propynyl and the like, and $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like.

The term "fluorinated alkynyl" as used herein refers to unsaturated straight-chain or branched hydrocarbon radicals having 2 to 3 ("fluorinated $C_2$-$C_3$-alkynyl"), 3 to 4 ("fluorinated $C_3$-$C_4$-alkynyl") or 2 to 6 ("fluorinated $C_2$-$C_6$-alkynyl") carbon atoms and one or two triple bonds in any position (as mentioned above), where some or all of the hydrogen atoms in these groups are replaced by fluorine atoms.

The term "cycloalkyl" as used herein refers to mono- or bicyclic saturated hydrocarbon radicals having 3 to 8 ("$C_3$-$C_8$-cycloalkyl"), in particular 3 to 6 carbon atoms ("$C_3$-$C_6$-cycloalkyl") or 3 to 5 carbon atoms ("$C_3$-$C_5$-cycloalkyl") or 3 or 4 carbon atoms ("$C_3$-$C_4$-cycloalkyl"). In one aspect, $C_3$-$C_4$-cycloalkyl, $C_3$-$C_5$-cycloalkyl and $C_3$-$C_6$-cycloalkyl are monocyclic. Examples for $C_3$-$C_4$-cycloalkyl are cyclopropyl and cyclobutyl. Examples of monocyclic radicals having 3 to 5 carbon atoms are cyclopropyl, cyclobutyl and cyclopentyl. Examples of monocyclic radicals having 3 to 6 carbon atoms are cyclopropyl, cyclobutyl, cyclopentyl and cyclohexyl. Examples of monocyclic radicals having 3 to 8 carbon atoms are cyclopropyl, cyclobutyl, cyclopentyl, cyclohexyl, cycloheptyl and cyclooctyl. Examples of bicyclic radicals having 7 or 8 carbon atoms comprise bicyclo[2.2.1]heptyl, bicyclo[3.1.1]heptyl, bicyclo[2.2.2]octyl and bicyclo[3.2.1]octyl. In one aspect, the term cycloalkyl denotes a monocyclic saturated hydrocarbon radical.

The term "fluorinated cycloalkyl" as used herein refers to mono- or bicyclic saturated hydrocarbon groups having 3 to 8 ("$C_3$-$C_8$-halocycloalkyl") or preferably 3 to 6 ("$C_3$-$C_6$-halocycloalkyl") or 3 to 5 ("$C_3$-$C_5$-halocycloalkyl") carbon ring members (as mentioned above) in which some or all of the hydrogen atoms are replaced by fluorine atoms. Examples include 1-fluorocyclopropyl, 2-fluorocyclopropyl, (S)- and (R)-2,2-difluorocyclopropyl, 1,2-difluorocyclopropyl, 2,3-difluorocyclopropyl, pentafluorocyclopropyl, 1-fluorocyclobutyl, 2-fluorocyclobutyl, 3-fluorocyclobutyl, 2,2-difluorocyclobutyl, 3,3-difluorocyclobutyl, 1,2-difluorocyclobutyl, 1,3-difluorocyclobutyl, 2,3-difluorocyclobutyl, 2,4-difluorocyclobutyl, 1,2,2-trifluorocyclobutyl, 1-fluorocyclopentyl, 2-fluorocycloheptyl, 3-fluorocycloheptyl, 4-fluorocycloheptyl, 1,2-difluorocycloheptyl, 1,3-difluorocycloheptyl, 1,4-difluorocycloheptyl, 2,2-difluorocycloheptyl, 2,3-difluorocycloheptyl, 2,4-difluorocycloheptyl, 2,5-difluorocycloheptyl, 2,6-difluorocycloheptyl, 2,7-difluorocycloheptyl, 3,3-difluorocycloheptyl, 3,4-difluorocycloheptyl, 3,5-difluorocycloheptyl, 3,6-difluorocycloheptyl, 4,4-difluorocycloheptyl, 4,5-difluorocycloheptyl, and the like.

The term "cycloalkenyl" as used herein refers to monocyclic partially unsaturated, non-aromatic hydrocarbon radicals having 3 to 8 ("$C_3$-$C_8$-cycloalkenyl"), in particular 5 to 7 carbon atoms ("$C_5$-$C_7$-cycloalkenyl") or 5 or 6 carbon atoms ("$C_5$-$C_6$-cycloalkenyl") and one or more non-cumulative, preferably one, C—C double bonds in the ring. Examples for $C_5$-$C_6$-cycloalkenyl are cyclopent-1-en-1-yl, cyclopent-1-en-3-yl, cyclopent-1-en-4-yl, cyclopenta-1,3-dien-1-yl, cyclopenta-1,3-dien-2-yl, cyclopenta-1,3-dien-5-yl, cyclohex-1-en-1-yl, cyclohex-1-en-3-yl, cyclohex-1-en-4-yl, cyclohexa-1,3-dien-1-yl, cyclohexa-1,3-dien-2-yl, cyclohexa-1,3-dien-5-yl, cyclohexa-1,4-dien-1-yl and cyclohexa-1,4-dien-3-yl. Examples of $C_5$-$C_7$-cycloalkenyl are, apart those mentioned above, include for $C_5$-$C_6$-cycloalkenyl, cyclohept-1-en-1-yl, cyclohept-1-en-3-yl, cyclohept-1-en-4-yl, cyclohept-1-en-5-yl, cyclohepta-1,3-dien-1-yl, cyclohepta-1,3-dien-2-yl, cyclohepta-1,3-dien-5-yl, cyclohepta-1,3-dien-6-yl, cyclohepta-1,4-dien-1-yl, cyclohepta-1,4-dien-2-yl, cyclohepta-1,4-dien-3-yl and cyclohepta-1,4-dien-6-yl. Examples of $C_3$-$C_8$-cycloalkenyl are, apart those mentioned above for $C_5$-$C_6$-cycloalkenyl, cycloprop-1-en-1-yl, cycloprop-1-en-3-yl, cyclobut-1-en-1-yl, cyclobut-1-en-3-yl, cyclooct-1-en-1-yl, cyclooct-1-en-3-yl, cyclooct-1-en-4-yl, cyclooct-1-en-5-yl, cyclooctа-1,3-dien-1-yl, cycloocta-1,3-dien-2-yl, cycloocta-1,3-dien-5-yl, cycloocta-1,3-dien-6-yl, cycloocta-1,4-dien-1-yl, cycloocta-1,4-dien-2-yl, cycloocta-1,4-dien-3-yl, cycloocta-1,4-dien-6-yl, cycloocta-1,4-dien-7-yl, cycloocta-1,5-dien-1-yl, and cycloocta-1,5-dien-3-yl.

The term "fluorinated cycloalkenyl" as used herein refers to monocyclic partially unsaturated, non-aromatic hydrocarbon radicals having 3 to 8 ("fluorinated $C_3$-$C_8$-cycloalkenyl"), in particular 5 to 7 carbon atoms ("fluorinated $C_5$-$C_7$-cycloalkenyl") or 5 or 6 carbon atoms ("fluorinated $C_5$-$C_6$-cycloalkenyl") and one or more non-cumulative, preferably one, C—C double bonds in the ring and in which some or all of the hydrogen atoms are replaced by fluorine atoms.

The term "$C_1$-$C_2$-alkoxy" is a $C_1$-$C_2$-alkyl group, as defined above, attached via an oxygen atom. The term "$C_1$-$C_3$-alkoxy" is a $C_1$-$C_3$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. $C_1$-$C_2$-Alkoxy is methoxy or ethoxy. $C_1$-$C_3$-Alkoxy is additionally, for example, n-propoxy and 1-methylethoxy(isopropoxy). $C_1$-$C_4$-Alkoxy is additionally, for example, butoxy, 1-methylpropoxy(sec-butoxy), 2-methylpropoxy(isobutoxy) or 1,1-dimethylethoxy(tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof.

The term "fluorinated $C_1$-$C_2$-alkoxy" is a fluorinated $C_1$-$C_2$-alkyl group, as defined above, attached via an oxygen atom. The term "fluorinated $C_1$-$C_3$-alkoxy" is a fluorinated $C_1$-$C_3$-alkyl group, as defined above, attached via an oxygen atom. The term "fluorinated $C_1$-$C_6$-haloalkoxy" is a fluorinated $C_1$-$C_6$-alkyl group, as defined above, attached via an oxygen atom. Fluorinated $C_1$-$C_2$-alkoxy is, for example, $OCH_2F$, $OCHF_2$, $OCF_3$, 1-fluoroethoxy, (R)-1-fluoroethoxy, (S)-1-fluoroethoxy, 2-fluoroethoxy, 1,1-difluoroethoxy, 1,2-difluoroethoxy, 2,2-difluoroethoxy, 1,1,2-trifluoroethoxy, 1,2,2-trifluoroethoxy, 2,2,2-trifluoroethoxy, 1,1,2,2-tetrafluoroethoxy or $OC_2F_5$. Fluorinated $C_1$-$C_3$-alkoxy is additionally, for example, 1-fluoropropoxy, (R)-1-fluoropropoxy, (S)-1-fluoropropoxy, 2-fluoropropoxy, (R)-2-fluoropropoxy, (S)-2-fluoropropoxy, 3-fluoropropoxy, 1,1-difluoropropoxy, 2,2-difluoropropoxy, 2,3-difluoropropoxy, 3,3-difluoropropoxy, 3,3,3-trifluoropropoxy, (R)-2-fluoro-1-methylethoxy, (S)-2-fluoro-1-methylethoxy, (R)-2,2-difluoro-1-methylethoxy, (S)-2,2-difluoro-1-methylethoxy, (R)-1,2-difluoro-1-methylethoxy, (S)-1,2-difluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, $OCH_2$—$C_2F_5$, $OCF_2$—$C_2F_5$ or 1-($CH_2F$)-2-fluoroethoxy. Fluorinated $C_1$-$C_4$-alkoxy is additionally, for example, 1-fluorobutoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy or nonafluorobutoxy. Fluorinated $C_1$-$C_6$-alkoxy is additionally, for example, 5-fluoropentoxy, undecafluoropentoxy, 6-fluorohexoxy or tridecafluorohexoxy.

The term "$C_1$-$C_4$-alkoxy-$C_1$-$C_4$-alkyl" as used herein, refers to a straight-chain or branched alkyl group having 1 to 4 carbon atoms, as defined above, where one hydrogen atom is replaced by a $C_1$-$C_4$-alkoxy group, as defined above. The term "$C_1$-$C_6$-alkoxy-$C_1$-$C_4$-alkyl" as used herein, refers to a straight-chain or branched alkyl group having 1 to 4 carbon atoms, as defined above, where one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, 1-methoxyethyl, 1-ethoxyethyl, 1-propoxyethyl, 1-isopropoxyethyl, 1-n-butoxyethyl, 1-sec-butoxyethyl, 1-isobutoxyethyl, 1-tertbutoxyethyl, 2-methoxyethyl, 2-ethoxyethyl, 2-propoxyethyl, 2-isopropoxyethyl, 2-nbutoxyethyl, 2-sec-butoxyethyl, 2-isobutoxyethyl, 2-tert-butoxyethyl, 1-methoxypropyl, 1-ethoxypropyl, 1-propoxypropyl, 1-isopropoxypropyl, 1-n-butoxypropyl, 1-secbutoxypropyl, 1-isobutoxypropyl, 1-tert-butoxypropyl, 2-methoxypropyl, 2-ethoxypropyl, 2-propoxypropyl, 2-isopropoxypropyl, 2-n-butoxypropyl, 2-secbutoxypropyl, 2-isobutoxypropyl, 2-tert-butoxypropyl, 3-methoxypropyl, 3-ethoxypropyl, 3-propoxypropyl, 3-isopropoxypropyl, 3-n-butoxypropyl, 3-secbutoxypropyl, 3-isobutoxypropyl, 3-tert-butoxypropyl and the like.

The term "hydroxy-$C_1$-$C_4$-alkyl" as used herein, refers to a straight-chain or branched alkyl group having 1 to 4 carbon atoms, as defined above, where one hydrogen atom is replaced by a hydroxy group. The term "hydroxy-$C_1$-$C_6$-alkyl" as used herein, refers to a straight-chain or branched alkyl group having 1 to 6 carbon atoms, as defined above, where one hydrogen atom is replaced by a hydroxy group. Examples for hydroxy-$C_1$-$C_4$-alkyl include hydroxymethyl, 1-hydroxyethyl, 2-hydroxyethyl, 1-hydroxypropyl, 2-hydroxypropyl, 3-hydroxypropyl, 1-hydroxyprop-2-yl, 2-hydroxyprop-2-yl, 1-hydroxybutyl, 2-hydroxybutyl, 3-hydroxybutyl, 4-hydroxybutyl, 1-hydroxybut-2-yl, 2-hydroxybut-2-yl, 3-hydroxybut-2-yl, 4-hydroxybut-2-yl, hydroxytert-butyl and the like. Examples for hydroxy-$C_1$-$C_6$- alkyl are, apart those mentioned for hydroxy-$C_1$-$C_4$-alkyl, include, 1-hydroxypentyl, 2-hydroxypentyl, 3-hydroxypentyl, 4-hydroxypentyl, 5-hydroxypentyl, 1-hydroxyhexyl, 2-hydroxyhexyl, 3-hydroxyhexyl, 4-hydroxyhexyl, 5-hydroxyhexyl, 6-hydroxyhexyl and the like.

The term "hydroxy-$C_1$-$C_4$-alkoxy" as used herein, refers to a $C_1$-$C_4$-alkoxy group, as defined above, where one hydrogen atom is replaced by a hydroxy group. The term "hydroxy-$C_1$-$C_6$-alkoxy" as used herein, refers to a $C_1$-$C_6$-alkoxy group, as defined above, where one hydrogen atom is replaced by a hydroxy group. Examples for hydroxy-$C_1$-$C_4$-alkoxy include hydroxymethoxy, 1-hydroxyethoxy, 2-hydroxyethoxy, 1-hydroxypropoxy, 2-hydroxypropoxy, 3-hydroxypropoxy, 1-hydroxy-2-propoxy, 2-hydroxy-2-propoxy, 1-hydroxybutoxy, 2-hydroxybutoxy, 3-hydroxybutoxy, 4-hydroxybutoxy, 1-hydroxy-2-butoxy, 2-hydroxy-2-butoxy, 3-hydroxy-2-butoxy, 4-hydroxy-2-butoxy, hydroxy-tert-butoxy and the like. Examples for hydroxy-$C_1$-$C_6$-alkoxy include, apart those mentioned for hydroxy-$C_1$-$C_4$-alkoxy, 1-hydroxypentoxy, 2-hydroxypentoxy, 3-hydroxypentoxy, 4-hydroxypentoxy, 5-hydroxypentoxy, 1-hydroxyhexoxy, 2-hydroxyhexoxy, 3-hydroxyhexoxy, 4-hydroxyhexoxy, 5-hydroxyhexoxy, 6-hydroxyhexoxy and the like.

The term "$C_1$-$C_4$-alkoxy-$C_1$-$C_4$-alkoxy" as used herein, refers to a $C_1$-$C_4$-alkoxy group, as defined above, where one hydrogen atom is replaced by a $C_1$-$C_4$-alkoxy group, as defined above. The term "$C_1$-$C_6$-alkoxy-$C_1$-$C_4$-alkoxy" as used herein, refers to a $C_1$-$C_4$-alkoxy group, as defined above, where one hydrogen atom is replaced by a $C_1$-$C_4$-alkoxy group, as defined above. Examples are methoxymethoxy, ethoxymethoxy, propoxymethoxy, isopropoxymethoxy, butoxymethoxy, sec-butoxymethoxy, isobutoxymethoxy, tert-butoxymethoxy, 1-methoxyethoxy, 1-ethoxyethoxy, 1-propoxyethoxy, 1-isopropoxyethoxy, 1-butoxyethoxy, 1-sec-butoxyethoxy, 1-isobutoxyethoxy, 1-tert-butoxyethoxy, 2-methoxyethoxy, 2-ethoxyethoxy, 2-propoxyethoxy, 2-isopropoxyethoxy, 2-butoxyethoxy, 2-sec-butoxyethoxy, 2-isobutoxyethoxy, 2-tert-butoxyethoxy, 1-methoxypropoxy, 1-ethoxypropoxy, 1-propoxypropoxy, 1-isopropoxypropoxy, 1-butoxypropoxy, 1-sec-butoxypropoxy, 1-isobutoxypropoxy, 1-tert-butoxypropoxy, 2-methoxypropoxy, 2-ethoxypropoxy, 2-propoxypropoxy, 2-isopropoxypropoxy, 2-butoxypropoxy, 2-sec-butoxypropoxy, 2-isobutoxypropoxy, 2-tert-butoxypropoxy, 3-methoxypropoxy, 3-ethoxypropoxy, 3-propoxypropoxy, 3-isopropoxypropoxy, 3-butoxypropoxy, 3-sec-butoxypropoxy, 3-isobutoxypropoxy, 3-tert-butoxypropoxy and the like.

The term "$C_1$-$C_2$-alkylthio" is a $C_1$-$C_2$-alkyl group, as defined above, attached via a sulfur atom. The term "$C_1$-$C_3$-alkylthio" refers to a $C_1$-$C_3$-alkyl group, as defined above, attached via a sulfur atom. The term "$C_1$-$C_4$-alkylthio" is a $C_1$-$C_4$-alkyl group, as defined above, attached via a sulfur atom. The term "$C_1$-$C_6$-alkylthio" refers to a $C_1$-$C_6$-alkyl group, as defined above, attached via a sulfur atom. The term "$C_1$-$C_{10}$-alkylthio" refers to a $C_1$-$C_{10}$-alkyl group, as defined above, attached via a sulfur atom. $C_1$-$C_2$-Alkylthio is methylthio or ethylthio. $C_1$-$C_3$-Alkylthio is additionally, for example, npropylthio or 1-methylethylthio(isopropylthio). $C_1$-$C_4$-Alkylthio is additionally, for example, butylthio, 1-methylpropylthio(sec-butylthio), 2-methylpropylthio (isobutylthio) or 1,1-dimethylethylthio(tert-butylthio). $C_1$-$C_6$-Alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio.

The term "fluorinated $C_1$-$C_2$-alkylthio" refers to a fluorinated $C_1$-$C_2$-alkyl group, as defined above, attached via a sulfur atom. The term "fluorinated $C_1$-$C_3$-alkylthio" refers to a fluorinated $C_1$-$C_3$-alkyl group, as defined above, attached via a sulfur atom. The term "fluorinated $C_1$-$C_4$-alkylthio" refers to a fluorinated $C_1$-$C_4$-alkyl group, as defined above, attached via a sulfur atom. The term "fluorinated $C_1$-$C_6$-alkylthio" refers to a fluorinated $C_1$-$C_6$-alkyl group, as defined above, attached via a sulfur atom. Fluorinated $C_1$-$C_2$-alkylthio refers to, for example, $SCH_2F$, $SCHF_2$, $SCF_3$, 2-fluoroethylthio, 2,2-difluoroethylthio, 2,2,2-trifluoroethylthio, or $SC_2F_5$. Fluorinated $C_1$-$C_3$-alkylthio may additionally, for example, include 2-fluoropropylthio, 3-fluoropropylthio, 2,2-difluoropropylthio, 2,3-difluoropropylthio, 3,3,3-trifluoropropylthio, $SCH_2$—$C_2F_5$, $SCF_2$—$C_2F_5$ or 1-($CH_2F$)-2-fluoroethylthio. Fluorinated $C_1$-$C_4$-alkylthio may additionally, for example, include 4-fluorobutylthio or nonafluorobutylthio. Fluorinated $C_1$-$C_6$-alkylthio is additionally, for example, 5-fluoropentylthio, undecafluoropentylthio, 6-fluorohexylthio or dodecafluorohexylthio.

The term "$C_1$-$C_2$-alkylsulfinyl" refers to a $C_1$-$C_2$-alkyl group, as defined above, attached via a sulfinyl [S(O)] group. The term "$C_1$-$C_4$-alkylsulfinyl" is a $C_1$-$C_4$-alkyl group, as defined above, attached via a sulfinyl [S(O)] group. The term "$C_1$-$C_6$-alkylsulfinyl" is a $C_1$-$C_6$-alkyl group, as defined above, attached via a sulfinyl [S(O)] group. $C_1$-$C_2$-Alkylsulfinyl is methylsulfinyl or ethylsulfinyl. $C_1$-$C_4$-Alkylsulfinyl is additionally, for example, n-propylsulfinyl, 1-methylethylsulfinyl(isopropylsulfinyl), butylsulfinyl, 1-methylpropylsulfinyl(sec-butylsulfinyl), 2-methylpropylsulfinyl(isobutylsulfinyl) or 1,1-dimethylethylsulfinyl(tert-butylsulfinyl). $C_1$-$C_6$-Alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

The term "fluorinated $C_1$-$C_2$-alkylsulfinyl" refers to a fluorinated $C_1$-$C_2$-alkyl group, as defined above, attached via a sulfinyl [S(O)] group. The term "fluorinated $C_1$-$C_3$-alkylsulfinyl" refers to a fluorinated $C_1$-$C_3$-alkyl group, as defined above, attached via a sulfinyl [S(O)] group. The term "fluorinated $C_1$-$C_4$-alkylsulfinyl" refers to a fluorinated $C_1$-$C_4$-alkyl group, as defined above, attached via a sulfinyl [S(O)] group. The term "fluorinated $C_1$-$C_6$-alkylsulfinyl" refers to a fluorinated $C_1$-$C_6$-alkyl group, as defined above, attached via a sulfinyl [S(O)] group. Fluorinated $C_1$-$C_2$-alkylsulfinyl is, for example, $S(O)CH_2F$, $S(O)CHF_2$, $S(O)CF_3$, 2-fluoroethylsulfinyl, 2,2-difluoroethylsulfinyl, 2,2,2-trifluoroethylsulfinyl, or $S(O)C_2F_5$. Fluorinated $C_1$-$C_3$-alkylsulfinyl may additionally, for example, include 2-fluoropropylsulfinyl, 3-fluoropropylsulfinyl, 2,2-difluoropropylsulfinyl, 2,3-difluoropropylsulfinyl, 3,3,3-trifluoropropylsulfinyl, $S(O)CH_2$—$C_2F_5$, $S(O)CF_2$—$C_2F_5$ or 1-($CH_2F$)-2-fluoroethylsulfinyl. Fluorinated $C_1$-$C_4$-alkylsulfinyl may additionally, for example, include 4-fluorobutylsulfinyl or nonafluorobutylsulfinyl. Fluorinated $C_1$-$C_6$-alkylsulfinyl may additionally, for example, include 5-fluoropentylsulfinyl, undecafluoropentylsulfinyl, 6-fluorohexylsulfinyl or dodecafluorohexylsulfinyl.

The term "$C_1$-$C_2$-alkylsulfonyl" refers to a $C_1$-$C_2$-alkyl group, as defined above, attached via a sulfonyl $[S(O)_2]$ group. The term "$C_1$-$C_4$-alkylsulfonyl" refers to a $C_1$-$C_4$-alkyl group, as defined above, attached via a sulfonyl $[S(O)_2]$ group. The term "$C_1$-$C_6$-alkylsulfonyl" is a $C_1$-$C_6$-alkyl group, as defined above, attached via a sulfonyl $[S(O)_2]$ group. $C_1$-$C_2$-Alkylsulfonyl refers to a methylsulfonyl or ethylsulfonyl. $C_1$-$C_4$-Alkylsulfonyl is additionally, for example, n-propylsulfonyl, 1-methylethylsulfonyl(isopropylsulfonyl), butylsulfonyl, 1-methylpropylsulfonyl(sec-butylsulfonyl), 2-methylpropylsulfonyl(isobutylsulfonyl) or 1,1-dimethylethylsulfonyl(tertbutylsulfonyl). $C_1$-$C_6$-Alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl.

The term "fluorinated $C_1$-$C_2$-alkylsulfonyl" refers to a fluorinated $C_1$-$C_2$-alkyl group, as defined above, attached via a sulfonyl $[S(O)_2]$ group. The term "fluorinated $C_1$-$C_3$-alkylsulfonyl" refers to a fluorinated $C_1$-$C_3$-alkyl group, as defined above, attached via a sulfonyl $[S(O)_2]$ group. The term "fluorinated $C_1$-$C_4$-alkylsulfonyl" refers to a fluorinated $C_1$-$C_4$-alkyl group, as defined above, attached via a sulfonyl $[S(O)_2]$ group. The term "fluorinated $C_1$-$C_6$-alkylsulfonyl" refers to a fluorinated $C_1$-$C_6$-alkyl group, as defined above, attached via a sulfonyl $[S(O)_2]$ group. Fluorinated $C_1$-$C_2$-alkylsulfonyl is, for example, $S(O)_2CH_2F$, $S(O)_2CHF_2$, $S(O)_2CF_3$, 2-fluoroethylsulfonyl, 2,2-difluoroethylsulfonyl, 2,2,2-trifluoroethylsulfonyl, or $S(O)_2C_2F_5$. Fluorinated $C_1$-$C_3$-alkylsulfonyl is additionally, for example, 2-fluoropropylsulfonyl, 3-fluoropropylsulfonyl, 2,2-difluoropropylsulfonyl, 2,3-difluoropropylsulfonyl, 3,3,3-trifluoropropylsulfonyl, $S(O)_2CH_2$—$C_2F_5$, $S(O)_2CF_2$—$C_2F_5$ or 1-($CH_2F$)-2-fluoroethylsulfonyl. Fluorinated $C_1$-$C_4$-alkylsulfonyl is additionally, for example, 4-fluorobutylsulfonyl or nonafluorobutylsulfonyl. Fluorinated $C_1$-$C_6$-alkylsulfonyl is additionally, for example, 5-fluoropentylsulfonyl, undecafluoropentylsulfonyl, 6-fluorohexylsulfonyl or dodecafluorohexylsulfonyl.

$C_1$-$C_4$-Alkylcarbonyl refers to a straight-chain or branched alkyl group having from 1 to 4 carbon atoms), which is bound to the remainder of the molecule via a carbonyl group (CO), such as in acetyl, propionyl, isopropylcarbonyl, butylcarbonyl, secbutylcarbonyl, isobutylcarbonyl, and tert-butylcarbonyl. $C_1$-$C_6$-Alkylcarbonyl is a straight-chain or branched alkyl group having from 1 to 6 carbon atoms, which is bound to the remainder of the molecule via a carbonyl group (CO). Examples include, apart those listed above for $C_1$-$C_4$-alkylcarbonylpentylcarbonyl, hexylcarbonyl and the constitutional isomers thereof.

Fluorinated $C_1$-$C_4$-alkylcarbonyl refers to a straight-chain or branched fluorinated alkyl group having from 1 to 4 carbon atoms as defined above, which is bound to the remainder of the molecule via a carbonyl group (CO). Fluorinated $C_1$-$C_6$-alkylcarbonyl is a straight-chain or branched fluorinated alkyl group having from 1 to 6 carbon atoms as defined above, which is bound to the remainder of the molecule via a carbonyl group (CO). Examples include trifluoromethylcarbonyl, 2,2,2-trifluoroethylcarbonyl and the like.

$C_1$-$C_6$-Alkoxycarbonyl refers to a straight-chain or branched alkoxy group having from 1 to 6, especially 1 to 4 carbon atoms (=$C_1$-$C_4$-alkoxycarbonyl), in particular 1 to 3 carbon atoms (=$C_1$-$C_3$-alkoxycarbonyl), which is bound to the remainder of the molecule via a carbonyl group (CO), such as in methoxycarbonyl, ethoxycarbonyl, propyloxycarbonyl, and isopropyloxycarbonyl.

Fluorinated $C_1$-$C_6$-alkoxycarbonyl refers to a straight-chain or branched fluorinated alkoxy group having from 1 to 6, especially 1 to 4 carbon atoms (=fluorinated $C_1$-$C_4$-alkoxycarbonyl), in particular 1 to 3 carbon atoms (=fluorinated $C_1$-$C_3$-alkoxycarbonyl) as defined above, which is bound to the remainder of the molecule via a carbonyl group (CO). Examples include trifluoromethoxycarbonyl, 2,2,2-trifluoroethoxycarbonyl and the like.

$C_1$-$C_4$-Alkylcarbonyloxy refers to a straight-chain or branched alkyl group having from 1 to 4 carbon atoms, which is bound to the remainder of the molecule via a carbonyloxy group [C(O)—O—], such as in acet(yl)oxy, propionyloxy, isopropylcarbonyloxy, butylcarbonyloxy, sec-butylcarbonyloxy, isobutylcarbonyloxy, and tert-butylcarbonyloxy. $C_1$-$C_6$-Alkylcarbonyloxy is a straight-chain or branched alkyl group having from 1 to 6 carbon atoms, which is bound to the remainder of the molecule via a carbonyloxy group [C(O—O—]. Examples include, apart those listed above for $C_1$-$C_4$-alkylcarbonyloxy, pentylcarbonyloxy, hexylcarbonyloxy and the constitutional isomers thereof.

Fluorinated $C_1$-$C_4$-alkylcarbonyloxy refers to a straight-chain or branched fluorinated alkyl group having from 1 to 4 carbon atoms as defined above, which is bound to the remainder of the molecule via a carbonyloxy group [C(O)—O—]. Fluorinated $C_1$-$C_6$-alkylcarbonyloxy is a straight-chain or branched fluorinated alkyl group having from 1 to 6 carbon atoms as defined above, which is bound to the remainder of the molecule via a carbonyloxy group [C(O)—O—]. Examples include trifluoromethylcarbonyloxy, 2,2,2-trifluoroethylcarbonyloxy and the like.

Phenyl-$C_1$-$C_2$-alkyl is a phenyl group bound to the remainder of the molecule via a $C_1$-$C_2$-alkyl group. Examples are benzyl, 1-phenylethyl and 2-phenylethyl(phenethyl).

The term "3-, 4-, 5-, 6-, 7- or 8-membered saturated, partially unsaturated or maximally unsaturated heterocyclic ring containing 1, 2, 3 or 4 heteroatoms or heteroatom groups independently selected from N, O, S, NO, SO and $SO_2$ and optionally also 1 or 2 C=O and/or C=S groups as ring members" denotes a 3-, 4-, 5-, 6-, 7- or 8-membered, preferably a 3-, 4-, 5-, 6- or 7-membered saturated, partially unsaturated or maximum unsaturated heteromonocyclic ring containing 1, 2, 3 or 4 (preferably 1, 2 or 3) heteroatoms or heteroatom groups selected from N, O, S, SO and $SO_2$ and optionally also 1 or 2 C=O and/or C=S groups as ring members.

Unsaturated rings contain at least one C—C and/or C—N and/or N—N double bond(s). Maximally unsaturated rings contain as many conjugated C—C and/or C—N and/or N—N double bonds as allowed by the ring size. Maximally unsaturated 5- or 6-membered heterocyclic rings are aromatic. 7- and 8-membered rings cannot be aromatic. They are homoaromatic (7-membered ring, 3 double bonds) or have 4 double bonds (8-membered ring). Partially unsaturated rings contain less than the maximum number of C—C and/or C—N and/or N—N double bond(s) allowed by the ring size. The heterocyclic ring may be attached to the remainder of the molecule via a carbon ring member or via a nitrogen ring member. As a matter of course, the heterocyclic ring contains at least one carbon ring atom. If the ring contains more than one O ring atom, these are not adjacent.

Examples of a 3-, 4-, 5-, 6- or 7-membered saturated heterocyclic ring include: Oxiranyl, thiiranyl, aziridinyl, oxetanyl, thietanyl, azetidinyl, tetrahydrofuran-2-yl, tetrahydrofuran-3-yl, tetrahydrofuran-2-on-3-yl, tetrahydrofuran-2-on-4-yl, tetrahydrofuran-2-on-5-yl, tetrahydrofuran-2-thion-3-yl, tetrahydrofuran-2-thion-4-yl, tetrahydrofuran-2-thion-5-yl, tetrahydrothien-2-yl, tetrahydrothien-3-yl, tetrahydrothien-2-on-3-yl, tetrahydrothien-2-on-4-yl, tetrahydrothien-2-on-5-yl, tetrahydrothien-2-thion-3-yl, tetrahydrothien-2-thion-4-yl, tetrahydrothien-2-thion-5-yl, pyrrolidin-1-yl, pyrrolidine-2-on-1-yl, pyrrolidine-2,5-dion-1-yl, pyrrolidine-2-thion-1-yl, pyrrolidin-2-yl, pyrrolidin-3-yl, pyrrolidine-2-on-3-yl, pyrrolidine-2-on-4-yl, pyrrolidine-2-on-5-yl, pyrrolidine-2,5-dion-3-yl, pyrrolidine-2-thion-3-yl, pyrrolidine-2-thion-4-yl, pyrrolidine-2-thion-5-yl, pyrazolidin-1-yl, pyrazolidin-3-yl, pyrazolidin-4-yl, pyrazolidin-5-yl, imidazolidin-1-yl, imidazolidin-2-on-1-yl, imidazolidin-2-thion-1-yl, imidazolidin-2-yl, imidazolidin-4-yl, imidazolidin-2-on-4-yl, imidazolidin-2-thion-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolidin-5-yl, isothiazolidin-2-yl, isothiazolidin-3-yl, isothiazolidin-4-yl, isothiazolidin-5-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2-tetrahydropyranyl, 4-tetrahydropyranyl, 1,3-dioxan-5-yl, 1,4-dioxan-2-yl, piperidin-1-yl, piperidin-2-on-1-yl, piperidin-2,5-dion-1-yl, piperidine-2-thion-1-yl, piperidin-2-yl, piperidin-3-yl, piperidin-2-on-3-yl, piperidin-2,5-dion-3-yl, piperidin-2-thion-3-yl, piperidin-4-yl, hexahydropyridazin-3-yl, hexahydropyridazin-4-yl, hexahydropyrimidin-2-yl, hexahydropyrimidin-4-yl, hexahydropyrimidin-5-yl, piperazin-1-yl, piperazin-2-yl, 1,3,5-hexahydrotriazin-1-yl, 1,3,5-hexahydrotriazin-2-yl and 1,2,4-hexahydrotriazin-3-yl, morpholin-2-yl, morpholin-3-yl, morpholin-4-yl, thiomorpholin-2-yl, thiomorpholin-3-yl, thiomorpholin-4-yl, 1-oxothiomorpholin-2-yl, 1-oxothiomorpholin-3-yl, 1-oxothiomorpholin-4-yl, 1,1-dioxothiomorpholin-2-yl, 1,1-dioxothiomorpholin-3-yl, 1,1-dioxothiomorpholin-4-yl, azepan-1-, -2-, -3- or -4-yl, oxepan-2-, -3-, -4- or -5-yl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of a 3-, 4-, 5-, 6-, 7- or 8-membered saturated heterocyclic ring further include oxocane, thiocane, azocane, [1,3]diazocane, [1,4]diazocane, [1,5]diazocane, [1,5]oxazocane and the like.

Examples of a 3-, 4-, 5-, 6- or 7-membered partially unsaturated heterocyclic ring include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-4-yl, 4-isothiazolin-4-yl, 2-isothiazolin-3-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

Examples of a 3-, 4-, 5-, 6-, 7- or 8-membered partially unsaturated heterocyclic ring further include 1,2,3,4,5,6-hexahydroazocine, 2,3,4,5,6,7-hexahydroazocine, 1,2,3,4,5,8-hexahydroazocine, 1,2,3,4,7,8-hexahydroazocine, 1,2,3,4,5,6-hexahydro-[1,5]diazocine, 1,2,3,4,7,8-hexahydro-[1,5]diazocine and the like.

Examples of a 3-, 4-, 5-, 6- or 7-membered maximally unsaturated (including aromatic) heterocyclic ring include 5- or 6-membered heteroaromatic rings, such as 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl and 2-pyrazinyl, and also homoaromatic radicals, such as 1H-azepine, 1H-[1,3]-diazepine and 1H-[1,4]-diazepine.

Examples of a 3-, 4-, 5-, 6-, 7- or 8-membered maximally unsaturated heterocyclic ring further include [1,3]diazocine, [1,5]diazocine and [1,5]diazocine.

A 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members is either saturated, partially unsaturated and carbocyclic (if it contains only C=O and/or C=S as heteroatom group and no further heteroatoms or heteroatom groups) or saturated, partially unsaturated or maximally unsaturated heterocyclic. Examples are, in addition to the heterocyclic rings mentioned above, carbocyclic rings, such as cyclopropanonyl, cyclobutanonyl, cyclopentanonyl, cyclohexanonyl, cyclohexandionyl, cycloheptanonyl, cyclooctanonyl, cyclopropanthionyl, cyclobutanthionyl, cyclopentanthionyl, cyclohexanthionyl, cyclohexandithionyl, cycloheptanthionyl, cyclooctanthionyl, cyclopropenonyl, cyclopentenonyl, cyclohexenonyl and the like.

The remarks made above and in the following with respect to preferred aspects of the invention, e.g. to preferred meanings of the variables $R^1$, $R^2$, $R^{3a}$, $R^{3b}$, $R^{4a}$, $R^{4b}$, $R^{5a}$, $R^{5b}$, $R^6$, $R^7$, $R^8$, $R^9$, a, b and n of compounds I, to preferred compounds I and to preferred embodiments of the method or the use according to the invention, apply in each case on their own or in particular to combinations thereof.

In a preferred embodiment, $R^1$ is selected from hydrogen, cyano, $C_1$-$C_6$-alkyl, fluorinated $C_1$-$C_6$-alkyl, —C(=O)$R^{10}$, phenyl and benzyl, where the phenyl moiety in the two last-mentioned radicals may carry 1, 2 or 3 radicals $R^{11}$, where $R^{10}$ and $R^{11}$ have one of the general meanings given above, or, in particular, one of the preferred meanings given below.

In the above group —C(=O)$R^{10}$ as a meaning for $R^1$, $R^{10}$ is preferably selected from $C_1$-$C_4$-alkyl and $C_1$-$C_4$-alkoxy and more preferably from $C_1$-$C_2$-alkyl and tert-butoxy.

More preferably, $R^1$ is selected from hydrogen and $C_1$-$C_6$-alkyl, in particular from hydrogen and methyl, and is specifically hydrogen.

In a preferred embodiment, $R^2$ is selected from cyano, nitro, $C_1$-$C_6$-alkyl, fluorinated $C_1$-$C_6$-alkyl, $C_1$-$C_6$-alkoxy and fluorinated $C_1$-$C_6$-alkoxy, more preferably from $C_1$-$C_6$-alkyl, in particular from methyl, ethyl, propyl and isopropyl, and is specifically methyl.

In a preferred embodiment, $R^{3a}$ and $R^{3b}$, independently of each other, are selected from hydrogen, cyano, nitro, $C_1$-$C_6$-alkyl, fluorinated $C_1$-$C_6$-alkyl, $C_1$-$C_6$-alkoxy and fluorinated $C_1$-$C_6$-alkoxy. More preferably, $R^{3a}$ is selected from hydrogen, cyano, nitro, $C_1$-$C_6$-alkyl, fluorinated $C_1$-$C_6$-alkyl, $C_1$-$C_6$-alkoxy and fluorinated $C_1$-$C_6$-alkoxy, and $R^{3b}$ is hydrogen. Even more preferably, $R^{3a}$ is selected from hydrogen and methyl and $R^{3b}$ is hydrogen. In particular, both $R^{3a}$ and $R^{3b}$ are hydrogen.

In a preferred embodiment, $R^{4a}$ and $R^{4b}$, independently of each other, are selected from hydrogen, $C_1$-$C_6$-alkyl and fluorinated $C_1$-$C_6$-alkyl or form together a group =O. More preferably, they are hydrogen or form together a group =O. In particular, both $R^{4a}$ and $R^{4b}$ are hydrogen.

In a preferred embodiment, $R^{5a}$ is selected from hydrogen, cyano, nitro, hydroxy, $C_1$-$C_6$-alkyl, fluorinated $C_1$-$C_6$-alkyl, $C_1$-$C_6$-alkoxy and fluorinated $C_1$-$C_6$-alkoxy; and in case that X is $CR^7R^8$ is further selected from halogen; or $R^{5a}$ and $R^6$, together with the atoms they are bound to, form a 3-, 4-, 5-, 6- or 7-membered saturated, partially unsaturated or maximally unsaturated heterocyclic ring, where the ring may further contain 1, 2, 3 or 4 heteroatoms or heteroatom-containing groups selected from O, S, N, SO, $SO_2$, C=O and C=S as ring members, and where the ring may be substituted with one or more substituents $R^{11}$; or $R^{5a}$ and $R^7$, together with the carbon atoms they are bound to, form a 3-, 4-, 5-, 6- or 7-membered saturated, partially unsaturated or maximally unsaturated ring, where the ring may contain 1, 2, 3 or 4 heteroatoms or heteroatom-containing groups selected from O, S, N, SO, $SO_2$, C=O and C=S as ring members, and where the ring may be substituted with one or more substituents $R^{11}$; and $R^{5b}$ is selected from hydrogen and deuterium and is preferably hydrogen;

where $R^{11}$ has one of the general meanings given above, or, in particular, one of the preferred meanings given below.

More preferably, $R^{5a}$ is selected from hydrogen, $C_1$-$C_6$-alkyl and fluorinated $C_1$-$C_6$-alkyl; and in case that X is $CR^7R^8$ is further selected from halogen; and is preferably selected from hydrogen and methyl, or $R^{5a}$ and $R^6$ form together a group $(CH_2)_r$, where r is 2, 3, 4 or 5, preferably 2, 3 or 4; or $R^{5a}$ and $R^7$ form together a group $(CH_2)_s$, where s is 2, 3, 4 or 5, preferably 2, 3 or 4; and $R^{5b}$ is selected from hydrogen and deuterium and is preferably hydrogen.

In an alternatively preferred embodiment, $R^{5a}$ and $R^{5b}$, together with the carbon atom they are bound to, form a 3-, 4-, 5-, 6-, 7- or 8-membered saturated, partially unsaturated or maximally unsaturated ring, where the ring may contain 1, 2, 3 or 4 heteroatoms or heteroatom-containing groups selected from O, S, N, SO, $SO_2$, C=O and C=S as ring members, and where the ring may be substituted with one or more substituents $R^{11}$; and form in particular a 5- or 6-membered saturated or partially unsaturated carbocyclic ring, and where the ring may be substituted with one or more substituents $R^{11}$.

In one embodiment, X is $NR^6$, where $R^6$ has one of the general meanings given above, or, in particular, one of the preferred meanings given below.

Preferably, $R^6$ is selected from the group consisting of hydrogen, $C_1$-$C_6$-alkyl, fluorinated $C_1$-$C_6$-alkyl, —C(=O)$R^{10}$, —$SO_2R^{10}$, phenyl and benzyl, where the phenyl moiety in the two last-mentioned radicals may carry 1, 2 or 3 radicals $R^{11}$; or $R^{5a}$ and $R^6$, together with the atoms they are bound to, form a 3-, 4-, 5-, 6- or 7-membered saturated, partially unsaturated or maximally unsaturated heterocyclic ring, where the ring may further contain 1, 2, 3 or 4 heteroatoms or heteroatom-containing groups selected from O, S, N, SO, $SO_2$, C=O and C=S as ring members, and where the ring may be substituted with one or more substituents $R^{11}$;

where $R^{10}$ and $R^{11}$ have one of the general meanings given above, or, in particular, one of the preferred meanings given below.

In the above group —C(=O)$R^{10}$, $R^6$, $R^{10}$ is preferably selected from $C_1$-$C_4$-alkyl and $C_1$-$C_4$-alkoxy and more preferably from $C_1$-$C_2$-alkyl and tert-butoxy.

In the above group —$SO_2R^{10}$, $R^6$, $R^{10}$ is preferably selected from $C_1$-$C_6$-alkyl, fluorinated $C_1$-$C_6$-alkyl and phenyl, where phenyl may be substituted with 1, 2, 3, 4 or 5, preferably 1, 2 or 3, in particular 1, radicals $R^{11}$, where $R^{11}$ has one of the general meanings given above, or, in particular, one of the preferred meanings given below.

In one more preferred embodiment, $R^6$ is —$SO_2R^{10}$, where $R^{10}$ has one of the general meanings given above or is preferably selected from $C_1$-$C_6$-alkyl, fluorinated $C_1$-$C_6$-alkyl and phenyl, where phenyl may be substituted with 1, 2, 3, 4 or 5, preferably 1, 2 or 3, in particular 1, radicals $R^{11}$, where $R^{11}$ has one of the general meanings given above, or, in particular, one of the preferred meanings given below.

In another preferred embodiment, $R^6$ is selected from $C_1$-$C_6$-alkyl, fluorinated $C_1$-$C_6$-alkyl, $C_3$-$C_6$-cycloalkyl, fluorinated $C_3$-$C_6$-cycloalkyl, $C_3$-$C_6$-cycloalkyl-$C_1$-$C_2$-alkyl, fluorinated $C_3$-$C_6$-cycloalkyl-$C_1$-$C_2$-alkyl, phenyl, phenyl-$C_1$-$C_2$-alkyl and a 3-, 4-, 5- or 6-membered saturated heterocyclic ring containing 1, 2, 3 or 4 heteroatoms or heteroatom groups independently selected from N, O, S, NO, SO and $SO_2$ and optionally also 1 or 2 C=O and/or C=S groups as ring members, where the cyclic moieties in the three last-mentioned radicals may be substituted with one or more substituents $R^{11}$.

In a more preferred embodiment, $R^6$ is phenyl-$C_1$-$C_2$-alkyl, and in particular benzyl.

In another more preferred embodiment, $R^6$ is selected from $C_1$-$C_6$-alkyl, fluorinated $C_1$-$C_6$-alkyl, $C_3$-$C_6$-cycloalkyl, fluorinated $C_3$-$C_6$-cycloalkyl, $C_3$-$C_6$-cycloalkyl-$C_1$-$C_2$-alkyl and fluorinated $C_3$-$C_6$-cycloalkyl-$C_1$-$C_2$-alkyl, and in particular from $C_1$-$C_4$-alkyl, fluorinated $C_1$-$C_4$-alkyl, $C_3$-$C_6$-cycloalkyl, fluorinated $C_3$-$C_6$-cycloalkyl, $C_3$-$C_6$-cycloalkyl-methyl and fluorinated $C_3$-$C_6$-cycloalkyl-methyl.

In another more preferred embodiment, $R^6$ is a 3-, 4-, 5- or 6-membered saturated heterocyclic ring containing 1, 2, 3 or 4 heteroatoms or heteroatom groups independently selected from N, O, S, NO, SO and $SO_2$ and optionally also 1 or 2 C=O and/or C=S groups as ring members, where the cyclic moieties in the three last-mentioned radicals may be substituted with one or more substituents $R^{11}$. Even more preferably, $R^6$ is a 3-, 4- or 5-membered saturated heterocyclic ring containing 1 or 2 heteroatoms independently selected from N, O and S, where the heterocyclic ring may be substituted with one or two substituents selected from halogen and $C_1$-$C_4$-alkyl, and is in particular oxetanyl which may carry one or two substituents selected from halogen and $C_1$-$C_4$-alkyl and especially from F.

In another more preferred embodiment, $R^{5a}$ and $R^6$, together with the atoms they are bound to, form a 3-, 4-, 5-, 6- or 7-membered saturated, partially unsaturated or maximally unsaturated heterocyclic ring, where the ring may further contain 1, 2, 3 or 4 heteroatoms or heteroatom-containing groups selected from O, S, N, SO, $SO_2$, C=O and C=S as ring members, and where the ring may be substituted with one or more substituents $R^{11}$;

where $R^{11}$ has one of the general meanings given above, or, in particular, one of the preferred meanings given below.

In particular, $R^{5a}$ and $R^6$ form together a group $(CH_2)_r$, where r is 2, 3, 4 or 5, preferably 2, 3 or 4.

In an alternative embodiment, X is $CR^7R^8$, where $R^7$ and $R^8$ have one of the general meanings given above, or, in particular, one of the preferred meanings given below.

In case that $R^7$ and $R^8$, together with the carbon atom they are bound to, form a ring, this ring is spiro-bound to the carbon atom carrying $R^7$ and $R^8$.

Preferably, $R^7$ and $R^8$, independently of each other, are selected from the group consisting of halogen, cyano, nitro, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, $-NR^{12a}R^{12b}$, $-CH_2NR^{12a}R^{12b}$, $-NR^{12a}C(O)R^{10}$, $-C(=O)R^{10}$, $SO_2NR^{12a}R^{12b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{11}$; or $R^7$ and $R^8$, together with the carbon atom they are bound to, form a 3-, 4-, 5-, 6-, 7- or 8-membered saturated, partially unsaturated or maximally unsaturated ring, where the ring may contain 1, 2, 3 or 4 heteroatoms or heteroatom-containing groups selected from O, S, N, SO, $SO_2$, C=O and C=S as ring members, and where the ring may be substituted with one or more substituents $R^{11}$; or $R^{5a}$ and $R^7$, together with the carbon atoms they are bound to, form a 3-, 4-, 5-, 6-, 7- or 8-membered saturated, partially unsaturated or maximally unsaturated ring, where the ring may contain 1, 2, 3 or 4 heteroatoms or heteroatom-containing groups selected from O, S, N, SO, $SO_2$, C=O and C=S as ring members, and where the ring may be substituted with one or more substituents $R^{11}$;

in which case $R^8$ has one of the above meanings or is deuterium;

where $R^{11}$ has one of the general meanings given above, or, in particular, one of the preferred meanings given below.

More preferably, $R^7$ and $R^8$, independently of each other, are selected from halogen, cyano, $C_1$-$C_6$-alkyl, fluorinated $C_1$-$C_6$-alkyl, $C_1$-$C_6$-alkoxy, fluorinated $C_1$-$C_6$-alkoxy, phenyl, phenyl-$C_1$-$C_2$-alkyl, benzyloxy and a 3-, 4-, 5- or 6-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the four last-mentioned radicals may be substituted with one or more substituents $R^{11}$; or $R^7$ and $R^8$, together with the carbon atom they are bound to, form a 3-, 4-, 5-, 6- or 7- or 8-membered saturated, partially unsaturated or maximally unsaturated ring, where the ring may contain 1, 2, 3 or 4 heteroatoms or heteroatom-containing groups selected from O, S, N, SO, $SO_2$, C=O and C=S as ring members, and where the ring may be substituted with one or more substituents $R^{11}$; or $R^{5a}$ and $R^7$, together with the carbon atoms they are bound to, form a 3-, 4-, 5-, 6- or 7-membered saturated, partially unsaturated or maximally unsaturated ring, where the ring may contain 1, 2, 3 or 4 heteroatoms or heteroatom-containing groups selected from O, S, N, SO, $SO_2$, C=O and C=S as ring members, and where the ring may be substituted with one or more substituents $R^{11}$;

in which case $R^8$ has one of the above meanings or is deuterium; and $R^{5b}$ is selected from hydrogen and deuterium and is preferably hydrogen; where $R^{11}$ has one of the general meanings given above, or, in particular, one of the preferred meanings given below.

Even more preferably, $R^7$ and $R^8$, independently of each other, are selected from halogen, cyano, $C_1$-$C_6$-alkyl, fluorinated $C_1$-$C_6$-alkyl and phenyl, or $R^7$ and $R^8$, together with the carbon atom they are bound to, form a 3-, 4-, 5-, 6- or 7- or 8-membered saturated, partially unsaturated or maximally unsaturated ring, where the ring may be substituted with one or more substituents $R^{11}$; or $R^5$ and $R^7$ form together a group $(CH_2)_s$, where s is 2, 3, 4 or 5, preferably 2, 3 or 4; in which case $R^8$ has one of the above meanings or is deuterium; and $R^{5b}$ is selected from hydrogen and deuterium and is preferably hydrogen;

where $R^{11}$ has one of the general meanings given above, or, in particular, one of the preferred meanings given below.

In particular, $R^8$ is selected from halogen, cyano, $C_1$-$C_6$-alkyl, fluorinated $C_1$-$C_6$-alkyl and phenyl; and $R^7$ is selected from $C_1$-$C_6$-alkyl and fluorinated $C_1$-$C_6$-alkyl, preferably from methyl and $CF_3$ and is in particular methyl; or $R^7$ and $R^8$, together with the carbon atom they are bound to, form a 3-, 4-, 5-, 6- or 7- or 8-membered saturated, partially unsaturated or maximally unsaturated ring, where the ring may be substituted with one or more substituents $R^{11}$; or $R^{5a}$ and $R^7$ form together a group $(CH_2)_s$, where s is 2, 3, 4 or 5, preferably 2, 3 or 4; in which case $R^8$ has one of the above meanings or is deuterium; and $R^{5b}$ is selected from hydrogen and deuterium and is preferably hydrogen;

where $R^{11}$ has one of the general meanings given above, or, in particular, one of the preferred meanings given below. Specifically, $R^8$ is selected from $C_1$-$C_4$-alkyl, fluorinated $C_1$-$C_2$-alkyl and phenyl and specifically from methyl, $CF_3$ and phenyl; and $R^7$ is methyl; or $R^7$ and $R^8$, together with the carbon atom they are bound to, form a 3-, 4-, 5- or 6-membered saturated or partially unsaturated ring, where the ring may be substituted with one or more substituents $R^{11}$; or $R^{5a}$ and $R^7$ form together a group $(CH_2)_s$, where s is 3 or 4, specifically 3; in which case $R^8$ is selected from methyl and deuterium; and $R^{5b}$ is selected from hydrogen and deuterium and is specifically hydrogen;

where $R^{11}$ has one of the general meanings given above, or, in particular, one of the preferred meanings given below. Very specifically, $R^8$ is selected from methyl, $CF_3$ and phenyl; and $R^7$ is methyl; or $R^7$ and $R^8$, together with the carbon atom they are bound to, form a 4,5- or 6-membered saturated or partially unsaturated ring, where the ring may be substituted with one or more substituents $R^{11}$; or $R^{5a}$ and $R^7$ form together a group $(CH_2)_s$, where s is 3 or 4, specifically 3;

in which case $R^8$ is selected from methyl and deuterium; and $R^{5b}$ is selected from hydrogen and deuterium and is specifically hydrogen;

where $R^{11}$ has one of the general meanings given above, or, in particular, one of the preferred meanings given below.

In one particular embodiment, the ring formed by $R^7$ and $R^8$ together with the carbon atom they are bound to is a carbocyclic ring, preferably a saturated or partially unsaturated carbocyclic ring.

If $R^7$ and $R^8$, together with the carbon atom they are bound to, form a carbocyclic ring, this is particularly preferably a 4- or 5-membered saturated carbocyclic ring (i.e. $R^7$ and $R^8$ form together a group —$(CH_2)_3$— or —$(CH_2)_4$—) and in particular a 4-membered saturated carbocyclic ring (i.e. $R^7$ and $R^8$ form together a group —$(CH_2)_3$—), where the ring may be substituted with one or more substituents $R^{11}$. Specifically, the ring is not substituted.

In an alternative particular embodiment, the ring formed by $R^7$ and $R^8$ together with the carbon atom they are bound to is a heterocyclic ring containing 1, 2, 3 or 4 heteroatoms or heteroatom-containing groups selected from O, S, N, SO and $SO_2$ as ring members, preferably containing 1 or 2 heteroatoms or heteroatom-containing groups selected from O, S, N, SO and $SO_2$ as ring members. Preferably, the heterocyclic ring is 3-, 4-, 5- or 6-membered and saturated and may carry one or more substituents $R^{11}$. In particular, the heterocyclic ring is oxetanyl which may carry one or more substituents $R^{11}$.

In a preferred embodiment, each $R^9$ is independently selected from halogen, cyano, nitro, hydroxy, $C_1$-$C_6$-alkyl, fluorinated $C_1$-$C_6$-alkyl, $C_3$-$C_6$-cycloalkyl, fluorinated $C_3$-$C_6$-cycloalkyl, $C_1$-$C_6$-alkoxy, fluorinated $C_1$-$C_6$-alkoxy and a 3-, 4-, 5- or 6-membered saturated heterocyclic ring containing 1 or 2 heteroatoms or heteroatom groups independently selected from N, O, S, NO, SO and $SO_2$ as ring members, where the heterocyclic ring may be substituted with one or more substituents $R^{11}$. The heterocyclic ring is specifically oxetanyl.

More preferably, each $R^9$ is independently selected from halogen, cyano, nitro, hydroxy, $C_1$-$C_6$-alkyl, fluorinated $C_1$-$C_6$-alkyl, $C_1$-$C_6$-alkoxy and fluorinated $C_1$-$C_6$-alkoxy, even more preferably from halogen, cyano, $C_1$-$C_4$-alkyl, fluorinated $C_1$-$C_4$-alkyl, $C_1$-$C_4$-alkoxy and fluorinated $C_1$-$C_4$-alkoxy, and is in particular halogen, especially F or Cl, and more specifically F.

In a preferred embodiment, $R^{10}$ is selected from hydrogen, hydroxy, $C_1$-$C_6$-alkyl, fluorinated $C_1$-$C_6$-alkyl, $C_1$-$C_6$-hydroxyalkyl, $C_3$-$C_8$-cycloalkyl, fluorinated $C_3$-$C_8$-cycloalkyl, $C_1$-$C_6$-alkoxy, fluorinated $C_1$-$C_6$-alkoxy, —$NR^{12a}R^{12b}$, —$CH_2NR^{12a}R^{12b}$, phenyl, phenyl-$C_1$-$C_2$-alkyl, phenoxy, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the five last-mentioned radicals may be substituted with one or more substituents $R^{11}$, where $R^1$, $R^{12a}$ and $R^{12b}$ have one of the general meanings given above, or, in particular, one of the preferred meanings given below. More preferably, $R^{10}$ is selected from hydrogen, $C_1$-$C_6$-alkyl, fluorinated $C_1$-$C_6$-alkyl, $C_1$-$C_6$-alkoxy and fluorinated $C_1$-$C_6$-alkoxy, and even more preferably from $C_1$-$C_4$-alkyl and $C_1$-$C_4$-alkoxy. In particular, $R^{10}$ is selected from $C_1$-$C_2$-alkyl and tert-butoxy.

In a preferred embodiment, each $R^{11}$ is independently selected from halogen, cyano, nitro, hydroxy, $C_1$-$C_6$-alkyl, fluorinated $C_1$-$C_6$-alkyl, $C_1$-$C_6$-alkoxy and fluorinated $C_1$-$C_6$-alkoxy, and is in particular halogen or $C_1$-$C_4$-alkyl.

In a preferred embodiment, $R^{12a}$ and $R^{12b}$, independently of each other and independently of each occurrence, are selected from hydrogen, $C_1$-$C_6$-alkyl, fluorinated $C_1$-$C_6$-alkyl, $C_1$-$C_6$-alkylcarbonyl, fluorinated $C_1$-$C_6$-alkylcarbonyl, $C_1$-$C_6$-alkoxycarbonyl, fluorinated $C_1$-$C_6$-alkoxycarbonyl, phenyl and benzyl, where the phenyl moieties in the two last-mentioned radicals may carry 1, 2 or 3 substituents selected from halogen, cyano nitro, $C_1$-$C_6$-alkyl, fluorinated $C_1$-$C_6$-alkyl, $C_1$-$C_6$-alkoxy and fluorinated $C_1$-$C_6$-alkoxy; or, if $R^{12a}$ and $R^{12b}$ are bound to the same nitrogen atom, together with this nitrogen atom may form a 3-, 4-, 5-, 6- or 7-membered saturated, partially unsaturated or maximally unsaturated heterocyclic ring, where the ring may further contain 1 or 2 heteroatoms or heteroatom-containing groups selected from O, S, N, SO, $SO_2$, C=O and C=S as ring members, and where the ring may be substituted with one or more substituents selected from halogen, cyano nitro, $C_1$-$C_6$-alkyl, fluorinated $C_1$-$C_6$-alkyl, $C_1$-$C_6$-alkoxy and fluorinated $C_1$-$C_6$-alkoxy.

More preferably, $R^{12a}$ and $R^{12b}$, independently of each other and independently of each occurrence, are selected from hydrogen, $C_1$-$C_6$-alkyl, $C_1$-$C_6$-alkylcarbonyl, $C_1$-$C_6$-alkoxycarbonyl and benzyl, where the phenyl moiety in the last-mentioned radical may carry 1, 2 or 3 substituents selected from halogen, cyano nitro, $C_1$-$C_4$-alkyl, fluorinated $C_1$-$C_4$-alkyl, $C_1$-$C_4$-alkoxy and fluorinated $C_1$-$C_4$-alkoxy; or, if $R^{12a}$ and $R^{12b}$ are bound to the same nitrogen atom, together with this nitrogen atom may form a 5- or 6-membered saturated or aromatic heterocyclic ring, where the ring may further contain 1 or 2 heteroatoms or heteroatom-containing groups selected from O, S, N, SO, $SO_2$ and C=O as ring members, and where the ring may be substituted with 1 or 2 substituents selected from halogen, cyano nitro, $C_1$-$C_4$-alkyl, fluorinated $C_1$-$C_4$-alkyl, $C_1$-$C_4$-alkoxy and fluorinated $C_1$-$C_4$-alkoxy.

In particular, $R^{12a}$ and $R^{12b}$, independently of each other and independently of each occurrence, are selected from hydrogen and $C_1$-$C_6$-alkyl.

In a preferred embodiment, a is 0 or 1 and in particular 0.

In a preferred embodiment, b is 0, 1 or 2 and in particular 0 or 1.

In a preferred embodiment, n is 1.
In a particular embodiment, the compound of formula I is a compound of formula I.1

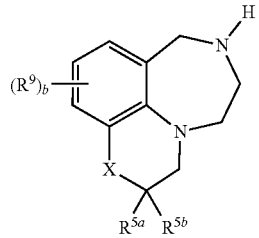
(I.1)

wherein X, $R^{5a}$, $R^{5b}$, $R^9$ and b have one of the above general, or, in particular, one of the above preferred meanings.
In a specific embodiment, the compound of formula I is a compound of formula I.1.1

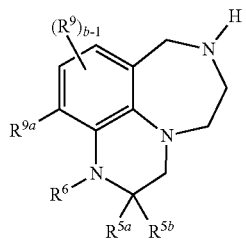
(I.1.1)

wherein
$R^{9a}$ is H or F; and
$R^{5a}$, $R^{5b}$, $R^6$, $R^9$ and b have one of the above general, or, in particular, one of the above preferred meanings.
In another specific embodiment, the compound of formula I is a compound of formula I.1.2

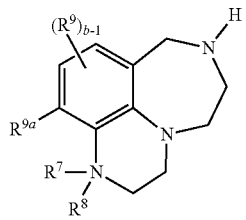
(I.1.2)

wherein
$R^7$ is selected from $C_1$-$C_4$-alkyl and fluorinated $C_1$-$C_4$-alkyl, preferably from methyl and $CF_3$, and is in particular methyl;
$R^8$ is selected from $C_1$-$C_4$-alkyl and fluorinated $C_1$-$C_4$-alkyl, and preferably from methyl and $CF_3$; or
$R^7$ and $R^8$, together with the carbon atom they are bound to, form a 3-, 4-, 5-, 6- or 7-membered saturated or partially unsaturated ring, where the ring may be substituted with one or more substituents $R^{11}$, and form preferably a 5- or 6-membered saturated or partially unsaturated ring;
$R^{9a}$ is H or F; and
$R^9$ and b have one of the above general, or, in particular, one of the above preferred meanings.
In another specific embodiment, the compound of formula I is a compound of formula I.1.3

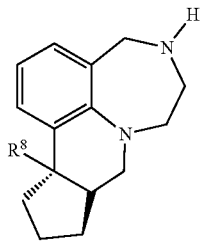
(I.1.3)

wherein $R^8$ is selected from deuterium, F, Cl and CN.
In another particular embodiment, the compound of formula I is a compound of formula I.2

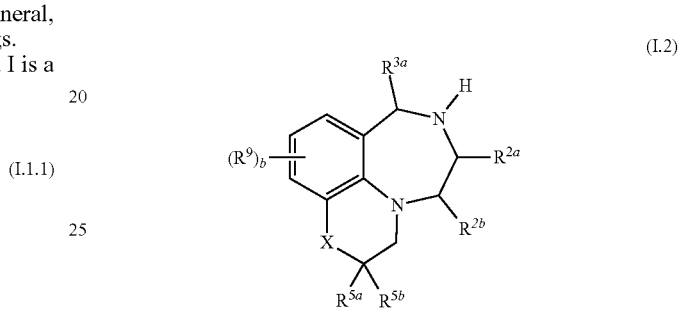
(I.2)

wherein X, $R^{5a}$, $R^{5b}$, $R^9$ and b have one of the above general, or, in particular, one of the above preferred meanings.
In another particular embodiment, the compound of formula I is a compound of formula I.2.1

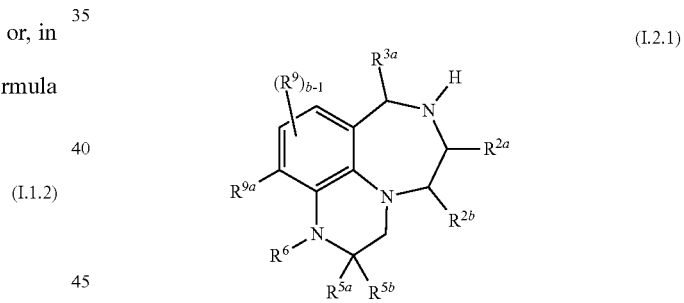
(I.2.1)

wherein
$R^{9a}$ is H or F; and
$R^{5a}$, $R^{5b}$, $R^6$, $R^9$ and b have one of the above general, or, in particular, one of the above preferred meanings.
In another particular embodiment, the compound of formula I is a compound of formula I.2.2

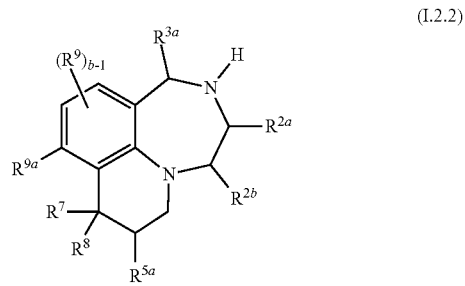
(I.2.2)

wherein
- $R^{2a}$, $R^{2b}$, $R^{3a}$ and $R^{5a}$, independently of each other, are selected from hydrogen and methyl;
- $R^7$ is selected from $C_1$-$C_4$-alkyl and fluorinated $C_1$-$C_4$-alkyl, preferably from methyl and $CF_3$, and is in particular methyl;
- $R^8$ is selected from $C_1$-$C_4$-alkyl and fluorinated $C_1$-$C_4$-alkyl, and preferably from methyl and $CF_3$; or
- $R^7$ and $R^8$, together with the carbon atom they are bound to, form a 3-, 4-, 5-, 6- or 7-membered saturated or partially unsaturated ring, where the ring may be substituted with one or more substituents $R^{11}$;
- $R^{9a}$ is H or F; and
- $R^9$ and b have one of the above general, or, in particular, one of the above preferred meanings.

In the above formulae I.1.1, I.1.2, I.2.1 and I.2.2, (b-1) is preferably 0.

Preferably, in the above formulae I.2, I.2.1 and I.2.2, $R^{2a}$, $R^{2b}$, $R^{3a}$ and $R^{5a}$ are selected from hydrogen and methyl, with the proviso that at most two, preferably at most one, of the substituents $R^{2a}$, $R^{2b}$, $R^{3a}$ and $R^{5a}$ are methyl. In particular, $R^{2b}$ is hydrogen and $R^{2a}$, $R^{3a}$ and $R^{5a}$ are selected from hydrogen and methyl, with the proviso that at most two, preferably at most one, of the substituents $R^{2a}$, $R^{3a}$ and $R^{5a}$ are methyl.

Preferably, in the above formulae I.2, I.2.1 and I.2.2, $R^7$ and $R^8$, together with the carbon atom they are bound to, form a 4-, 5- or 6-membered saturated or partially unsaturated carbocyclic ring, preferably a 4- or 5-membered saturated carbocyclic ring, in particular a 4-membered saturated carbocyclic ring, where the ring may be substituted with one or more substituents $R^{11}$.

Examples of preferred compounds are compounds of the following formulae I.a to I.u, where the variables have one of the general or preferred meanings given above. Examples of preferred compounds are the individual compounds compiled in the tables 1 to 21 below. Moreover, the meanings mentioned below for the individual variables in the tables are per se, independently of the combination in which they are mentioned, a particularly preferred embodiment of the substituents in question.

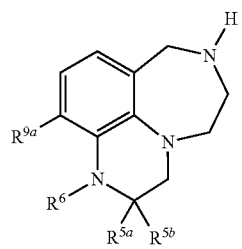

I.a

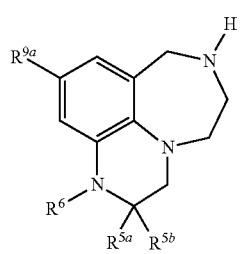

I.b

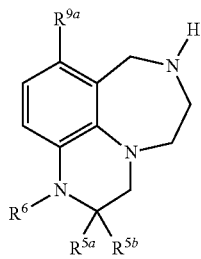

I.c

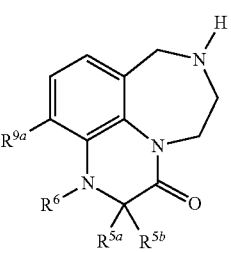

I.d

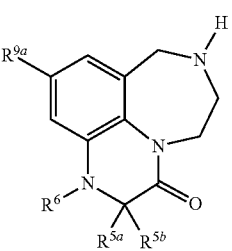

I.e

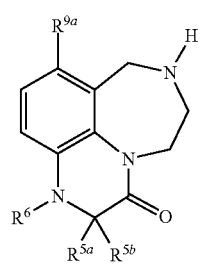

I.f

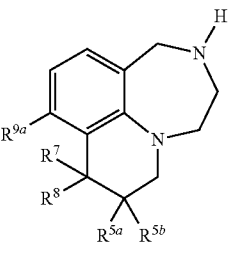

I.g

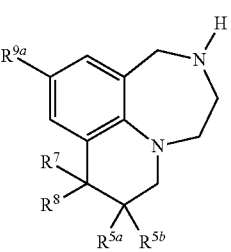

I.h

I.i 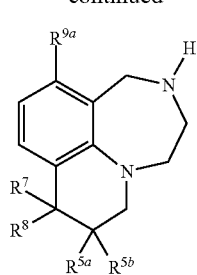

I.j 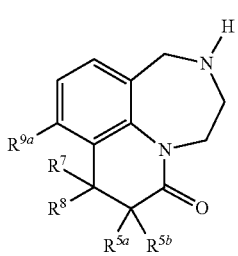

I.k 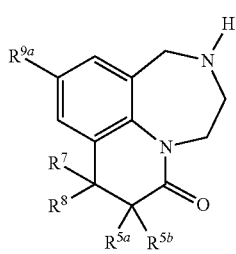

I.l 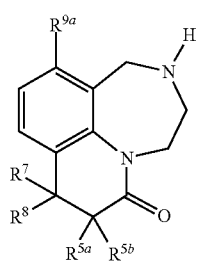

Table 1
Compounds of the formula I.a in which the combination of $R^{5a}, R^{5b}, R^6$ and $R^{9a}$ for a compound corresponds in each case to one row of Table A.
Table 2
Compounds of the formula I.b in which the combination of $R^{5a}, R^{5b}, R^6$ and $R^{9a}$ for a compound corresponds in each case to one row of Table A.
Table 3
Compounds of the formula I.c in which the combination of $R^{5a}, R^{5b}, R^6$ and $R^{9a}$ for a compound corresponds in each case to one row of Table A.
Table 4
Compounds of the formula I.d in which the combination of $R^{5a}, R^{5b}, R^6$ and $R^{9a}$ for a compound corresponds in each case to one row of Table A.
Table 5
Compounds of the formula I.e in which the combination of $R^{5a}, R^{5b}, R^6$ and $R^{9a}$ for a compound corresponds in each case to one row of Table A.
Table 6
Compounds of the formula I.f in which the combination of $R^{5a}, R^{5b}, R^6$ and $R^{9a}$ for a compound corresponds in each case to one row of Table A.
Table 7
Compounds of the formula I.g in which the combination of $R^{5a}, R^{5b}, R^7, R^8$ and $R^{9a}$ for a compound corresponds in each case to one row of Table B.
Table 8
Compounds of the formula I.h in which the combination of $R^{5a}, R^{5b}, R^7, R^8$ and $R^{9a}$ for a compound corresponds in each case to one row of Table B.
Table 9
Compounds of the formula I.i in which the combination of $R^{5a}, R^{5b}, R^7, R^8$ and $R^{9a}$ for a compound corresponds in each case to one row of Table B.
Table 10
Compounds of the formula I.j in which the combination of $R^{5a}, R^{5b}, R^7, R^8$ and $R^{9a}$ for a compound corresponds in each case to one row of Table B.
Table 11
Compounds of the formula I.k in which the combination of $R^{5a}, R^{5b}, R^7, R^8$ and $R^{9a}$ for a compound corresponds in each case to one row of Table B.
Table 12
Compounds of the formula I.1 in which the combination of $R^{5a}, R^{5b}, R^7, R^8$ and $R^{9a}$ for a compound corresponds in each case to one row of Table B.
Table 13
Compounds of the formula I.m in which the combination of $R^{5a}, R^{5b}, R^7, R^8$ and $R^{9a}$ for a compound corresponds in each case to one row of Table B.
Table 14
Compounds of the formula I.n in which the combination of $R^{5a}, R^{5b}, R^7, R^8$ and $R^{9a}$ for a compound corresponds in each case to one row of Table B.
Table 15
Compounds of the formula I.o in which the combination of $R^{5a}, R^{5b}, R^7, R^8$ and $R^{9a}$ for a compound corresponds in each case to one row of Table B.
Table 16
Compounds of the formula I.p in which the combination of $R^{5a}, R^{5b}, R^7, R^8$ and $R^{9a}$ for a compound corresponds in each case to one row of Table B.
Table 17
Compounds of the formula I.q in which the combination of $R^{5a}, R^{5b}, R^7, R^8$ and $R^{9a}$ for a compound corresponds in each case to one row of Table B.
Table 18
Compounds of the formula I.r in which the combination of $R^{5a}, R^{5b}, R^7, R^8$ and $R^{9a}$ for a compound corresponds in each case to one row of Table B.
Table 19
Compounds of the formula I.s in which the combination of $R^{5a}, R^{5b}, R^7, R^8$ and $R^{9a}$ for a compound corresponds in each case to one row of Table B.
Table 20
Compounds of the formula I.t in which the combination of $R^{5a}, R^{5b}, R^7, R^8$ and $R^{9a}$ for a compound corresponds in each case to one row of Table B.
Table 21
Compounds of the formula I.u in which the combination of $R^{5a}, R^{5b}, R^7, R^8$ and $R^{9a}$ for a compound corresponds in each case to one row of Table B.

TABLE A

| No. | $R^{9a}$ | $R^{5b}$ | $R^{5a}$ | $R^6$ |
|---|---|---|---|---|
| A-1 | H | H | H | —$SO_2$—$CH_3$ |
| A-2 | F | H | H | —$SO_2$—$CH_3$ |

TABLE A-continued

| No. | $R^{9a}$ | $R^{5b}$ | $R^{5a}$ | $R^6$ |
|---|---|---|---|---|
| A-3 | Cl | H | H | —SO$_2$—CH$_3$ |
| A-4 | Br | H | H | —SO$_2$—CH$_3$ |
| A-5 | CH$_3$ | H | H | —SO$_2$—CH$_3$ |
| A-6 | CF$_3$ | H | H | —SO$_2$—CH$_3$ |
| A-7 | OCH$_3$ | H | H | —SO$_2$—CH$_3$ |
| A-8 | OCF$_3$ | H | H | —SO$_2$—CH$_3$ |
| A-9 | H | CH$_3$ | H | —SO$_2$—CH$_3$ |
| A-10 | F | CH$_3$ | H | —SO$_2$—CH$_3$ |
| A-11 | Cl | CH$_3$ | H | —SO$_2$—CH$_3$ |
| A-12 | Br | CH$_3$ | H | —SO$_2$—CH$_3$ |
| A-13 | CH$_3$ | CH$_3$ | H | —SO$_2$—CH$_3$ |
| A-14 | CF$_3$ | CH$_3$ | H | —SO$_2$—CH$_3$ |
| A-15 | OCH$_3$ | CH$_3$ | H | —SO$_2$—CH$_3$ |
| A-16 | OCF$_3$ | CH$_3$ | H | —SO$_2$—CH$_3$ |
| A-17 | H | CH$_3$ | CH$_3$ | —SO$_2$—CH$_3$ |
| A-18 | F | CH$_3$ | CH$_3$ | —SO$_2$—CH$_3$ |
| A-19 | Cl | CH$_3$ | CH$_3$ | —SO$_2$—CH$_3$ |
| A-20 | Br | CH$_3$ | CH$_3$ | —SO$_2$—CH$_3$ |
| A-21 | CH$_3$ | CH$_3$ | CH$_3$ | —SO$_2$—CH$_3$ |
| A-22 | CF$_3$ | CH$_3$ | CH$_3$ | —SO$_2$—CH$_3$ |
| A-23 | OCH$_3$ | CH$_3$ | CH$_3$ | —SO$_2$—CH$_3$ |
| A-24 | OCF$_3$ | CH$_3$ | CH$_3$ | —SO$_2$—CH$_3$ |
| A-25 | H | H | H | —SO$_2$—CH$_2$CH$_3$ |
| A-26 | F | H | H | —SO$_2$—CH$_2$CH$_3$ |
| A-27 | Cl | H | H | —SO$_2$—CH$_2$CH$_3$ |
| A-28 | Br | H | H | —SO$_2$—CH$_2$CH$_3$ |
| A-29 | CH$_3$ | H | H | —SO$_2$—CH$_2$CH$_3$ |
| A-30 | CF$_3$ | H | H | —SO$_2$—CH$_2$CH$_3$ |
| A-31 | OCH$_3$ | H | H | —SO$_2$—CH$_2$CH$_3$ |
| A-32 | OCF$_3$ | H | H | —SO$_2$—CH$_2$CH$_3$ |
| A-33 | H | CH$_3$ | H | —SO$_2$—CH$_2$CH$_3$ |
| A-34 | F | CH$_3$ | H | —SO$_2$—CH$_2$CH$_3$ |
| A-35 | Cl | CH$_3$ | H | —SO$_2$—CH$_2$CH$_3$ |
| A-36 | Br | CH$_3$ | H | —SO$_2$—CH$_2$CH$_3$ |
| A-37 | CH$_3$ | CH$_3$ | H | —SO$_2$—CH$_2$CH$_3$ |
| A-38 | CF$_3$ | CH$_3$ | H | —SO$_2$—CH$_2$CH$_3$ |
| A-39 | OCH$_3$ | CH$_3$ | H | —SO$_2$—CH$_2$CH$_3$ |
| A-40 | OCF$_3$ | CH$_3$ | H | —SO$_2$—CH$_2$CH$_3$ |
| A-41 | H | CH$_3$ | CH$_3$ | —SO$_2$—CH$_2$CH$_3$ |
| A-42 | F | CH$_3$ | CH$_3$ | —SO$_2$—CH$_2$CH$_3$ |
| A-43 | Cl | CH$_3$ | CH$_3$ | —SO$_2$—CH$_2$CH$_3$ |
| A-44 | Br | CH$_3$ | CH$_3$ | —SO$_2$—CH$_2$CH$_3$ |
| A-45 | CH$_3$ | CH$_3$ | CH$_3$ | —SO$_2$—CH$_2$CH$_3$ |
| A-46 | CF$_3$ | CH$_3$ | CH$_3$ | —SO$_2$—CH$_2$CH$_3$ |
| A-47 | OCH$_3$ | CH$_3$ | CH$_3$ | —SO$_2$—CH$_2$CH$_3$ |
| A-48 | OCF$_3$ | CH$_3$ | CH$_3$ | —SO$_2$—CH$_2$CH$_3$ |
| A-49 | H | H | H | —SO$_2$—CF$_3$ |
| A-50 | F | H | H | —SO$_2$—CF$_3$ |
| A-51 | Cl | H | H | —SO$_2$—CF$_3$ |
| A-52 | Br | H | H | —SO$_2$—CF$_3$ |
| A-53 | CH$_3$ | H | H | —SO$_2$—CF$_3$ |
| A-54 | CF$_3$ | H | H | —SO$_2$—CF$_3$ |
| A-55 | OCH$_3$ | H | H | —SO$_2$—CF$_3$ |
| A-56 | OCF$_3$ | H | H | —SO$_2$—CF$_3$ |
| A-57 | H | CH$_3$ | H | —SO$_2$—CF$_3$ |
| A-58 | F | CH$_3$ | H | —SO$_2$—CF$_3$ |
| A-59 | Cl | CH$_3$ | H | —SO$_2$—CF$_3$ |
| A-60 | Br | CH$_3$ | H | —SO$_2$—CF$_3$ |
| A-61 | CH$_3$ | CH$_3$ | H | —SO$_2$—CF$_3$ |
| A-62 | CF$_3$ | CH$_3$ | H | —SO$_2$—CF$_3$ |
| A-63 | OCH$_3$ | CH$_3$ | H | —SO$_2$—CF$_3$ |
| A-64 | OCF$_3$ | CH$_3$ | H | —SO$_2$—CF$_3$ |
| A-65 | H | CH$_3$ | CH$_3$ | —SO$_2$—CF$_3$ |
| A-66 | F | CH$_3$ | CH$_3$ | —SO$_2$—CF$_3$ |
| A-67 | Cl | CH$_3$ | CH$_3$ | —SO$_2$—CF$_3$ |
| A-68 | Br | CH$_3$ | CH$_3$ | —SO$_2$—CF$_3$ |
| A-69 | CH$_3$ | CH$_3$ | CH$_3$ | —SO$_2$—CF$_3$ |
| A-70 | CF$_3$ | CH$_3$ | CH$_3$ | —SO$_2$—CF$_3$ |
| A-71 | OCH$_3$ | CH$_3$ | CH$_3$ | —SO$_2$—CF$_3$ |
| A-72 | OCF$_3$ | CH$_3$ | CH$_3$ | —SO$_2$—CF$_3$ |
| A-73 | H | H | H | —SO$_2$—C$_6$H$_5$* |
| A-74 | F | H | H | —SO$_2$—C$_6$H$_5$ |
| A-75 | Cl | H | H | —SO$_2$—C$_6$H$_5$ |
| A-76 | Br | H | H | —SO$_2$—C$_6$H$_5$ |
| A-77 | CH$_3$ | H | H | —SO$_2$—C$_6$H$_5$ |
| A-78 | CF$_3$ | H | H | —SO$_2$—C$_6$H$_5$ |
| A-79 | OCH$_3$ | H | H | —SO$_2$—C$_6$H$_5$ |
| A-80 | OCF$_3$ | H | H | —SO$_2$—C$_6$H$_5$ |
| A-81 | H | CH$_3$ | H | —SO$_2$—C$_6$H$_5$ |
| A-82 | F | CH$_3$ | H | —SO$_2$—C$_6$H$_5$ |
| A-83 | Cl | CH$_3$ | H | —SO$_2$—C$_6$H$_5$ |
| A-84 | Br | CH$_3$ | H | —SO$_2$—C$_6$H$_5$ |
| A-85 | CH$_3$ | CH$_3$ | H | —SO$_2$—C$_6$H$_5$ |
| A-86 | CF$_3$ | CH$_3$ | H | —SO$_2$—C$_6$H$_5$ |
| A-87 | OCH$_3$ | CH$_3$ | H | —SO$_2$—C$_6$H$_5$ |
| A-88 | OCF$_3$ | CH$_3$ | H | —SO$_2$—C$_6$H$_5$ |
| A-89 | H | CH$_3$ | CH$_3$ | —SO$_2$—C$_6$H$_5$ |
| A-90 | F | CH$_3$ | CH$_3$ | —SO$_2$—C$_6$H$_5$ |
| A-91 | Cl | CH$_3$ | CH$_3$ | —SO$_2$—C$_6$H$_5$ |
| A-92 | Br | CH$_3$ | CH$_3$ | —SO$_2$—C$_6$H$_5$ |
| A-93 | CH$_3$ | CH$_3$ | CH$_3$ | —SO$_2$—C$_6$H$_5$ |
| A-94 | CF$_3$ | CH$_3$ | CH$_3$ | —SO$_2$—C$_6$H$_5$ |
| A-95 | OCH$_3$ | CH$_3$ | CH$_3$ | —SO$_2$—C$_6$H$_5$ |
| A-96 | OCF$_3$ | CH$_3$ | CH$_3$ | —SO$_2$—C$_6$H$_5$ |
| A-97 | H | H | H | —SO$_2$—C$_6$H$_4$CH$_3$** |
| A-98 | F | H | H | —SO$_2$—C$_6$H$_4$CH$_3$ |
| A-99 | Cl | H | H | —SO$_2$—C$_6$H$_4$CH$_3$ |
| A-100 | Br | H | H | —SO$_2$—C$_6$H$_4$CH$_3$ |
| A-101 | CH$_3$ | H | H | —SO$_2$—C$_6$H$_4$CH$_3$ |
| A-102 | CF$_3$ | H | H | —SO$_2$—C$_6$H$_4$CH$_3$ |
| A-103 | OCH$_3$ | H | H | —SO$_2$—C$_6$H$_4$CH$_3$ |
| A-104 | OCF$_3$ | H | H | —SO$_2$—C$_6$H$_4$CH$_3$ |
| A-105 | H | CH$_3$ | H | —SO$_2$—C$_6$H$_4$CH$_3$ |
| A-106 | F | CH$_3$ | H | —SO$_2$—C$_6$H$_4$CH$_3$ |
| A-107 | Cl | CH$_3$ | H | —SO$_2$—C$_6$H$_4$CH$_3$ |
| A-108 | Br | CH$_3$ | H | —SO$_2$—C$_6$H$_4$CH$_3$ |
| A-109 | CH$_3$ | CH$_3$ | H | —SO$_2$—C$_6$H$_4$CH$_3$ |
| A-110 | CF$_3$ | CH$_3$ | H | —SO$_2$—C$_6$H$_4$CH$_3$ |
| A-111 | OCH$_3$ | CH$_3$ | H | —SO$_2$—C$_6$H$_4$CH$_3$ |
| A-112 | OCF$_3$ | CH$_3$ | H | —SO$_2$—C$_6$H$_4$CH$_3$ |
| A-113 | H | CH$_3$ | CH$_3$ | —SO$_2$—C$_6$H$_4$CH$_3$ |
| A-114 | F | CH$_3$ | CH$_3$ | —SO$_2$—C$_6$H$_4$CH$_3$ |
| A-115 | Cl | CH$_3$ | CH$_3$ | —SO$_2$—C$_6$H$_4$CH$_3$ |
| A-116 | Br | CH$_3$ | CH$_3$ | —SO$_2$—C$_6$H$_4$CH$_3$ |
| A-117 | CH$_3$ | CH$_3$ | CH$_3$ | —SO$_2$—C$_6$H$_4$CH$_3$ |
| A-118 | CF$_3$ | CH$_3$ | CH$_3$ | —SO$_2$—C$_6$H$_4$CH$_3$ |
| A-119 | OCH$_3$ | CH$_3$ | CH$_3$ | —SO$_2$—C$_6$H$_4$CH$_3$ |
| A-120 | OCF$_3$ | CH$_3$ | CH$_3$ | —SO$_2$—C$_6$H$_4$CH$_3$ |
| A-121 | H | H | H | benzyl |
| A-122 | F | H | H | benzyl |
| A-123 | Cl | H | H | benzyl |
| A-124 | Br | H | H | benzyl |
| A-125 | CH$_3$ | H | H | benzyl |
| A-126 | CF$_3$ | H | H | benzyl |
| A-127 | OCH$_3$ | H | H | benzyl |
| A-128 | OCF$_3$ | H | H | benzyl |
| A-129 | H | CH$_3$ | H | benzyl |
| A-130 | F | CH$_3$ | H | benzyl |
| A-131 | Cl | CH$_3$ | H | benzyl |
| A-132 | Br | CH$_3$ | H | benzyl |
| A-133 | CH$_3$ | CH$_3$ | H | benzyl |
| A-134 | CF$_3$ | CH$_3$ | H | benzyl |
| A-135 | OCH$_3$ | CH$_3$ | H | benzyl |
| A-136 | OCF$_3$ | CH$_3$ | H | benzyl |
| A-137 | H | CH$_3$ | CH$_3$ | benzyl |
| A-138 | F | CH$_3$ | CH$_3$ | benzyl |
| A-139 | Cl | CH$_3$ | CH$_3$ | benzyl |
| A-140 | Br | CH$_3$ | CH$_3$ | benzyl |
| A-141 | CH$_3$ | CH$_3$ | CH$_3$ | benzyl |
| A-142 | CF$_3$ | CH$_3$ | CH$_3$ | benzyl |
| A-143 | OCH$_3$ | CH$_3$ | CH$_3$ | benzyl |
| A-144 | OCF$_3$ | CH$_3$ | CH$_3$ | benzyl |
| A-145 | H | H | | —(CH$_2$)$_3$— |
| A-146 | F | H | | —(CH$_2$)$_3$— |
| A-147 | Cl | H | | —(CH$_2$)$_3$— |
| A-148 | Br | H | | —(CH$_2$)$_3$— |
| A-149 | CH$_3$ | H | | —(CH$_2$)$_3$— |
| A-150 | CF$_3$ | H | | —(CH$_2$)$_3$— |
| A-151 | OCH$_3$ | H | | —(CH$_2$)$_3$— |
| A-152 | OCF$_3$ | H | | —(CH$_2$)$_3$— |
| A-153 | H | CH$_3$ | | —(CH$_2$)$_3$— |
| A-154 | F | CH$_3$ | | —(CH$_2$)$_3$— |
| A-155 | Cl | CH$_3$ | | —(CH$_2$)$_3$— |
| A-156 | Br | CH$_3$ | | —(CH$_2$)$_3$— |
| A-157 | CH$_3$ | CH$_3$ | | —(CH$_2$)$_3$— |
| A-158 | CF$_3$ | CH$_3$ | | —(CH$_2$)$_3$— |

TABLE A-continued

| No. | R$^{9a}$ | R$^{5b}$ | R$^{5a}$ | R$^6$ |
|---|---|---|---|---|
| A-159 | OCH$_3$ | CH$_3$ | | —(CH$_2$)$_3$— |
| A-160 | OCF$_3$ | CH$_3$ | | —(CH$_2$)$_3$— |
| A-161 | H | D | | —(CH$_2$)$_3$— |
| A-162 | F | D | | —(CH$_2$)$_3$— |
| A-163 | Cl | D | | —(CH$_2$)$_3$— |
| A-164 | Br | D | | —(CH$_2$)$_3$— |
| A-165 | CH$_3$ | D | | —(CH$_2$)$_3$— |
| A-166 | CF$_3$ | D | | —(CH$_2$)$_3$— |
| A-167 | OCH$_3$ | D | | —(CH$_2$)$_3$— |
| A-168 | OCF$_3$ | D | | —(CH$_2$)$_3$— |
| A-169 | H | H | | —(CH$_2$)$_4$— |
| A-170 | F | H | | —(CH$_2$)$_4$— |
| A-171 | Cl | H | | —(CH$_2$)$_4$— |
| A-172 | Br | H | | —(CH$_2$)$_4$— |
| A-173 | CH$_3$ | H | | —(CH$_2$)$_4$— |
| A-174 | CF$_3$ | H | | —(CH$_2$)$_4$— |
| A-175 | OCH$_3$ | H | | —(CH$_2$)$_4$— |
| A-176 | OCF$_3$ | H | | —(CH$_2$)$_4$— |
| A-177 | H | CH$_3$ | | —(CH$_2$)$_4$— |
| A-178 | F | CH$_3$ | | —(CH$_2$)$_4$— |
| A-179 | Cl | CH$_3$ | | —(CH$_2$)$_4$— |
| A-180 | Br | CH$_3$ | | —(CH$_2$)$_4$— |
| A-181 | CH$_3$ | CH$_3$ | | —(CH$_2$)$_4$— |
| A-182 | CF$_3$ | CH$_3$ | | —(CH$_2$)$_4$— |
| A-183 | OCH$_3$ | CH$_3$ | | —(CH$_2$)$_4$— |
| A-184 | OCF$_3$ | CH$_3$ | | —(CH$_2$)$_4$— |
| A-185 | H | D | | —(CH$_2$)$_4$— |
| A-186 | F | D | | —(CH$_2$)$_4$— |
| A-187 | Cl | D | | —(CH$_2$)$_4$— |
| A-188 | Br | D | | —(CH$_2$)$_4$— |
| A-189 | CH$_3$ | D | | —(CH$_2$)$_4$— |
| A-190 | CF$_3$ | D | | —(CH$_2$)$_4$— |
| A-191 | OCH$_3$ | D | | —(CH$_2$)$_4$— |
| A-192 | OCF$_3$ | D | | —(CH$_2$)$_4$— |
| A-193 | H | H | | —(CH$_2$)$_5$— |
| A-194 | F | H | | —(CH$_2$)$_5$— |
| A-195 | Cl | H | | —(CH$_2$)$_5$— |
| A-196 | Br | H | | —(CH$_2$)$_5$— |
| A-197 | CH$_3$ | H | | —(CH$_2$)$_5$— |
| A-198 | CF$_3$ | H | | —(CH$_2$)$_5$— |
| A-199 | OCH$_3$ | H | | —(CH$_2$)$_5$— |
| A-200 | OCF$_3$ | H | | —(CH$_2$)$_5$— |
| A-201 | H | CH$_3$ | | —(CH$_2$)$_5$— |
| A-202 | F | CH$_3$ | | —(CH$_2$)$_5$— |
| A-203 | Cl | CH$_3$ | | —(CH$_2$)$_5$— |
| A-204 | Br | CH$_3$ | | —(CH$_2$)$_5$— |
| A-205 | CH$_3$ | CH$_3$ | | —(CH$_2$)$_5$— |
| A-206 | CF$_3$ | CH$_3$ | | —(CH$_2$)$_5$— |
| A-207 | OCH$_3$ | CH$_3$ | | —(CH$_2$)$_5$— |
| A-208 | OCF$_3$ | CH$_3$ | | —(CH$_2$)$_5$— |
| A-209 | H | D | | —(CH$_2$)$_5$— |
| A-210 | F | D | | —(CH$_2$)$_5$— |
| A-211 | Cl | D | | —(CH$_2$)$_5$— |
| A-212 | Br | D | | —(CH$_2$)$_5$— |
| A-213 | CH$_3$ | D | | —(CH$_2$)$_5$— |
| A-214 | CF$_3$ | D | | —(CH$_2$)$_5$— |
| A-215 | OCH$_3$ | D | | —(CH$_2$)$_5$— |
| A-216 | OCF$_3$ | D | | —(CH$_2$)$_5$— |

*C$_6$H$_5$ = phenyl
**C$_6$H$_4$CH$_3$ = 4-methylphenyl (p-tolyl)

TABLE B

| No. | R$^{9a}$ | R$^{5b}$ | R$^{5a}$ | R$^7$ | R$^8$ |
|---|---|---|---|---|---|
| B-1 | H | H | H | CH$_3$ | CH$_3$ |
| B-2 | F | H | H | CH$_3$ | CH$_3$ |
| B-3 | Cl | H | H | CH$_3$ | CH$_3$ |
| B-4 | Br | H | H | CH$_3$ | CH$_3$ |
| B-5 | CH$_3$ | H | H | CH$_3$ | CH$_3$ |
| B-6 | CF$_3$ | H | H | CH$_3$ | CH$_3$ |
| B-7 | OCH$_3$ | H | H | CH$_3$ | CH$_3$ |
| B-8 | OCF$_3$ | H | H | CH$_3$ | CH$_3$ |
| B-9 | H | F | H | CH$_3$ | CH$_3$ |
| B-10 | F | F | H | CH$_3$ | CH$_3$ |
| B-11 | Cl | F | H | CH$_3$ | CH$_3$ |
| B-12 | Br | F | H | CH$_3$ | CH$_3$ |
| B-13 | CH$_3$ | F | H | CH$_3$ | CH$_3$ |
| B-14 | CF$_3$ | F | H | CH$_3$ | CH$_3$ |
| B-15 | OCH$_3$ | F | H | CH$_3$ | CH$_3$ |
| B-16 | OCF$_3$ | F | H | CH$_3$ | CH$_3$ |
| B-17 | H | Cl | H | CH$_3$ | CH$_3$ |
| B-18 | F | Cl | H | CH$_3$ | CH$_3$ |
| B-19 | Cl | Cl | H | CH$_3$ | CH$_3$ |
| B-20 | Br | Cl | H | CH$_3$ | CH$_3$ |
| B-21 | CH$_3$ | Cl | H | CH$_3$ | CH$_3$ |
| B-22 | CF$_3$ | Cl | H | CH$_3$ | CH$_3$ |
| B-23 | OCH$_3$ | Cl | H | CH$_3$ | CH$_3$ |
| B-24 | OCF$_3$ | Cl | H | CH$_3$ | CH$_3$ |
| B-25 | H | CH$_3$ | H | CH$_3$ | CH$_3$ |
| B-26 | F | CH$_3$ | H | CH$_3$ | CH$_3$ |
| B-27 | Cl | CH$_3$ | H | CH$_3$ | CH$_3$ |
| B-28 | Br | CH$_3$ | H | CH$_3$ | CH$_3$ |
| B-29 | CH$_3$ | CH$_3$ | H | CH$_3$ | CH$_3$ |
| B-30 | CF$_3$ | CH$_3$ | H | CH$_3$ | CH$_3$ |
| B-31 | OCH$_3$ | CH$_3$ | H | CH$_3$ | CH$_3$ |
| B-32 | OCF$_3$ | CH$_3$ | H | CH$_3$ | CH$_3$ |
| B-33 | H | CH$_3$ | CH$_3$ | CH$_3$ | CH$_3$ |
| B-34 | F | CH$_3$ | CH$_3$ | CH$_3$ | CH$_3$ |
| B-35 | Cl | CH$_3$ | CH$_3$ | CH$_3$ | CH$_3$ |
| B-36 | Br | CH$_3$ | CH$_3$ | CH$_3$ | CH$_3$ |
| B-37 | CH$_3$ | CH$_3$ | CH$_3$ | CH$_3$ | CH$_3$ |
| B-38 | CF$_3$ | CH$_3$ | CH$_3$ | CH$_3$ | CH$_3$ |
| B-39 | OCH$_3$ | CH$_3$ | CH$_3$ | CH$_3$ | CH$_3$ |
| B-40 | OCF$_3$ | CH$_3$ | CH$_3$ | CH$_3$ | CH$_3$ |
| B-41 | H | H | H | CH$_3$ | CH$_2$CH$_3$ |
| B-42 | F | H | H | CH$_3$ | CH$_2$CH$_3$ |
| B-43 | Cl | H | H | CH$_3$ | CH$_2$CH$_3$ |
| B-44 | Br | H | H | CH$_3$ | CH$_2$CH$_3$ |
| B-45 | CH$_3$ | H | H | CH$_3$ | CH$_2$CH$_3$ |
| B-46 | CF$_3$ | H | H | CH$_3$ | CH$_2$CH$_3$ |
| B-47 | OCH$_3$ | H | H | CH$_3$ | CH$_2$CH$_3$ |
| B-48 | OCF$_3$ | H | H | CH$_3$ | CH$_2$CH$_3$ |
| B-49 | H | F | H | CH$_3$ | CH$_2$CH$_3$ |
| B-50 | F | F | H | CH$_3$ | CH$_2$CH$_3$ |
| B-51 | Cl | F | H | CH$_3$ | CH$_2$CH$_3$ |
| B-52 | Br | F | H | CH$_3$ | CH$_2$CH$_3$ |
| B-53 | CH$_3$ | F | H | CH$_3$ | CH$_2$CH$_3$ |
| B-54 | CF$_3$ | F | H | CH$_3$ | CH$_2$CH$_3$ |
| B-55 | OCH$_3$ | F | H | CH$_3$ | CH$_2$CH$_3$ |
| B-56 | OCF$_3$ | F | H | CH$_3$ | CH$_2$CH$_3$ |
| B-57 | H | Cl | H | CH$_3$ | CH$_2$CH$_3$ |
| B-58 | F | Cl | H | CH$_3$ | CH$_2$CH$_3$ |
| B-59 | Cl | Cl | H | CH$_3$ | CH$_2$CH$_3$ |
| B-60 | Br | Cl | H | CH$_3$ | CH$_2$CH$_3$ |
| B-61 | CH$_3$ | Cl | H | CH$_3$ | CH$_2$CH$_3$ |
| B-62 | CF$_3$ | Cl | H | CH$_3$ | CH$_2$CH$_3$ |
| B-63 | OCH$_3$ | Cl | H | CH$_3$ | CH$_2$CH$_3$ |
| B-64 | OCF$_3$ | Cl | H | CH$_3$ | CH$_2$CH$_3$ |
| B-65 | H | CH$_3$ | H | CH$_3$ | CH$_2$CH$_3$ |
| B-66 | F | CH$_3$ | H | CH$_3$ | CH$_2$CH$_3$ |
| B-67 | Cl | CH$_3$ | H | CH$_3$ | CH$_2$CH$_3$ |
| B-68 | Br | CH$_3$ | H | CH$_3$ | CH$_2$CH$_3$ |
| B-69 | CH$_3$ | CH$_3$ | H | CH$_3$ | CH$_2$CH$_3$ |
| B-70 | CF$_3$ | CH$_3$ | H | CH$_3$ | CH$_2$CH$_3$ |
| B-71 | OCH$_3$ | CH$_3$ | H | CH$_3$ | CH$_2$CH$_3$ |
| B-72 | OCF$_3$ | CH$_3$ | H | CH$_3$ | CH$_2$CH$_3$ |
| B-73 | H | CH$_3$ | CH$_3$ | CH$_3$ | CH$_2$CH$_3$ |
| B-74 | F | CH$_3$ | CH$_3$ | CH$_3$ | CH$_2$CH$_3$ |
| B-75 | Cl | CH$_3$ | CH$_3$ | CH$_3$ | CH$_2$CH$_3$ |
| B-76 | Br | CH$_3$ | CH$_3$ | CH$_3$ | CH$_2$CH$_3$ |
| B-77 | CH$_3$ | CH$_3$ | CH$_3$ | CH$_3$ | CH$_2$CH$_3$ |
| B-78 | CF$_3$ | CH$_3$ | CH$_3$ | CH$_3$ | CH$_2$CH$_3$ |
| B-79 | OCH$_3$ | CH$_3$ | CH$_3$ | CH$_3$ | CH$_2$CH$_3$ |
| B-80 | OCF$_3$ | CH$_3$ | CH$_3$ | CH$_3$ | CH$_2$CH$_3$ |
| B-81 | H | H | H | CH$_3$ | CF$_3$ |
| B-82 | F | H | H | CH$_3$ | CF$_3$ |
| B-83 | Cl | H | H | CH$_3$ | CF$_3$ |
| B-84 | Br | H | H | CH$_3$ | CF$_3$ |
| B-85 | CH$_3$ | H | H | CH$_3$ | CF$_3$ |
| B-86 | CF$_3$ | H | H | CH$_3$ | CF$_3$ |
| B-87 | OCH$_3$ | H | H | CH$_3$ | CF$_3$ |
| B-88 | OCF$_3$ | H | H | CH$_3$ | CF$_3$ |

TABLE B-continued

| No. | $R^{9a}$ | $R^{5b}$ | $R^{5a}$ | $R^7$ | $R^8$ |
|---|---|---|---|---|---|
| B-89 | H | F | H | $CH_3$ | $CF_3$ |
| B-90 | F | F | H | $CH_3$ | $CF_3$ |
| B-91 | Cl | F | H | $CH_3$ | $CF_3$ |
| B-92 | Br | F | H | $CH_3$ | $CF_3$ |
| B-93 | $CH_3$ | F | H | $CH_3$ | $CF_3$ |
| B-94 | $CF_3$ | F | H | $CH_3$ | $CF_3$ |
| B-95 | $OCH_3$ | F | H | $CH_3$ | $CF_3$ |
| B-96 | $OCF_3$ | F | H | $CH_3$ | $CF_3$ |
| B-97 | H | Cl | H | $CH_3$ | $CF_3$ |
| B-98 | F | Cl | H | $CH_3$ | $CF_3$ |
| B-99 | Cl | Cl | H | $CH_3$ | $CF_3$ |
| B-100 | Br | Cl | H | $CH_3$ | $CF_3$ |
| B-101 | $CH_3$ | Cl | H | $CH_3$ | $CF_3$ |
| B-102 | $CF_3$ | Cl | H | $CH_3$ | $CF_3$ |
| B-103 | $OCH_3$ | Cl | H | $CH_3$ | $CF_3$ |
| B-104 | $OCF_3$ | Cl | H | $CH_3$ | $CF_3$ |
| B-105 | H | $CH_3$ | H | $CH_3$ | $CF_3$ |
| B-106 | F | $CH_3$ | H | $CH_3$ | $CF_3$ |
| B-107 | Cl | $CH_3$ | H | $CH_3$ | $CF_3$ |
| B-108 | Br | $CH_3$ | H | $CH_3$ | $CF_3$ |
| B-109 | $CH_3$ | $CH_3$ | H | $CH_3$ | $CF_3$ |
| B-110 | $CF_3$ | $CH_3$ | H | $CH_3$ | $CF_3$ |
| B-111 | $OCH_3$ | $CH_3$ | H | $CH_3$ | $CF_3$ |
| B-112 | $OCF_3$ | $CH_3$ | H | $CH_3$ | $CF_3$ |
| B-113 | H | $CH_3$ | $CH_3$ | $CH_3$ | $CF_3$ |
| B-114 | F | $CH_3$ | $CH_3$ | $CH_3$ | $CF_3$ |
| B-115 | Cl | $CH_3$ | $CH_3$ | $CH_3$ | $CF_3$ |
| B-116 | Br | $CH_3$ | $CH_3$ | $CH_3$ | $CF_3$ |
| B-117 | $CH_3$ | $CH_3$ | $CH_3$ | $CH_3$ | $CF_3$ |
| B-118 | $CF_3$ | $CH_3$ | $CH_3$ | $CH_3$ | $CF_3$ |
| B-119 | $OCH_3$ | $CH_3$ | $CH_3$ | $CH_3$ | $CF_3$ |
| B-120 | $OCF_3$ | $CH_3$ | $CH_3$ | $CH_3$ | $CF_3$ |
| B-121 | H | H | H | $CF_3$ | $CF_3$ |
| B-122 | F | H | H | $CF_3$ | $CF_3$ |
| B-123 | Cl | H | H | $CF_3$ | $CF_3$ |
| B-124 | Br | H | H | $CF_3$ | $CF_3$ |
| B-125 | $CH_3$ | H | H | $CF_3$ | $CF_3$ |
| B-126 | $CF_3$ | H | H | $CF_3$ | $CF_3$ |
| B-127 | $OCH_3$ | H | H | $CF_3$ | $CF_3$ |
| B-128 | $OCF_3$ | H | H | $CF_3$ | $CF_3$ |
| B-129 | H | F | H | $CF_3$ | $CF_3$ |
| B-130 | F | F | H | $CF_3$ | $CF_3$ |
| B-131 | Cl | F | H | $CF_3$ | $CF_3$ |
| B-132 | Br | F | H | $CF_3$ | $CF_3$ |
| B-133 | $CH_3$ | F | H | $CF_3$ | $CF_3$ |
| B-134 | $CF_3$ | F | H | $CF_3$ | $CF_3$ |
| B-135 | $OCH_3$ | F | H | $CF_3$ | $CF_3$ |
| B-136 | $OCF_3$ | F | H | $CF_3$ | $CF_3$ |
| B-137 | H | Cl | H | $CF_3$ | $CF_3$ |
| B-138 | F | Cl | H | $CF_3$ | $CF_3$ |
| B-139 | Cl | Cl | H | $CF_3$ | $CF_3$ |
| B-140 | Br | Cl | H | $CF_3$ | $CF_3$ |
| B-141 | $CH_3$ | Cl | H | $CF_3$ | $CF_3$ |
| B-142 | $CF_3$ | Cl | H | $CF_3$ | $CF_3$ |
| B-143 | $OCH_3$ | Cl | H | $CF_3$ | $CF_3$ |
| B-144 | $OCF_3$ | Cl | H | $CF_3$ | $CF_3$ |
| B-145 | H | $CH_3$ | H | $CF_3$ | $CF_3$ |
| B-146 | F | $CH_3$ | H | $CF_3$ | $CF_3$ |
| B-147 | Cl | $CH_3$ | H | $CF_3$ | $CF_3$ |
| B-148 | Br | $CH_3$ | H | $CF_3$ | $CF_3$ |
| B-149 | $CH_3$ | $CH_3$ | H | $CF_3$ | $CF_3$ |
| B-150 | $CF_3$ | $CH_3$ | H | $CF_3$ | $CF_3$ |
| B-151 | $OCH_3$ | $CH_3$ | H | $CF_3$ | $CF_3$ |
| B-152 | $OCF_3$ | $CH_3$ | H | $CF_3$ | $CF_3$ |
| B-153 | H | $CH_3$ | $CH_3$ | $CF_3$ | $CF_3$ |
| B-154 | F | $CH_3$ | $CH_3$ | $CF_3$ | $CF_3$ |
| B-155 | Cl | $CH_3$ | $CH_3$ | $CF_3$ | $CF_3$ |
| B-156 | Br | $CH_3$ | $CH_3$ | $CF_3$ | $CF_3$ |
| B-157 | $CH_3$ | $CH_3$ | $CH_3$ | $CF_3$ | $CF_3$ |
| B-158 | $CF_3$ | $CH_3$ | $CH_3$ | $CF_3$ | $CF_3$ |
| B-159 | $OCH_3$ | $CH_3$ | $CH_3$ | $CF_3$ | $CF_3$ |
| B-160 | $OCF_3$ | $CH_3$ | $CH_3$ | $CF_3$ | $CF_3$ |
| B-161 | H | H | H | $CH_3$ | $C_6H_5$* |
| B-162 | F | H | H | $CH_3$ | $C_6H_5$ |
| B-163 | Cl | H | H | $CH_3$ | $C_6H_5$ |
| B-164 | Br | H | H | $CH_3$ | $C_6H_5$ |
| B-165 | $CH_3$ | H | H | $CH_3$ | $C_6H_5$ |
| B-166 | $CF_3$ | H | H | $CH_3$ | $C_6H_5$ |
| B-167 | $OCH_3$ | H | H | $CH_3$ | $C_6H_5$ |
| B-168 | $OCF_3$ | H | H | $CH_3$ | $C_6H_5$ |
| B-169 | H | F | H | $CH_3$ | $C_6H_5$ |
| B-170 | F | F | H | $CH_3$ | $C_6H_5$ |
| B-171 | Cl | F | H | $CH_3$ | $C_6H_5$ |
| B-172 | Br | F | H | $CH_3$ | $C_6H_5$ |
| B-173 | $CH_3$ | F | H | $CH_3$ | $C_6H_5$ |
| B-174 | $CF_3$ | F | H | $CH_3$ | $C_6H_5$ |
| B-175 | $OCH_3$ | F | H | $CH_3$ | $C_6H_5$ |
| B-176 | $OCF_3$ | F | H | $CH_3$ | $C_6H_5$ |
| B-177 | H | Cl | H | $CH_3$ | $C_6H_5$ |
| B-178 | F | Cl | H | $CH_3$ | $C_6H_5$ |
| B-179 | Cl | Cl | H | $CH_3$ | $C_6H_5$ |
| B-180 | Br | Cl | H | $CH_3$ | $C_6H_5$ |
| B-181 | $CH_3$ | Cl | H | $CH_3$ | $C_6H_5$ |
| B-182 | $CF_3$ | Cl | H | $CH_3$ | $C_6H_5$ |
| B-183 | $OCH_3$ | Cl | H | $CH_3$ | $C_6H_5$ |
| B-184 | $OCF_3$ | Cl | H | $CH_3$ | $C_6H_5$ |
| B-185 | H | $CH_3$ | H | $CH_3$ | $C_6H_5$ |
| B-186 | F | $CH_3$ | H | $CH_3$ | $C_6H_5$ |
| B-187 | Cl | $CH_3$ | H | $CH_3$ | $C_6H_5$ |
| B-188 | Br | $CH_3$ | H | $CH_3$ | $C_6H_5$ |
| B-189 | $CH_3$ | $CH_3$ | H | $CH_3$ | $C_6H_5$ |
| B-190 | $CF_3$ | $CH_3$ | H | $CH_3$ | $C_6H_5$ |
| B-191 | $OCH_3$ | $CH_3$ | H | $CH_3$ | $C_6H_5$ |
| B-192 | $OCF_3$ | $CH_3$ | H | $CH_3$ | $C_6H_5$ |
| B-193 | H | $CH_3$ | $CH_3$ | $CH_3$ | $C_6H_5$ |
| B-194 | F | $CH_3$ | $CH_3$ | $CH_3$ | $C_6H_5$ |
| B-195 | Cl | $CH_3$ | $CH_3$ | $CH_3$ | $C_6H_5$ |
| B-196 | Br | $CH_3$ | $CH_3$ | $CH_3$ | $C_6H_5$ |
| B-197 | $CH_3$ | $CH_3$ | $CH_3$ | $CH_3$ | $C_6H_5$ |
| B-198 | $CF_3$ | $CH_3$ | $CH_3$ | $CH_3$ | $C_6H_5$ |
| B-199 | $OCH_3$ | $CH_3$ | $CH_3$ | $CH_3$ | $C_6H_5$ |
| B-200 | $OCF_3$ | $CH_3$ | $CH_3$ | $CH_3$ | $C_6H_5$ |
| B-201 | H | H | H | —$(CH_2)_2$— | |
| B-202 | F | H | H | —$(CH_2)_2$— | |
| B-203 | Cl | H | H | —$(CH_2)_2$— | |
| B-204 | Br | H | H | —$(CH_2)_2$— | |
| B-205 | $CH_3$ | H | H | —$(CH_2)_2$— | |
| B-206 | $CF_3$ | H | H | —$(CH_2)_2$— | |
| B-207 | $OCH_3$ | H | H | —$(CH_2)_2$— | |
| B-208 | $OCF_3$ | H | H | —$(CH_2)_2$— | |
| B-209 | H | F | H | —$(CH_2)_2$— | |
| B-210 | F | F | H | —$(CH_2)_2$— | |
| B-211 | Cl | F | H | —$(CH_2)_2$— | |
| B-212 | Br | F | H | —$(CH_2)_2$— | |
| B-213 | $CH_3$ | F | H | —$(CH_2)_2$— | |
| B-214 | $CF_3$ | F | H | —$(CH_2)_2$— | |
| B-215 | $OCH_3$ | F | H | —$(CH_2)_2$— | |
| B-216 | $OCF_3$ | F | H | —$(CH_2)_2$— | |
| B-217 | H | Cl | H | —$(CH_2)_2$— | |
| B-218 | F | Cl | H | —$(CH_2)_2$— | |
| B-219 | Cl | Cl | H | —$(CH_2)_2$— | |
| B-220 | Br | Cl | H | —$(CH_2)_2$— | |
| B-221 | $CH_3$ | Cl | H | —$(CH_2)_2$— | |
| B-222 | $CF_3$ | Cl | H | —$(CH_2)_2$— | |
| B-223 | $OCH_3$ | Cl | H | —$(CH_2)_2$— | |
| B-224 | $OCF_3$ | Cl | H | —$(CH_2)_2$— | |
| B-225 | H | $CH_3$ | H | —$(CH_2)_2$— | |
| B-226 | F | $CH_3$ | H | —$(CH_2)_2$— | |
| B-227 | Cl | $CH_3$ | H | —$(CH_2)_2$— | |
| B-228 | Br | $CH_3$ | H | —$(CH_2)_2$— | |
| B-229 | $CH_3$ | $CH_3$ | H | —$(CH_2)_2$— | |
| B-230 | $CF_3$ | $CH_3$ | H | —$(CH_2)_2$— | |
| B-231 | $OCH_3$ | $CH_3$ | H | —$(CH_2)_2$— | |
| B-232 | $OCF_3$ | $CH_3$ | H | —$(CH_2)_2$— | |
| B-233 | H | $CH_3$ | $CH_3$ | —$(CH_2)_2$— | |
| B-234 | F | $CH_3$ | $CH_3$ | —$(CH_2)_2$— | |
| B-235 | Cl | $CH_3$ | $CH_3$ | —$(CH_2)_2$— | |
| B-236 | Br | $CH_3$ | $CH_3$ | —$(CH_2)_2$— | |
| B-237 | $CH_3$ | $CH_3$ | $CH_3$ | —$(CH_2)_2$— | |
| B-238 | $CF_3$ | $CH_3$ | $CH_3$ | —$(CH_2)_2$— | |
| B-239 | $OCH_3$ | $CH_3$ | $CH_3$ | —$(CH_2)_2$— | |
| B-240 | $OCF_3$ | $CH_3$ | $CH_3$ | —$(CH_2)_2$— | |
| B-241 | H | H | H | —$(CH_2)_3$— | |
| B-242 | F | H | H | —$(CH_2)_3$— | |
| B-243 | Cl | H | H | —$(CH_2)_3$— | |
| B-244 | Br | H | H | —$(CH_2)_3$— | |

TABLE B-continued

| No. | R⁹ᵃ | R⁵ᵇ | R⁵ᵃ | R⁷ | R⁸ |
|---|---|---|---|---|---|
| B-245 | $CH_3$ | H | H | | —$(CH_2)_3$— |
| B-246 | $CF_3$ | H | H | | —$(CH_2)_3$— |
| B-247 | $OCH_3$ | H | H | | —$(CH_2)_3$— |
| B-248 | $OCF_3$ | H | H | | —$(CH_2)_3$— |
| B-249 | H | F | H | | —$(CH_2)_3$— |
| B-250 | F | F | H | | —$(CH_2)_3$— |
| B-251 | Cl | F | H | | —$(CH_2)_3$— |
| B-252 | Br | F | H | | —$(CH_2)_3$— |
| B-253 | $CH_3$ | F | H | | —$(CH_2)_3$— |
| B-254 | $CF_3$ | F | H | | —$(CH_2)_3$— |
| B-255 | $OCH_3$ | F | H | | —$(CH_2)_3$— |
| B-256 | $OCF_3$ | F | H | | —$(CH_2)_3$— |
| B-257 | H | Cl | H | | —$(CH_2)_3$— |
| B-258 | F | Cl | H | | —$(CH_2)_3$— |
| B-259 | Cl | Cl | H | | —$(CH_2)_3$— |
| B-260 | Br | Cl | H | | —$(CH_2)_3$— |
| B-261 | $CH_3$ | Cl | H | | —$(CH_2)_3$— |
| B-262 | $CF_3$ | Cl | H | | —$(CH_2)_3$— |
| B-263 | $OCH_3$ | Cl | H | | —$(CH_2)_3$— |
| B-264 | $OCF_3$ | Cl | H | | —$(CH_2)_3$— |
| B-265 | H | $CH_3$ | H | | —$(CH_2)_3$— |
| B-266 | F | $CH_3$ | H | | —$(CH_2)_3$— |
| B-267 | Cl | $CH_3$ | H | | —$(CH_2)_3$— |
| B-268 | Br | $CH_3$ | H | | —$(CH_2)_3$— |
| B-269 | $CH_3$ | $CH_3$ | H | | —$(CH_2)_3$— |
| B-270 | $CF_3$ | $CH_3$ | H | | —$(CH_2)_3$— |
| B-271 | $OCH_3$ | $CH_3$ | H | | —$(CH_2)_3$— |
| B-272 | $OCF_3$ | $CH_3$ | H | | —$(CH_2)_3$— |
| B-273 | H | $CH_3$ | $CH_3$ | | —$(CH_2)_3$— |
| B-274 | F | $CH_3$ | $CH_3$ | | —$(CH_2)_3$— |
| B-275 | Cl | $CH_3$ | $CH_3$ | | —$(CH_2)_3$— |
| B-276 | Br | $CH_3$ | $CH_3$ | | —$(CH_2)_3$— |
| B-277 | $CH_3$ | $CH_3$ | $CH_3$ | | —$(CH_2)_3$— |
| B-278 | $CF_3$ | $CH_3$ | $CH_3$ | | —$(CH_2)_3$— |
| B-279 | $OCH_3$ | $CH_3$ | $CH_3$ | | —$(CH_2)_3$— |
| B-280 | $OCF_3$ | $CH_3$ | $CH_3$ | | —$(CH_2)_3$— |
| B-281 | H | H | H | | —$(CH_2)_4$— |
| B-282 | F | H | H | | —$(CH_2)_4$— |
| B-283 | Cl | H | H | | —$(CH_2)_4$— |
| B-284 | Br | H | H | | —$(CH_2)_4$— |
| B-285 | $CH_3$ | H | H | | —$(CH_2)_4$— |
| B-286 | $CF_3$ | H | H | | —$(CH_2)_4$— |
| B-287 | $OCH_3$ | H | H | | —$(CH_2)_4$— |
| B-288 | $OCF_3$ | H | H | | —$(CH_2)_4$— |
| B-289 | H | F | H | | —$(CH_2)_4$— |
| B-290 | F | F | H | | —$(CH_2)_4$— |
| B-291 | Cl | F | H | | —$(CH_2)_4$— |
| B-292 | Br | F | H | | —$(CH_2)_4$— |
| B-293 | $CH_3$ | F | H | | —$(CH_2)_4$— |
| B-294 | $CF_3$ | F | H | | —$(CH_2)_4$— |
| B-295 | $OCH_3$ | F | H | | —$(CH_2)_4$— |
| B-296 | $OCF_3$ | F | H | | —$(CH_2)_4$— |
| B-297 | H | Cl | H | | —$(CH_2)_4$— |
| B-298 | F | Cl | H | | —$(CH_2)_4$— |
| B-299 | Cl | Cl | H | | —$(CH_2)_4$— |
| B-300 | Br | Cl | H | | —$(CH_2)_4$— |
| B-301 | $CH_3$ | Cl | H | | —$(CH_2)_4$— |
| B-302 | $CF_3$ | Cl | H | | —$(CH_2)_4$— |
| B-303 | $OCH_3$ | Cl | H | | —$(CH_2)_4$— |
| B-304 | $OCF_3$ | Cl | H | | —$(CH_2)_4$— |
| B-305 | H | $CH_3$ | H | | —$(CH_2)_4$— |
| B-306 | F | $CH_3$ | H | | —$(CH_2)_4$— |
| B-307 | Cl | $CH_3$ | H | | —$(CH_2)_4$— |
| B-308 | Br | $CH_3$ | H | | —$(CH_2)_4$— |
| B-309 | $CH_3$ | $CH_3$ | H | | —$(CH_2)_4$— |
| B-310 | $CF_3$ | $CH_3$ | H | | —$(CH_2)_4$— |
| B-311 | $OCH_3$ | $CH_3$ | H | | —$(CH_2)_4$— |
| B-312 | $OCF_3$ | $CH_3$ | H | | —$(CH_2)_4$— |
| B-313 | H | $CH_3$ | $CH_3$ | | —$(CH_2)_4$— |
| B-314 | F | $CH_3$ | $CH_3$ | | —$(CH_2)_4$— |
| B-315 | Cl | $CH_3$ | $CH_3$ | | —$(CH_2)_4$— |
| B-316 | Br | $CH_3$ | $CH_3$ | | —$(CH_2)_4$— |
| B-317 | $CH_3$ | $CH_3$ | $CH_3$ | | —$(CH_2)_4$— |
| B-318 | $CF_3$ | $CH_3$ | $CH_3$ | | —$(CH_2)_4$— |
| B-319 | $OCH_3$ | $CH_3$ | $CH_3$ | | —$(CH_2)_4$— |
| B-320 | $OCF_3$ | $CH_3$ | $CH_3$ | | —$(CH_2)_4$— |
| B-321 | H | H | H | | —$(CH_2)_5$— |
| B-322 | F | H | H | | —$(CH_2)_5$— |
| B-323 | Cl | H | H | | —$(CH_2)_5$— |
| B-324 | Br | H | H | | —$(CH_2)_5$— |
| B-325 | $CH_3$ | H | H | | —$(CH_2)_5$— |
| B-326 | $CF_3$ | H | H | | —$(CH_2)_5$— |
| B-327 | $OCH_3$ | H | H | | —$(CH_2)_5$— |
| B-328 | $OCF_3$ | H | H | | —$(CH_2)_5$— |
| B-329 | H | F | H | | —$(CH_2)_5$— |
| B-330 | F | F | H | | —$(CH_2)_5$— |
| B-331 | Cl | F | H | | —$(CH_2)_5$— |
| B-332 | Br | F | H | | —$(CH_2)_5$— |
| B-333 | $CH_3$ | F | H | | —$(CH_2)_5$— |
| B-334 | $CF_3$ | F | H | | —$(CH_2)_5$— |
| B-335 | $OCH_3$ | F | H | | —$(CH_2)_5$— |
| B-336 | $OCF_3$ | F | H | | —$(CH_2)_5$— |
| B-337 | H | Cl | H | | —$(CH_2)_5$— |
| B-338 | F | Cl | H | | —$(CH_2)_5$— |
| B-339 | Cl | Cl | H | | —$(CH_2)_5$— |
| B-340 | Br | Cl | H | | —$(CH_2)_5$— |
| B-341 | $CH_3$ | Cl | H | | —$(CH_2)_5$— |
| B-342 | $CF_3$ | Cl | H | | —$(CH_2)_5$— |
| B-343 | $OCH_3$ | Cl | H | | —$(CH_2)_5$— |
| B-344 | $OCF_3$ | Cl | H | | —$(CH_2)_5$— |
| B-345 | H | $CH_3$ | H | | —$(CH_2)_5$— |
| B-346 | F | $CH_3$ | H | | —$(CH_2)_5$— |
| B-347 | Cl | $CH_3$ | H | | —$(CH_2)_5$— |
| B-348 | Br | $CH_3$ | H | | —$(CH_2)_5$— |
| B-349 | $CH_3$ | $CH_3$ | H | | —$(CH_2)_5$— |
| B-350 | $CF_3$ | $CH_3$ | H | | —$(CH_2)_5$— |
| B-351 | $OCH_3$ | $CH_3$ | H | | —$(CH_2)_5$— |
| B-352 | $OCF_3$ | $CH_3$ | H | | —$(CH_2)_5$— |
| B-353 | H | $CH_3$ | $CH_3$ | | —$(CH_2)_5$— |
| B-354 | F | $CH_3$ | $CH_3$ | | —$(CH_2)_5$— |
| B-355 | Cl | $CH_3$ | $CH_3$ | | —$(CH_2)_5$— |
| B-356 | Br | $CH_3$ | $CH_3$ | | —$(CH_2)_5$— |
| B-357 | $CH_3$ | $CH_3$ | $CH_3$ | | —$(CH_2)_5$— |
| B-358 | $CF_3$ | $CH_3$ | $CH_3$ | | —$(CH_2)_5$— |
| B-359 | $OCH_3$ | $CH_3$ | $CH_3$ | | —$(CH_2)_5$— |
| B-360 | $OCF_3$ | $CH_3$ | $CH_3$ | | —$(CH_2)_5$— |
| B-361 | H | H | H | | —$(CH_2)_6$— |
| B-362 | F | H | H | | —$(CH_2)_6$— |
| B-363 | Cl | H | H | | —$(CH_2)_6$— |
| B-364 | Br | H | H | | —$(CH_2)_6$— |
| B-365 | $CH_3$ | H | H | | —$(CH_2)_6$— |
| B-366 | $CF_3$ | H | H | | —$(CH_2)_6$— |
| B-367 | $OCH_3$ | H | H | | —$(CH_2)_6$— |
| B-368 | $OCF_3$ | H | H | | —$(CH_2)_6$— |
| B-369 | H | F | H | | —$(CH_2)_6$— |
| B-370 | F | F | H | | —$(CH_2)_6$— |
| B-371 | Cl | F | H | | —$(CH_2)_6$— |
| B-372 | Br | F | H | | —$(CH_2)_6$— |
| B-373 | $CH_3$ | F | H | | —$(CH_2)_6$— |
| B-374 | $CF_3$ | F | H | | —$(CH_2)_6$— |
| B-375 | $OCH_3$ | F | H | | —$(CH_2)_6$— |
| B-376 | $OCF_3$ | F | H | | —$(CH_2)_6$— |
| B-377 | H | Cl | H | | —$(CH_2)_6$— |
| B-378 | F | Cl | H | | —$(CH_2)_6$— |
| B-379 | Cl | Cl | H | | —$(CH_2)_6$— |
| B-380 | Br | Cl | H | | —$(CH_2)_6$— |
| B-381 | $CH_3$ | Cl | H | | —$(CH_2)_6$— |
| B-382 | $CF_3$ | Cl | H | | —$(CH_2)_6$— |
| B-383 | $OCH_3$ | Cl | H | | —$(CH_2)_6$— |
| B-384 | $OCF_3$ | Cl | H | | —$(CH_2)_6$— |
| B-385 | H | $CH_3$ | H | | —$(CH_2)_6$— |
| B-386 | F | $CH_3$ | H | | —$(CH_2)_6$— |
| B-387 | Cl | $CH_3$ | H | | —$(CH_2)_6$— |
| B-388 | Br | $CH_3$ | H | | —$(CH_2)_6$— |
| B-389 | $CH_3$ | $CH_3$ | H | | —$(CH_2)_6$— |
| B-390 | $CF_3$ | $CH_3$ | H | | —$(CH_2)_6$— |
| B-391 | $OCH_3$ | $CH_3$ | H | | —$(CH_2)_6$— |
| B-392 | $OCF_3$ | $CH_3$ | H | | —$(CH_2)_6$— |
| B-393 | H | $CH_3$ | $CH_3$ | | —$(CH_2)_6$— |
| B-394 | F | $CH_3$ | $CH_3$ | | —$(CH_2)_6$— |
| B-395 | Cl | $CH_3$ | $CH_3$ | | —$(CH_2)_6$— |
| B-396 | Br | $CH_3$ | $CH_3$ | | —$(CH_2)_6$— |
| B-397 | $CH_3$ | $CH_3$ | $CH_3$ | | —$(CH_2)_6$— |
| B-398 | $CF_3$ | $CH_3$ | $CH_3$ | | —$(CH_2)_6$— |
| B-399 | $OCH_3$ | $CH_3$ | $CH_3$ | | —$(CH_2)_6$— |
| B-400 | $OCF_3$ | $CH_3$ | $CH_3$ | | —$(CH_2)_6$— |

TABLE B-continued

| No. | $R^{9a}$ | $R^{5b}$ | $R^{5a}$ | $R^7$ | $R^8$ |
|---|---|---|---|---|---|
| B-401 | H | H | H | —CH=CH—$CH_2$—$CH_2$— | |
| B-402 | F | H | H | —CH=CH—$CH_2$—$CH_2$— | |
| B-403 | Cl | H | H | —CH=CH—$CH_2$—$CH_2$— | |
| B-404 | Br | H | H | —CH=CH—$CH_2$—$CH_2$— | |
| B-405 | $CH_3$ | H | H | —CH=CH—$CH_2$—$CH_2$— | |
| B-406 | $CF_3$ | H | H | —CH=CH—$CH_2$—$CH_2$— | |
| B-407 | $OCH_3$ | H | H | —CH=CH—$CH_2$—$CH_2$— | |
| B-408 | $OCF_3$ | H | H | —CH=CH—$CH_2$—$CH_2$— | |
| B-409 | H | F | H | —CH=CH—$CH_2$—$CH_2$— | |
| B-410 | F | F | H | —CH=CH—$CH_2$—$CH_2$— | |
| B-411 | Cl | F | H | —CH=CH—$CH_2$—$CH_2$— | |
| B-412 | Br | F | H | —CH=CH—$CH_2$—$CH_2$— | |
| B-413 | $CH_3$ | F | H | —CH=CH—$CH_2$—$CH_2$— | |
| B-414 | $CF_3$ | F | H | —CH=CH—$CH_2$—$CH_2$— | |
| B-415 | $OCH_3$ | F | H | —CH=CH—$CH_2$—$CH_2$— | |
| B-416 | $OCF_3$ | F | H | —CH=CH—$CH_2$—$CH_2$— | |
| B-417 | H | Cl | H | —CH=CH—$CH_2$—$CH_2$— | |
| B-418 | F | Cl | H | —CH=CH—$CH_2$—$CH_2$— | |
| B-419 | Cl | Cl | H | —CH=CH—$CH_2$—$CH_2$— | |
| B-420 | Br | Cl | H | —CH=CH—$CH_2$—$CH_2$— | |
| B-421 | $CH_3$ | Cl | H | —CH=CH—$CH_2$—$CH_2$— | |
| B-422 | $CF_3$ | Cl | H | —CH=CH—$CH_2$—$CH_2$— | |
| B-423 | $OCH_3$ | Cl | H | —CH=CH—$CH_2$—$CH_2$— | |
| B-424 | $OCF_3$ | Cl | H | —CH=CH—$CH_2$—$CH_2$— | |
| B-425 | H | $CH_3$ | H | —CH=CH—$CH_2$—$CH_2$— | |
| B-426 | F | $CH_3$ | H | —CH=CH—$CH_2$—$CH_2$— | |
| B-427 | Cl | $CH_3$ | H | —CH=CH—$CH_2$—$CH_2$— | |
| B-428 | Br | $CH_3$ | H | —CH=CH—$CH_2$—$CH_2$— | |
| B-429 | $CH_3$ | $CH_3$ | H | —CH=CH—$CH_2$—$CH_2$— | |
| B-430 | $CF_3$ | $CH_3$ | H | —CH=CH—$CH_2$—$CH_2$— | |
| B-431 | $OCH_3$ | $CH_3$ | H | —CH=CH—$CH_2$—$CH_2$— | |
| B-432 | $OCF_3$ | $CH_3$ | H | —CH=CH—$CH_2$—$CH_2$— | |
| B-433 | H | $CH_3$ | $CH_3$ | —CH=CH—$CH_2$—$CH_2$— | |
| B-434 | F | $CH_3$ | $CH_3$ | —CH=CH—$CH_2$—$CH_2$— | |
| B-435 | Cl | $CH_3$ | $CH_3$ | —CH=CH—$CH_2$—$CH_2$— | |
| B-436 | Br | $CH_3$ | $CH_3$ | —CH=CH—$CH_2$—$CH_2$— | |
| B-437 | $CH_3$ | $CH_3$ | $CH_3$ | —CH=CH—$CH_2$—$CH_2$— | |
| B-438 | $CF_3$ | $CH_3$ | $CH_3$ | —CH=CH—$CH_2$—$CH_2$— | |
| B-439 | $OCH_3$ | $CH_3$ | $CH_3$ | —CH=CH—$CH_2$—$CH_2$— | |
| B-440 | $OCF_3$ | $CH_3$ | $CH_3$ | —CH=CH—$CH_2$—$CH_2$— | |
| B-441 | H | H | | —$(CH_2)_3$— | $CH_3$ |
| B-442 | F | H | | —$(CH_2)_3$— | $CH_3$ |
| B-443 | Cl | H | | —$(CH_2)_3$— | $CH_3$ |
| B-444 | Br | H | | —$(CH_2)_3$— | $CH_3$ |
| B-445 | $CH_3$ | H | | —$(CH_2)_3$— | $CH_3$ |
| B-446 | $CF_3$ | H | | —$(CH_2)_3$— | $CH_3$ |
| B-447 | $OCH_3$ | H | | —$(CH_2)_3$— | $CH_3$ |
| B-448 | $OCF_3$ | H | | —$(CH_2)_3$— | $CH_3$ |
| B-449 | H | D | | —$(CH_2)_3$— | $CH_3$ |
| B-450 | F | D | | —$(CH_2)_3$— | $CH_3$ |
| B-451 | Cl | D | | —$(CH_2)_3$— | $CH_3$ |
| B-452 | Br | D | | —$(CH_2)_3$— | $CH_3$ |
| B-453 | $CH_3$ | D | | —$(CH_2)_3$— | $CH_3$ |
| B-454 | $CF_3$ | D | | —$(CH_2)_3$— | $CH_3$ |
| B-455 | $OCH_3$ | D | | —$(CH_2)_3$— | $CH_3$ |
| B-456 | $OCF_3$ | D | | —$(CH_2)_3$— | $CH_3$ |
| B-457 | H | H | | —$(CH_2)_3$— | D |
| B-458 | F | H | | —$(CH_2)_3$— | D |
| B-459 | Cl | H | | —$(CH_2)_3$— | D |
| B-460 | Br | H | | —$(CH_2)_3$— | D |
| B-461 | $CH_3$ | H | | —$(CH_2)_3$— | D |
| B-462 | $CF_3$ | H | | —$(CH_2)_3$— | D |
| B-463 | $OCH_3$ | H | | —$(CH_2)_3$— | D |
| B-464 | $OCF_3$ | H | | —$(CH_2)_3$— | D |
| B-465 | H | D | | —$(CH_2)_3$— | D |
| B-466 | F | D | | —$(CH_2)_3$— | D |
| B-467 | Cl | D | | —$(CH_2)_3$— | D |
| B-468 | Br | D | | —$(CH_2)_3$— | D |
| B-469 | $CH_3$ | D | | —$(CH_2)_3$— | D |
| B-470 | $CF_3$ | D | | —$(CH_2)_3$— | D |
| B-471 | $OCH_3$ | D | | —$(CH_2)_3$— | D |
| B-472 | $OCF_3$ | D | | —$(CH_2)_3$— | D |
| B-473 | H | H | | —$(CH_2)_4$— | $CH_3$ |
| B-474 | F | H | | —$(CH_2)_4$— | $CH_3$ |
| B-475 | Cl | H | | —$(CH_2)_4$— | $CH_3$ |
| B-476 | Br | H | | —$(CH_2)_4$— | $CH_3$ |
| B-477 | $CH_3$ | H | | —$(CH_2)_4$— | $CH_3$ |
| B-478 | $CF_3$ | H | | —$(CH_2)_4$— | $CH_3$ |
| B-479 | $OCH_3$ | H | | —$(CH_2)_4$— | $CH_3$ |
| B-480 | $OCF_3$ | H | | —$(CH_2)_4$— | $CH_3$ |
| B-481 | H | D | | —$(CH_2)_4$— | $CH_3$ |
| B-482 | F | D | | —$(CH_2)_4$— | $CH_3$ |
| B-483 | Cl | D | | —$(CH_2)_4$— | $CH_3$ |
| B-484 | Br | D | | —$(CH_2)_4$— | $CH_3$ |
| B-485 | $CH_3$ | D | | —$(CH_2)_4$— | $CH_3$ |
| B-486 | $CF_3$ | D | | —$(CH_2)_4$— | $CH_3$ |
| B-487 | $OCH_3$ | D | | —$(CH_2)_4$— | $CH_3$ |
| B-488 | $OCF_3$ | D | | —$(CH_2)_4$— | $CH_3$ |
| B-489 | H | H | | —$(CH_2)_4$— | D |
| B-490 | F | H | | —$(CH_2)_4$— | D |
| B-491 | Cl | H | | —$(CH_2)_4$— | D |
| B-492 | Br | H | | —$(CH_2)_4$— | D |
| B-493 | $CH_3$ | H | | —$(CH_2)_4$— | D |
| B-494 | $CF_3$ | 3H | | —$(CH_2)_4$— | D |
| B-495 | $OCH_3$ | H | | —$(CH_2)_4$— | D |
| B-496 | $OCF_3$ | H | | —$(CH_2)_4$— | D |
| B-497 | H | D | | —$(CH_2)_4$— | D |
| B-498 | F | D | | —$(CH_2)_4$— | D |
| B-499 | Cl | D | | —$(CH_2)_4$— | D |
| B-500 | Br | D | | —$(CH_2)_4$— | D |
| B-501 | $CH_3$ | D | | —$(CH_2)_4$— | D |
| B-502 | $CF_3$ | D | | —$(CH_2)_4$— | D |
| B-503 | $OCH_3$ | D | | —$(CH_2)_4$— | D |
| B-504 | $OCF_3$ | D | | —$(CH_2)_4$— | D |

*$C_6H_5$ = phenyl

The compounds of the present invention can be prepared by using routine techniques familiar to a skilled person. In particular, the compounds of the formula I can be prepared according to the following schemes, wherein the variables, if not stated otherwise, are as defined above.

Compounds of formula I wherein X is $CR^7R^8$ and $R^{5b}$ is H (=compounds I') can be synthesized as described in scheme 1 below. The protected tetrahydrobenzodiazepine or tetrahydroquinoxaline 1, wherein Z is a hydrogen or a halogen atom, such as Cl, Br or I and PG is a common protective group, such as a carbamate, especially boc, is acylated with the acrylic acid derivative 2, wherein LG is an appropriate leaving group, such as Cl or an anhydride or a chloroformate, in the presence of a base, such as triethylamine or Hünig's base, in an organic solvent, such as ether or methylene chloride. Reaction of 3 with a Lewis acid or a Brönstedt acid HA or irradiation with a suitable wavelength commonly derived from a mercury lamp in an adequate solvent, such as acetone or toluene, in a common photoreactor yields cyclization to 4. Reduction of the carbonyl group with common reduction agents like borohydrides such as sodium borohydride or borane-tetrahydrofurane-complex yields 5, which is deprotected using suitable reagents such as strong bases or acids to I', wherein $R^{4a}$ and $R^{4b}$ and $R^{5b}$ are H. Compounds I wherein $R^{4a}$ and $R^{4b}$ form together =O can be obtained by skipping the reduction step to 5 and deprotecting 4.

Scheme 1

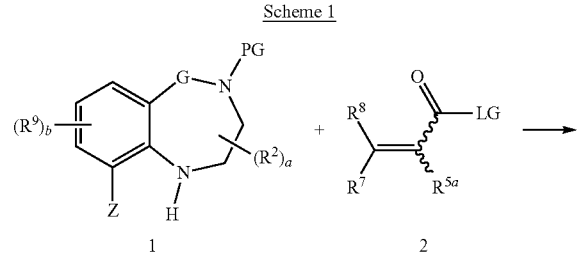

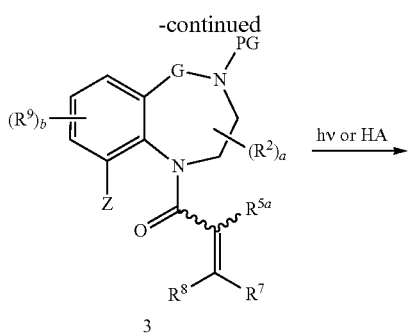

as sodium borohydride or borane-tetrahydrofurane-complex yields 9, which is deprotected using suitable reagents such as strong bases or acids to I'', wherein $R^{4a}$ and $R^{4b}$ are H. Compounds I wherein $R^{4a}$ and $R^{4b}$ form together =O can be obtained by skipping the reduction step to 9 and deprotecting 8. If desired, substituents $R^1$ different from hydrogen can be introduced for example via alkylation under typical conditions such as stirring in an appropriate solvent in the presence of an alkylhalide and a base or via other common substitution reactions.

If desired, substituents $R^1$ different from hydrogen can be introduced for example via alkylation under typical conditions such as stirring in an appropriate solvent in the presence of an alkylhalide and a base or via other common substitution reactions.

Compounds I wherein $R^{5b}$ is different from H can be prepared, for example, by reacting compound 4 with a compound LG-$R^{5b}$ in the presence of a base, wherein LG is an appropriate leaving group, such as Cl or Br.

Compounds I wherein $R^{5b}$ is different from H and $R^8$ is $CH_3$ (=compounds I'') can be prepared, for example, as outlined in scheme 2 below. Acylation of 1 with the allylic acid derivative 6, wherein LG is an appropriate leaving group, such as Cl or an anhydride or a chloroformate, in the presence of a base, such as triethylamine or Hünig's base, in an organic solvent, such as ether or methylene chloride, yields 7, which is reacted in a Heck-type reaction, e.g. employing palladium acetate in the presence of a base, such as potassium carbonate, to yield the cyclization product 8. Reduction of the carbonyl group with common reduction agents like borohydrides such Compounds I wherein X is $NR^6$ (=compounds I''') can be prepared as outlined in scheme 3 below. Acylation of 1 with the β-amino acid derivative 10, wherein PG' is a protection group different from PG and LG is an appropriate leaving group, such as Cl or an anhydride or a chloroformate, in the presence of a base, such as triethylamine or Hünig's base, in an organic solvent, such as ether or methylene chloride, yields 11. This is first selectively deprotected at the amino group $NR^6PG'$. The partially deprotected compound is then reacted in a cyclization reaction to 12 under Buchwald-Hartwig reaction conditions such as the use of a Pd catalyst, e.g. tetrakis(triphenylphosphine) palladium in the presence of as base, such as sodium tert-butylate and potassium carbonate. Reduction of the carbonyl group of 12 with common reduction agents like borohydrides such as sodium borohydride or borane-tetrahydrofurane-complex yields 13, which is deprotected using suitable reagents such as strong bases or acids to I''', wherein $R^{4a}$ and $R^{4b}$ are H. Compounds I wherein $R^{4a}$ and $R^{4b}$ form together =O can be obtained by skipping the reduction step to 13 and deprotecting 12. If desired, substituents $R^1$ different from hydrogen can be introduced for example via alkylation under typical conditions such as stirring in an appropriate solvent in the presence of an alkylhalide and a base or via other common substitution reactions.

Scheme 3

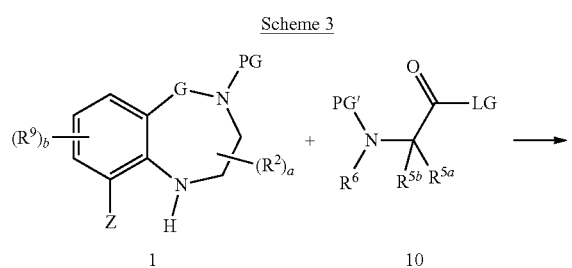

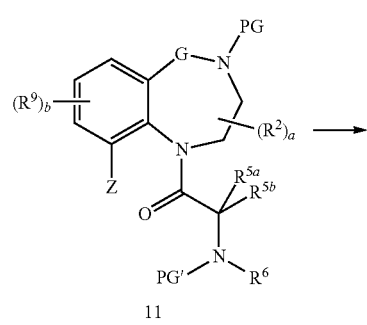

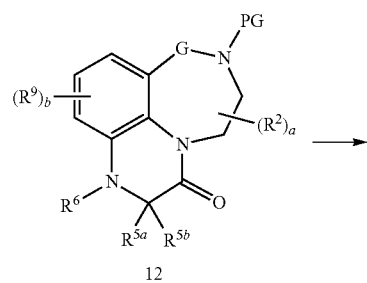

Alternatively to the method depicted in scheme 1, compounds I wherein X is $CR^7R^8$ and $R^{5b}$ is H (=compounds I') can be synthesized as described in scheme 4 below. Readily available anilines 14 are derivatized with carbonyl moieties 15 by acylation procedures employing appropriate leaving groups LG, such as chlorides or anhydrides, in the presence of a base such as triethylamine or Hünig's base, in an organic solvent, such as diethyl ether or methylene chloride to yield 16. Cyclization products 17 are received by irradiation with a suitable wavelength commonly derived from a mercury lamp in an adequate solvent such as acetone or toluene in a common photoreactor known to those skilled in the art. Reduction with common reduction agents like borohydrides such as sodium borohydride or borane-tetrahydrofurane-complex yield suitable intermediates 18 that are alkylated with alkylamides 19 employing suitable leaving groups LG such as chlorides or bromides. After reduction to the corresponding amines 20 cyclization is performed in a suitable solvent like acetonitrile or methanol at room temperature or higher temperature by addition of an acid and substituted ketones or aldehydes to obtain compounds I'.

Scheme 4

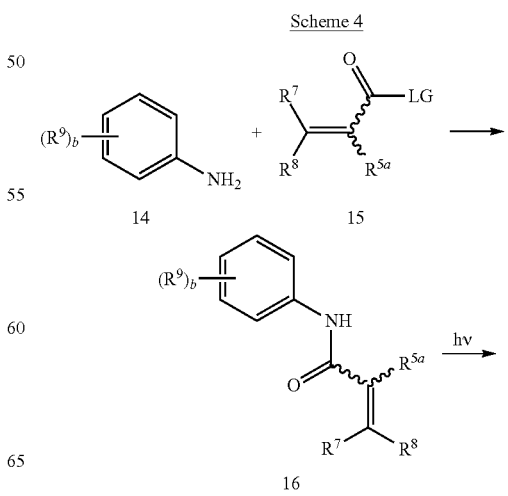

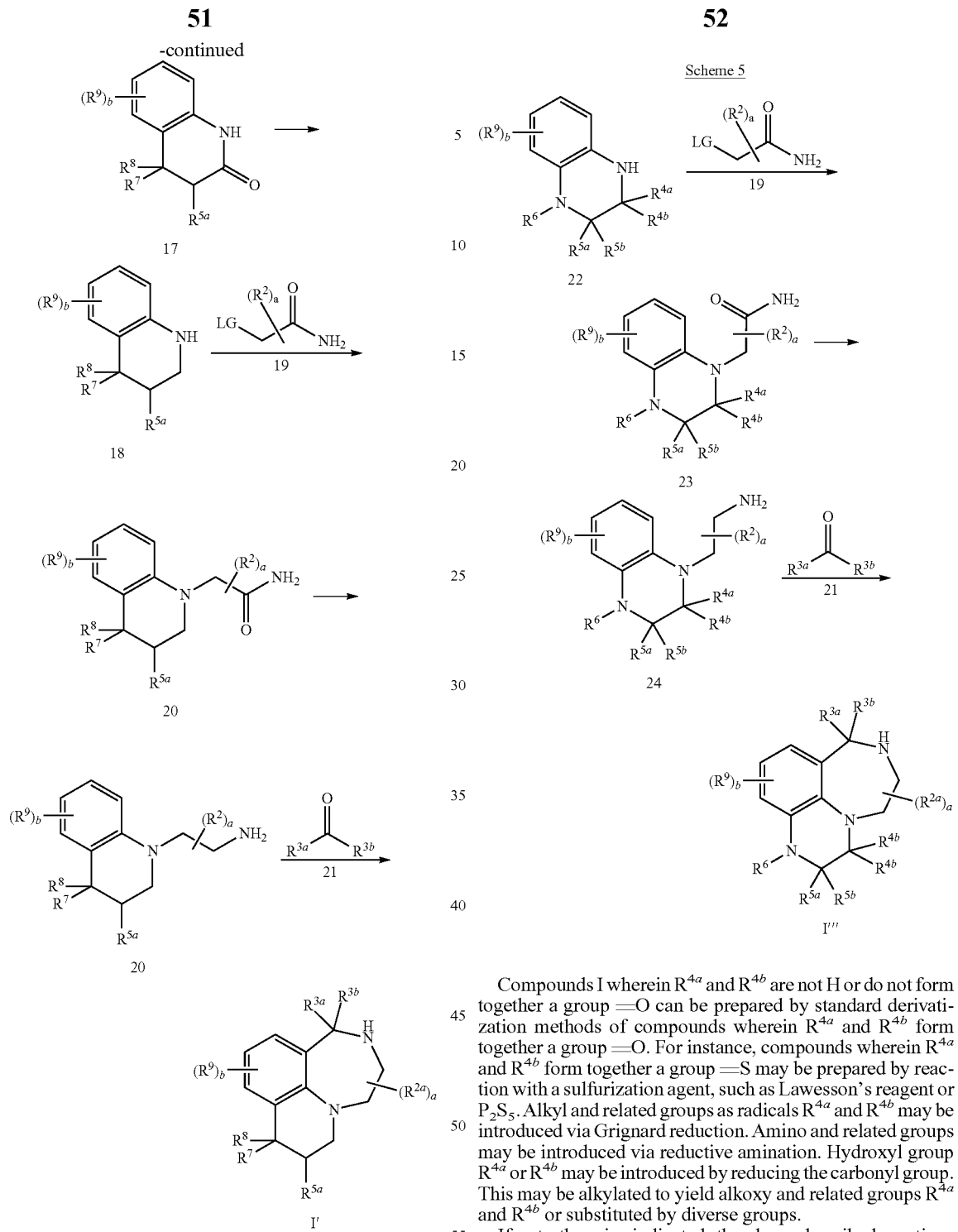

Alternatively to the method depicted in scheme 3, compounds I wherein X is NR$^6$ (=compounds I''') can be prepared as outlined in scheme 5 below.

Readily available starting materials 22 are alkylated with alkylamides 19 employing suitable leaving groups LG such as chlorides or bromides to give 23. After reduction to the corresponding amines 24 cyclization is performed in a suitable solvent like acetonitrile or methanol at room temperature or higher temperature by addition of an acid and substituted ketones or aldehydes 21 to obtain compounds I'''.

Compounds I wherein R$^{4a}$ and R$^{4b}$ are not H or do not form together a group =O can be prepared by standard derivatization methods of compounds wherein R$^{4a}$ and R$^{4b}$ form together a group =O. For instance, compounds wherein R$^{4a}$ and R$^{4b}$ form together a group =S may be prepared by reaction with a sulfurization agent, such as Lawesson's reagent or P$_2$S$_5$. Alkyl and related groups as radicals R$^{4a}$ and R$^{4b}$ may be introduced via Grignard reduction. Amino and related groups may be introduced via reductive amination. Hydroxyl group R$^{4a}$ or R$^{4b}$ may be introduced by reducing the carbonyl group. This may be alkylated to yield alkoxy and related groups R$^{4a}$ and R$^{4b}$ or substituted by diverse groups.

If not otherwise indicated, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The acid addition salts of compounds I are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the preparation methods are within routine techniques.

Suitable protecting groups and the methods for protecting and deprotecting different substituents using such suitable protecting groups are well known to those skilled in the art; examples of which may be found in T. Greene and P. Wuts, Protective Groups in Organic Synthesis ($3^{rd}$ ed.), John Wiley & Sons, NY (1999), which is herein incorporated by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Moreover, the present invention relates to compounds of formula I as defined above, wherein at least one of the atoms has been replaced by its stable, non-radioactive isotope (e.g., hydrogen by deuterium, $^{12}C$ by $^{13}C$, $^{14}N$ by $^{15}N$, $^{16}O$ by $^{18}O$) and preferably wherein at least one hydrogen atom has been replaced by a deuterium atom.

Additionally, the compounds according to the invention include more of the respective isotope than occurs naturally occurs and which is present in compounds I.

Stable isotopes (e.g., deuterium, $^{13}C$, $^{15}N$, $^{18}O$) are nonradioactive isotopes which contain one additional neutron than the normally abundant isotope of the respective atom. Deuterated compounds have been used in pharmaceutical research to investigate the in vivo metabolic fate of the compounds by evaluation of the mechanism of action and metabolic pathway of the non deuterated parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36 (10):927-932 (1995); Kushner et al., *Can. J. Physiol. Pharmacol.*, 77, 79-88 (1999).

Incorporation of a heavy atom, particularly substitution of deuterium for hydrogen, can give rise to an isotope effect that could alter the pharmacokinetics of the drug.

Stable isotope labeling of a drug can alter its physicochemical properties such as $pK_a$ and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5 (4 Suppl): 573; Rodewald L E et al., J. Pediatr. 1989 114: 885; Butte N F et al. Br. J. Nutr. 1991 65: 3; MacLennan A H et al. Am. J. Obstet. Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., *Drugs Fut*, 21 (11), 1116 (1996); Brickner, S J et al., *J Med Chem*, 39 (3), 673 (1996); Mallesham, B et al., *Org Lett*, 5 (7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

The present invention further relates to a pharmaceutical composition comprising a therapeutically effective amount of at least one compound I as defined above or an N-oxide, a tautomeric form, a stereoisomer or a pharmaceutically acceptable salt thereof, or comprising at least one compound as defined in any of the preceding claims wherein at least one of the atoms has been replaced by its stable, non-radioactive isotope, preferably wherein at least one hydrogen atom has been replaced by a deuterium atom, in combination with at least one pharmaceutically acceptable carrier and/or auxiliary substance.

The present invention further relates to a compound I as defined above or an N-oxide, a tautomeric form, a stereoisomer or a pharmaceutically acceptable salt thereof for use as a medicament.

The present invention also relates to a compound I as defined above or an N-oxide, a tautomeric form, a stereoisomer or a pharmaceutically acceptable salt thereof for the treatment of disorders which respond to the modulation of the 5-$HT_{2c}$ receptor.

The present invention also relates to the use of a compound I as defined above or of an N-oxide, a tautomeric form, a stereoisomer or a pharmaceutically acceptable salt thereof for the manufacture of a medicament for the treatment of disorders which respond to the modulation of the 5-$HT_{2c}$ receptor, and to a method for treating disorders which respond to the modulation of the 5-$HT_{2c}$ receptor, which method comprises administering to a subject in need thereof at least one compound I as defined above or an N-oxide, a tautomeric form, a stereoisomer or a pharmaceutically acceptable salt thereof.

The compounds of the present invention are modulators of the 5-$HT_{2C}$ receptor. Specifically, the compounds of formula I are agonists or partial agonists of the 5-$HT_{2C}$ receptor. Thus, in a specific embodiment, the invention relates to a compound I as defined above or an N-oxide, a tautomeric form, a stereoisomer or a pharmaceutically acceptable salt thereof for the treatment of disorders which respond to 5-$HT_{2c}$ receptor agonists, further to the use of a compound I as defined above or of an N-oxide, a tautomeric form, a stereoisomer or a pharmaceutically acceptable salt thereof for the manufacture of a medicament for the treatment of disorders which respond to 5-$HT_{2c}$ receptor agonists, and to a method for treating disorders which respond to 5-$HT_{2c}$ receptor agonists, which method comprises administering to a subject in need thereof at least one compound I as defined above or an N-oxide, a tautomeric form, a stereoisomer or a pharmaceutically acceptable salt thereof.

Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

In one aspect of the invention, the diseases to be treated are disorders are damage of the central nervous system, disorders of the central nervous system, eating disorders, ocular hypertension, cardiovascular disorders, gastrointestinal disorders and diabetes.

Disorders or diseases of the central nervous system are understood as meaning disorders which affect the spinal cord and, in particular, the brain. These are, for example, cognitive dysfunction, attention deficit disorder/hyperactivity syndrome and cognitive deficits related with schizophrenia, attention deficit/hyperactivity syndrome, personality disorders, affective disorders, motion or motor disorders, pain, migraine, sleep disorders (including disturbances of the Circadian rhythm), feeding disorders, diseases associated with neurodegeneration, addiction diseases, obesity or psoriasis.

Examples of cognitive dysfunction are deficits in memory, cognition, and learning, Alzheimer's disease, age-related cognitive decline, and mild cognitive impairment, or any combinations thereof. Examples of personality disorders are schizophrenia and cognitive deficits related to schizophrenia. Examples of affective disorders are depression, anxiety, bipolar disorder and obsessive compulsive disorders, or any combination thereof. Examples of motion or motor disorders are Parkinson's disease and epilepsy. Examples of feeding disorders are obesity, bulimia, weight loss and anorexia, especially anorexia nervosa. Examples of diseases associated with neurodegeneration are stroke, spinal or head trauma, and head injuries, such as hydrocephalus.

Pain condition includes nociceptive pain, neuropathic pain or a combination thereof. Such pain conditions or disorders can include, but are not limited to, postoperative pain, osteoarthritis pain, pain due to inflammation, rheumatoid arthritis pain, musculoskeletal pain, burn pain (including sun-burn), ocular pain, the pain associated with dental conditions (such as dental caries and gingivitis), post-partum pain, bone fracture, herpes, HIV, traumatic nerve injury, stroke, post-ischemia, fibromyalgia, reflex sympathetic dystrophy, complex regional pain syndrome, spinal cord injury, sciatica, phantom limb pain, diabetic neuropathy, hyperalgesia and cancer.

In certain other embodiments, the disease condition is bladder dysfunction, including urinary incontinence.

Diabetes includes diabetes insipidus, diabetes mellitus, type I diabetes, type II diabetes, type III diabetes, diabetes secondary to pancreatic diseases, diabetes related to steroid use, diabetes complications, hyperglycemia and insulin resistance.

The addiction diseases include psychiatric disorders and behavioral disturbances which are caused by the abuse of psychotropic substances, such as pharmaceuticals or narcotics, and also other addiction diseases, such as addiction to gaming (impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate, other stimulants including caffeine and nicotine. Addictive substances which come particularly into consideration are opioids, cocaine, amphetamine or amphetamine-like substances, nicotine and alcohol. Especially, addiction disorders include alcohol abuse, cocaine abuse, tobacco abuse and smoking cessation.

With regard to the treatment of addiction diseases, particular preference is given to those compounds according to the invention of the formula (I) which themselves do not possess any psychotropic effect. This can also be observed in a test using rats, which, after having been administered compounds which can be used in accordance with the invention, reduce their self administration of psychotropic substances, for example cocaine.

Examples of gastrointestinal disorders are irritable bowel syndrome.

Preferably, the disorders are selected from the group consisting of bipolar disorder, depression, atypical depression, mood episodes, adjustment disorders, anxiety, panic disorders, post-traumatic syndrome, psychoses, schizophrenia, cognitive deficits of schizophrenia, memory loss, dementia of aging, Alzheimer's disease, behavioral disorders associated with dementia, social phobia, mental disorders in childhood, attention deficit hyperactivity disorder, organic mental disorders, autism, mutism, disruptive behavior disorder, impulse control disorder, borderline personality disorder, obsessive compulsive disorder, migraine and other conditions associated with cephalic pain or other pain, raised intracranial pressure, seizure disorders, epilepsy, substance use disorders, alcohol abuse, cocaine abuse, tobacco abuse, smoking cessation, sexual dysfunction/erectile dysfunction in males, sexual dysfunction in females, premenstrual syndrome, late luteal phase syndrome, chronic fatigue syndrome, sleep disorders, sleep apnoea, chronic fatigue syndrome, psoriasis, Parkinson's disease, spinal cord injury, trauma, stroke, pain, bladder dysfunction/urinary incontinence, encephalitis, meningitis, eating disorders, obesity, bulimia, weight loss, anorexia nervosa, ocular hypertension, cardiovascular disorders, gastrointestinal disorders, diabetes insipidus, diabetes mellitus, type I diabetes, type II diabetes, type III diabetes, diabetes secondary to pancreatic diseases, diabetes related to steroid use, diabetes complications, hyperglycemia and insulin resistance, and are specifically schizophrenia, depression, bipolar disorders, obesity or substance use disorders.

The compounds of the invention may be used for a preventive treatment (prophylaxis), in particular as relapse prophylaxis or phase prophylaxis, but are preferably used for a treatment in its proper sense, i.e. for the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

In another embodiment, the present invention relates to the use of a compound I as defined above or an N-oxide, a tautomeric form, a stereoisomer or a pharmaceutically acceptable salt thereof for preparing a medicament for preventing (the development of) a disease condition as described above and to a method for preventing (the development of) a disease condition as described above comprises administering to the subject in need of treatment thereof (e.g., a mammal, such as a human) a therapeutically effective amount of a compound I as defined above or an N-oxide, a tautomeric form, a stereoisomer or a pharmaceutically acceptable salt thereof. As used herein, the term "prevent" a disease condition by administration of any of the compounds described herein means that the detectable physical characteristics or symptoms of the disease or condition do not develop following the administration of the compound described herein. Alternatively, the method comprises administering to the subject a therapeutically effective amount of a compound I as defined above or an N-oxide, a tautomeric form, a stereoisomer or a pharmaceutically acceptable salt thereof, in combination with a therapeutically effective amount of at least one cognitive enhancing drug.

In yet another embodiment, the present invention relates to the use a compound I as defined above or an N-oxide, a tautomeric form, a stereoisomer or a pharmaceutically acceptable salt thereof for preparing a medicament for preventing the progression (e.g., worsening) of a disease condition and to a method for preventing the progression (e.g., worsening) of a disease condition, which method comprises administering to the subject in need of treatment thereof (e.g., a mammal, such as a human) a therapeutically effective amount of a compound I as defined above or an N-oxide, a tautomeric form, a stereoisomer or a pharmaceutically acceptable salt thereof.

There are several lines of evidence suggesting that $5\text{-HT}_{2C}$ agonists or partial agonists would have therapeutic use in a variety of diseases, disorders and conditions.

Knockout mice models lacking the $5\text{-HT}_{2C}$ receptor exhibit hyperphagia, obesity and are more prone to seizures and sudden death [Tecott L H, Sun L M, Akana S F, Strack A M, Lowenstein D H, Dallman M F, Julius D (1995) Eating disorder and epilepsy in mice lacking $5\text{-HT}_{2C}$ serotonin receptors. Nature 374:542-546]. They also exhibit compulsive-like behavior [Chou-Green J M, Holscher T D, Dallman M F, Akana S F (2003). Compulsive behavior in the $5\text{-HT}_{2C}$ receptor knockout mouse. Phys. Behav. 78:641-649], hyper-responsiveness to repeated stress [Chou-Green J M, Holscher T D, Dallman M F, Akana S F (2003). Repeated stress in young and old $5\text{-HT}_{2C}$ receptor knockout mouse. Phys. Behav. 79:217-226], wakefulness [Frank M G, Stryker M P, Tecott L H (2002). Sleep and sleep homeostasis in mice lacking the $5\text{-HT}_{2C}$ receptor. Neuropsychopharmacology 27:869-873], hyperactivity and drug dependence [Rocha B A, Goulding E H, O'Dell L E, Mead A N, Coufal N G, Parsons L H, Tecott L H (2002). Enhanced locomotor, reinforcing and neurochemical effects of cocaine in serotonin 5-hydroxytriyptamine 2C receptor mutant mice. *J. Neurosci.* 22:10039-10045].

5-HT$_{2C}$ is unique among other G-protein-coupled receptors (GPCRs) in that its pre-mRNA is a substrate for base modification via hydrolytic deamination of adenosines to yield inosines. Five adenosines, located within a sequence encoding the putative second intracellular domain can be converted to inosines. This editing can alter the coding potential of the triplet codons and allows for the generation of multiple different receptor isoforms. The edited receptor isoforms were shown to have reduced ability to interact with G-proteins in the absence of agonist stimulation [Werry, T D, Loiacono R, Sexton P A, Christopoulos A (2008). RNA editing of the serotonin 5-HT$_{2C}$ receptor and its effects on cell signaling, pharmacology and brain function. *Pharmac. Therap.* 119:7-23].

Edited 5-HT$_{2C}$ isoforms with reduced function are significantly expressed in the brains of depressed suicide victims [Schmauss C (2003) Serotonin 2C receptors: suicide, serotonin, and runaway RNA editing. *Neuroscientist* 9:237-242. Iwamoto K, Kato T (2003). RNA editing of serotonin 2C receptor in human postmortem brains of major mental disorders. *Neurosci. Lett.* 346:169-172] and in the learned helplessness rats (a well established animal model of depression) [Iwamotoa K, Nakatanib N, Bundoa M, Yoshikawab T, Katoa T (2005). Altered RNA editing of serotonin 2C receptor in a rat model of depression. *Neurosci. Res.* 53: 69-76] suggesting a link between 5-HT$_{2C}$ function and depression. There are also implications of edited 5-HT$_{2C}$ isoforms and spatial memory [Du Y, Stasko M, Costa A C, Davissone M T, Gardiner K J (2007). Editing of the serotonin 2C receptor pre-mRNA Effects of the Morris Water Maze. *Gene* 391:186-197]. In addition, fully edited isoforms of the human 5-HT$_{2C}$ receptor display a striking reduction in sensitivity to lysergic acid diethylamide (LSD) and to atypical antipsychotic drugs clozapine and loxapine, suggesting a possible role of the receptor in the etiology and pharmacology of schizophrenia [Niswender C M, Herrick-Davis K, Dilley G E, Meltzer H Y, Overholser J C, Stockmeier C A, Emeson R B, Sanders-Bush E (2001). RNA Editing of the Human Serotonin 5-HT$_{2C}$ Receptor: Alterations in Suicide and Implications for Serotonergic *Pharmacotherapy. Neuropsychopharm.* 24:478-491].

Recently, the availability of potent and selective 5-HT$_{2C}$ receptor agonists made it possible to directly investigate the effects of 5-HT$_{2C}$ agonists and their therapeutic potential. Thus recent studies demonstrated that selective 5-HT$_{2C}$ agonists resulted in decreased food intake and body weight gain in normal and obese rats [Smith B M, et al. (2008). Discovery and structure-activity relationship of (1R)-8-chloro-2,3,4,5-tetrahydro-1-methyl-1H-3-benzazepine (Lorcaserin), a selective serotonin 5-HT$_{2C}$ receptor agonist for the treatment of obesity. *J Med Chem* 51:305-313. Thomsen W J, Grottick A J, Menzaghi F, Reyes-Saldana H, Espitia S, Yuskin D, Whelan K, Martin M, Morgan M, Chen W, Al-Shama H, Smith B, Chalmers D, Behan D (2008) Lorcaserin, A Novel Selective Human 5-HT$_{2C}$ Agonist: In Vitro and In Vivo Pharmacological Characterization. *J Pharmacol Exp Ther.* 325: 577-587. Rosenzweig-Lipson S, Zhang J, Mazandarani H, Harrison B L, Sabb A, Sabalski J, Stack G, Welmaker G, Barrett J E, Dunlop J (2006) Antiobesity-like effects of the 5-HT$_{2C}$ receptor agonist WAY-161503. *Brain Res.* 1073-1074:240-251. Dunlop J, Sabb A L, Mazandarani H, Zhang J, Kalgaonker S, Shukhina E, Sukoff S, Vogel R L, Stack G, Schechter L, Harrison B L, Rosenzweig-Lipson S (2005). WAY-163909 [97bR,10aR)-1,2,3,4,8,9,10,10a-octahydro-7bH-cyclopenta-[b][1,4]diazepino[6,7,1hi]indole], a novel 5-hydroxytryptamine 2C receptor-selective agonist with anorectic activity. *J Pharmacol Exp Ther.* 313:862-869.].

Furthermore, selective 5-HT$_{2C}$ receptor agonists produce antidepressant effects in animal models of depression comparable to those of SSRIs but with a much faster onset of action and a therapeutic window that avoids antidepressant-induced sexual dysfunction. These agonists were also effective in animal models of compulsive behavior such as scheduled induced polydipsia and they also exhibited decreased hyperactivity and aggression in rodents [Rosenzweig-Lipson S, Sabb A, Stack G, Mitchell P, Lucki I, Malberg J E, Grauer S, Brennan J, Cryan J F, Sukoff Rizzo S J, Dunlop J, Barrett J E, Marquis K L (2007) Antidepressant-like effects of the novel, selective, 5-HT$_{2C}$ receptor agonist WAY-163909 in rodents. *Psychopharmacology* (Berlin) 192:159-170. Rosenzweig-Lipson S, Dunlop J, Marquis K L (2007) 5-HT$_{2C}$ receptor agonists as an innovative approach for psychiatric disorders. *Drug news Perspect,* 20: 565-571. Cryan, J F, Lucki I (2000). Antidepressant-like behavioral effects mediated by 5-Hydroxytryptamine 2C receptors. *J. Pharm. Exp. Ther.* 295:1120-1126.].

Acute or chronic administration of 5-HT$_{2C}$ agonists decreases the firing rate of ventral tegmental area dopamine neurons but not that of substantia nigra. In addition 5-HT$_{2C}$ agonists reduce dopamine levels in the nucleus accumbens but not in the striatum (the region of the brain mostly associated with extrapyramidal side effects) [Di Matteo, V., Di Giovanni, G., Di Mascio, M., & Esposito, E. (1999). SB 242084, a selective serotonin 2C receptor antagonist, increases dopaminergic transmission in the mesolimbic system. *Neuropharmacology* 38, 1195-1205. Di Giovanni, G., Di Matteo, V., Di Mascio, M., & Esposito, E. (2000). Preferential modulation of mesolimbic vs. nigrostriatal dopaminergic function by serotonin 2C/2B receptor agonists: a combined in vivo electrophysiological and microdialysis study. *Synapse* 35, 53-61. Marquis K L, Sabb A L, Logue S F, Brennan J A, Piesla M J, Comery T A, Grauer S M, Ashby C R, Jr., Nguyen H Q, Dawson L A, Barrett J E, Stack G, Meltzer H Y, Harrison B L, Rosenzweig-Lipson S (2007) WAY-163909 [(7bR,10aR)-1,2,3,4,8,9,10,10a-octahydro-7bH-cyclopenta-[b][1,4]diazepino[6,7,1hi]indole]: A novel 5-hydroxytryptamine 2C receptor-selective agonist with preclinical antipsychotic-like activity. *J Pharmacol Exp Ther* 320:486-496.]. Therefore it is expected that 5-HT$_{2C}$ receptor agonists will selectively decrease mesolimibic dopamine levels without affecting the nigrostriatal pathway thus avoiding the EPS side effects of typical antipsychotics. Several 5-HT$_{2C}$ receptor agonists have shown antipsychotic activity in animal models of schizophrenia without EPS based on the lack of effect in catalepsy [Marquis K L, Sabb A L, Logue S F, Brennan J A, Piesla M J, Comery T A, Grauer S M, Ashby C R, Jr., Nguyen H Q, Dawson L A, Barrett J E, Stack G, Meltzer H Y, Harrison B L, Rosenzweig-Lipson S (2007) WAY-163909 [(7bR,10aR)-1,2,3,4,8,9,10,10a-octahydro-7bH-cyclopenta-[b][1,4]diazepino[6,7,1hi]indole]: A novel 5-hydroxytryptamine 2C receptor-selective agonist with preclinical antipsychotic-like activity. *J Pharmacol Exp Ther* 320:486-496. Siuciak J A, Chapin D S, McCarthy S A, Guanowsky V, Brown J, Chiang P, Marala R, Patterson T, Seymour P A, Swick A, Iredale P A (2007) CP-809,101, a selective 5-HT$_{2C}$ agonist, shows activity in animal models of antipsychotic activity. *Neuropharmacology* 52:279-290]. The antipsychotic activity of 5-HT$_{2C}$ receptor agonists without EPS coupled with their beneficial effects in mood disorders and cognition and their antiobesity like effects render 5-HT$_{2C}$ receptor agonists as unique agents to treat schizophrenia [Rosenzweig-Lipson S, Dunlop J, Marquis K L (2007) 5-HT$_{2C}$ receptor agonists as an innovative approach for psychiatric disorders. *Drug news Perspect,* 20: 565-571. Dunlop J, Marquis K L, Lim H K, Leung L, Kao J, Cheesman C, Rosenzweig-Lipson S (2006). Pharmacological profile of the 5-HT$_{2C}$ receptor agonist WAY-163909; therapeutic potential in multiple indications. *CNS Dug Rev.* 12:167-177.].

In addition 5-HT$_{2C}$ modulation has been implicated in epilepsy [Isaac M (2005). Serotonergic 5-HT$_{2C}$ receptors as a potential therapeutic target for the antiepileptic drugs. *Curr. Topics Med. Chem.* 5:59:67], psoriasis [Thorslund K, Nordlind K (2007). Serotonergic drugs-a possible role in the treatment of psoriasis? *Drug News Perspect* 20:521-525], Parkinson's disease and related motor disorders [Esposito E, Di Matteo V, Pierucci M, Benigno A, Di Giavanni, G (2007). Role of central 5-HT$_{2C}$ receptor in the control of basal ganglia functions. *The Basal Ganglia Pathophysiology: Recent Advances* 97-127], behavioral deficits [Barr A M, Lahmann-Masten V, Paulus M, Gainetdinov R P, Caron M G, Geyer M A (2004). The selective serotonin-2A receptor antagonist M100907 reverses behavioral deficits in dopamine transporter knockout mice. Neuropsychopharmacology 29:221-228], anxiety [Dekeyne A, Mannoury la Cour C, Gobert A, Brocco M, Lejuene F, Serres F, Sharp T, Daszuta A, Soumier A, Papp M, Rivet J M, Flik G, Cremers T I, Muller O, Lavielle G, Millan M J (2208). S32006, a novel 5-HT$_{2C}$ receptor antagonists displaying broad-based antidepressant and anxiolytic properties in rodent models. *Psychopharmacology* 199:549-568. Nunes-de-Souza V, Nunes-de-Souza R L, Rodgers R J, Canto-de-Souza A (2008). 5-HT2 receptor activation in the midbrain periaqueductal grey (PAG) reduces anxiety-like behavior in mice. *Behav. Brain Res.* 187:72-79.], migraine [Leone M, Rigamonti A, D'Amico D, Grazzi L, Usai S, Bussone G (2001). The serotonergic system in migraine. *Journal of Headache and Pain* 2 (Suppl. 1):S43-S46], Alzheimer's disease [Arjona A A, Pooler A M, Lee R K, Wurtman R J (2002). Effect of a 5-HT$_{2C}$ serotonin agonist, dexnorfenfluramine, on amyloid precursor protein metabolism in guinea pigs. *Brain Res.* 951:135-140], pain and spinal cord injury [Nakae A, Nakai K, Tanaka T, Hagihira S, Shibata M, Ueda K, Masimo T (2008). The role of RNA editing of the serotonin 2C receptor in a rat model of oro-facial neuropathic pain. *The European Journal of Neuroscience* 27:2373-2379. Nakae A, Nakai K, Tanaka T, Takashina M, Hagihira S, Shibata M, Ueda K, Mashimo T (2008). Serotonin 2C receptor mRNA editing in neuropathic pain model. *Neurosci. Res.* 60:228-231. Kao T, Shumsky J S, Jacob-Vadakot S, Timothy H B, Murray M, Moxon, K A (2006). Role of the 5-HT$_{2C}$ receptor in improving weight-supported stepping in adult rats spinalized as neonates. *Brain Res.* 1112:159-168.], sexual dysfunction [Motofei I G (2008). A dual physiological character for sexual function: the role of serotonergic receptors. *BJU International* 101:531-534. Shimada I, Maeno K, Kondoh Y, Kaku H, Sugasawa K, Kimura Y, Hatanaka K, Naitou Y, Wanibuchi F, Sakamoto S, Tsukamoto S (2008). Synthesis and structure-activity relationships of a series of benzazepine derivatives as 5-HT$_{2C}$ receptor agonists. *Bioorg. Med. Chem.* 16:3309-3320.], smoking cessation [Fletcher P J, Le A D, Higgins G A (2008). Serotonin receptors as potential targets for modulation of nicotine use and dependence. *Progress Brain Res.* 172:361-83], substance dependence [Bubar M J, Cunningham K A (2008). Prospects for serotonin 5-HT2R pharmacotherapy in psychostimulant abuse. *Progress Brain Res.* 172:319-46], and ocular hypertension [Sharif N A, McLaughlin M A, Kelly C R (2006). AL-34662: a potent, selective, and efficacious ocular hypotensive serotonin-2 receptor agonist. *J Ocul Pharmacol Ther.* 23:1-13].

Further, 5HT modulation can be useful in the treatment of pain, both neuropathic and nociceptive pain, see for example U.S. Patent application publication US2007/0225277. Obata, Hideaki; Ito, Naomi; Sasaki, Masayuki; Saito, Shigeru; Goto, Fumio. Possible involvement of spinal noradrenergic mechanisms in the antiallodynic effect of intrathecally administered 5-HT2C receptor agonists in the rats with peripheral nerve injury. *European Journal of Pharmacology* (2007), 567 (1-2), 89-94. Serotonin2C receptor mRNA editing in neuropathic pain model. Nakae, Aya; Nakai, Kunihiro; Tanaka, Tatsuya; Takashina, Masaki; Hagihira, Satoshi; Shibata, Masahiko; Ueda, Koichi; Mashimo, Takashi. Department of Anesthesiology & Intensive Care Medicine, Graduate School of Medicine, Osaka University, *Neuroscience Research* (Amsterdam, Netherlands) (2008), 60(2), 228-231. Antiallodynic effects of intrathecally administered 5-HT2C receptor agonists in rats with nerve injury. Obata, Hideaki; Saito, Shigeru; Sakurazawa, Shinobu; Sasaki, Masayuki; Usui, Tadashi; Goto, Fumio. Department of Anesthesiology, Gunma University Graduate School of Medicine, Maebashi, Gunma, Japan. *Pain* (2004), 108 (1-2), 163-169. Influence of 5,7-dihydroxytryptamine (5,7-DHT) on the antinociceptive effect of serotonin (5-HT) 5-HT2C receptor agonist in male and female rats. Brus, Ryszard; Kasperska, Alicja; Oswiecimska, Joanna; Szkilnik, Ryszard. Department of Pharmacology, Silesian Medical University, Zabrze, Pol. *Medical Science Monitor* (1997), 3 (5), 654-656.

Modulation of 5HT2 receptors may be beneficial in the treatment of conditions related to bladder function, in particular, urinary incontinence. [Discovery of a novel azepine series of potent and selective 5-HT2C agonists as potential treatments for urinary incontinence. Brennan, Paul E.; Whitlock, Gavin A.; Ho, Danny K. H.; Conlon, Kelly; McMurray, Gordon. *Bioorganic & Medicinal Chemistry Letters* (2009), 19 (17), 4999-5003. Investigation of the role of 5-HT2 receptor subtypes in the control of the bladder and the urethra in the anesthetized female rat. Mbaki, Y.; Ramage, A. G. Department of Pharmacology, University College London, London, UK. *British Journal of Pharmacology* (2008), 155 (3), 343-356.] In particular, compounds with agonist activity at 5-HT$_{2C}$ have been shown to be useful in treating urinary incontinence, see for example U.S. Patent application publications US2008/0146583 and US 2007/0225274.

In the use and the method of the invention, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

Actual dosage levels of active ingredients in the pharmaceutical compositions of the present invention can be varied so as to obtain an amount of the active compound(s) that is effective to achieve the desired therapeutic response for a particular subject (e.g., a mammal, preferably, a human (patient)), compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the present invention can also be administered to a subject as a pharmaceutical composition comprising the compounds of interest in combination with at least one pharmaceutically acceptable carriers. The phrase "therapeutically effective amount" of the compound of the present invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a subject (namely, a mammal, such as a human) ranges from about 0.01 mg/kg body weight to about 100 mg/kg body weight. More preferable doses can be in the range of from about 0.01 mg/kg body weight to about 30 mg/kg body weight. If desired, the effective daily dose can be divided into multiple doses for purposes of administration. Consequently, single dose compositions may contain such amounts or submultiples thereof to make up the daily dose.

In one aspect, the present invention provides pharmaceutical compositions. The pharmaceutical compositions of the present invention comprise the compounds of the present invention or an N-oxide, a tautomeric form, a stereoisomer or a pharmaceutically acceptable salt or solvate thereof. The pharmaceutical compositions of the present invention comprise compounds of the present invention that can be formulated together with at least one non-toxic pharmaceutically acceptable carrier.

In yet another embodiment, the present invention provides a pharmaceutical composition comprising compounds of the present invention or an N-oxide, a tautomeric form, a stereoisomer or a pharmaceutically acceptable salt thereof, and one or more pharmaceutically acceptable carriers, alone or in combination with one or more compounds that are not the compounds of the present invention. Examples of one or more compounds that can be combined with the compounds of the present invention in pharmaceutical compositions, include, but are not limited to, one or more cognitive enhancing drugs.

The pharmaceutical compositions of this present invention can be administered to a subject (e.g., a mammal, such as a human) orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a nontoxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of the present invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings wellknown in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agaragar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of the present invention include powders, sprays, ointments and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (*J. Pharmaceutical Sciences*, 1977, 66: 1 et seq.). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, piperazine and the like.

The compounds of the present invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The following examples serve to explain the invention without limiting it.

EXAMPLES

The compounds were either characterized via proton-NMR in $d_6$-dimethylsulfoxide or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H-NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

Enantiomers were separated/purified either by chiral supercritical fluid chromatography (SFC) (method A) or by chiral HPLC (method A).

Method A—Chiral Analytical SFC

Analytical SFC was performed on an Aurora A5 SFC Fusion and Agilent 1100 system running under Agilent Chemstation software control. The SFC system included a 10-way column switcher, CO2 pump, modifier pump, oven, and backpressure regulator. The mobile phase comprised of supercritical CO2 supplied by a beverage-grade CO2 cylinder with a modifier mixture of methanol at a flow rate of 3 mL/min. Oven temperature was at 35° C. and the outlet pressure at 150 bar. The UV detector was set to collect at wavelengths of 220 nm and 254 nm. The mobile phase gradient started with 5% modifier and held it for 0.1 minutes at a flow rate of 1 mL/min, then the flow rate was ramped up to 3 mL/min and held for 0.4 min. The modifier was ramped from 5% to 15% over the next 8 minutes at 3 mL/min then held for 1 minute at 15% modifier (3 mL/min). The gradient was ramped down from 15% to 5% modifier over 0.5 min (3 mL/min). The instrument was fitted with a Chiralpak AS-H column with dimensions of 4.6 mm i.d.×150 mm length with 5 µm particles.

Method B—Chiral HPLC
System: KNAUER preparative HPLC
Pump: Preparative pump 1800
Detector: Smartline UV detector 2600 257 nm
Sample pump: Knauer HPLC-Pump K-120
Fractional collector: Smartline Valves Drive S6
Software: ChromGate® V3.1.7, KNAUER Instrument Control
Column: Whelk O 4.6 mm ID×250 mm
Column temperature: 25° C.
Mobile phase: hexane/isopropylamine 95/5
Flow rate: 1 ml/min I. Preparation Examples Example 1

8,8-Dimethyl-2,3,4,6,7,8-hexahydro-1H-[1,4]diazepino [6,7,1-ij]quinoline (compound of the formula I.g, I.h or I.i in which the combination of $R^{5a}$, $R^{5b}$, $R^7$, $R^8$ and $R^{9a}$ is as in row B-1 of Table B)

1.1 Preparation of tert-butyl 1-(3-methylbut-2-enoyl)-2,3-dihydro-1H-benzo[e][1,4]diazepine-4 (5H)-carboxylate 1 g (4.04 mmol) of tert-butyl 2,3-dihydro-1H-benzo[e][1,4]diazepine-4(5H)-carboxylate was dissolved in 20 mL of dichloromethane and treated with 1.54 mL (8.86 mL) of triethylamine followed by 0.53 mL (4.83 mmol) of 3-methylbut-2-enoyl chloride. The reaction mixture was stirred over night at room temperature, poured onto water (50 mL) and extracted three times with 50 mL of dichloromethane each. The organic phases were combined, washed with a saturated solution of sodium chloride, dried over magnesium sulfate and concentrated in vacuo. The residue was purified by column chromatography on silica (eluent: 5-10% methanol in dichloromethane) to yield 1.27 g of the title compound as a white solid.

ESI-MS: m/z (%): 275 (80, [M–$C_4H_9$+2H]$^+$, 331 (20, [M+H]$^+$).

1.2 Preparation of tert-butyl 8,8-dimethyl-6-oxo-3,4, 7,8-tetrahydro-1H-[1,4]diazepino[6,7,1-ij]quinoline-2(6H)-carboxylate A solution of 0.33 g (1.0 mmol) of tert-butyl 1-(3-methylbut-2-enoyl)-2,3-dihydro-1H-benzo[e][1,4]diazepine-4 (5H)-carboxylate of step 1.1 was irradiated with a 150 W mercury lamp in a immersion well reactor with a pyrex filter in 20 mL of acetone until completion of the reaction monitored by liquid chromatography. The solution was concentrated in vacuo and the residue was purified by column chromatography on silica (eluent: 10-30% ethyl acetate in heptane) to yield 202 mg of the title compound as a beige solid.

ESI-MS: m/z (%): 275 (80, [M–$C_4H_9$+2H]$^+$, 331 (20, [M+H]$^+$).

1.3 Preparation of tert-butyl 8,8-dimethyl-3,4,7,8-tetrahydro-1H-[1,4]diazepino[6,7,1-ij]quinoline-2 (6H)-carboxylate A solution of 38 mg (0.115 mmol) tert-butyl 8,8-dimethyl-6-oxo-3,4,7,8-tetrahydro-1H-[1,4]diazepino[6,7,1-ij]quinoline-2(6H)-carboxylate of step 1.2 in 1 mL of tetrahydrofuran was treated with 0.46 mL of 1 molar solution of borohydride-tetrahydrofuran complex in tetrahydrofuran. The mixture was stirred over night, and then quenched with water and diluted hydrochloric acid. The pH was adjusted to pH 9 by addition of aqueous sodium hydroxide solution and the mixture extracted three times with 10 mL of dichloromethane each. The solution was dried over magnesium sulfate and concentrated in vacuo. The residue was purified by column chromatography on silica (eluent: 20-30% ethyl acetate in heptane) to yield 21 mg of the title compound as a clear oil.

ESI-MS: m/z (%): 317 (100, [M+H]$^+$).

1.4 Preparation of 8,8-dimethyl-2,3,4,6,7,8-hexahydro-1H-[1,4]diazepino[6,7,1-ij]quinoline 287 mg (0.9 mmol) of tert-butyl 8,8-dimethyl-3,4,7,8-tetrahydro-1H-[1,4]diazepino[6,7,1-ij]quinoline-2(6H)-carboxylate of step 1.3 were dissolved in 5 mL of dichloromethane and treated with 2.5 mL of trifluoroacetic acid. The mixture was stirred over night at room temperature and then extracted once with water (10 mL). The organic phase was then extracted twice with a diluted solution of sodium hydroxide (10 mL each), dried over magnesium sulfate and concentrated in vacuo. The residue was purified by column chromatography on silica (eluent: 10-30% methanol in dichloromethane) to yield 141 mg of the title compound as a yellow oil.

ESI-MS: m/z (%): 217.15 (100, [M+H]$^+$).
$^1$H-NMR (500 MHz, CDCl$_3$): δ=7.15 (d, 1H), 6.85 (d, 1H), 6.75 (m, 1H), 3.80 (s, 2H), 3.15 (m, 2H), 3.00 (s, 4H), 1.65 (m, 2H), 1.20 (s, 6H).

Example 2

1,2,3,4-Tetrahydrospiro[[1,4]diazepino[6,7,1-ij]quinoline-8,1'-cyclopent[2]en]-6(7H)-one 2,2,2-trifluoroacetate (compound of the formula I.j, I.k or I.l in which the combination of R$^{5a}$, R$^{5b}$, R$^7$, R$^8$ and R$^{9a}$ is as in row B-401 of Table B)

2.1 Preparation of tert-butyl 6-oxo-3,4,6,7-tetrahydrospiro[[1,4]diazepino[6,7,1-ij]quinoline-8,1'-cyclopent[2]ene]-2(1H)-carboxylate (compound of the formula I.g, I.h or I.i in which the combination of R$^{5a}$, R$^{5b}$, R$^7$, R$^8$ and R$^{9a}$ is as in row B-401 of Table B, wherein however R$^1$ is not H, but Boc)

A solution of 50 mg (0.128 mmol) tert-butyl 9-chloro-1-(2-cyclopentenylacetyl)-2,3-dihydro-1H-benzo[e][1,4]diazepine-4(5H)-carboxylate was dissolved in 1 mL of degassed dry acetonitrile under argon, treated with 1.4 mg (0.006 mmol) of palladium acetate, 6.10 mg (0.013 mmol) dicyclohexyl(2',4',6'-triisopropylbiphenyl-2-yl)phosphine and 53 mg (0.384 mmol) potassium carbonate. The mixture was stirred for 10 hours at 120° C. in a synthesis microwave system. After cooling to room temperature the mixture was filtered over celite, diluted with dichloromethane and then extracted twice with a diluted solution of sodium chloride (10 mL each), dried over magnesium sulfate and concentrated in vacuo. The residue was purified by column chromatography on silica (eluent: 10-30% ethyl acetate in heptane) to yield 40 mg of the title compound as a yellow oil.

ESI-MS: m/z (%): 298 (80, [M—C$_4$H$_9$+2H]$^+$, 217 (20, [M+H]$^+$).

2.2 Preparation of 1,2,3,4-tetrahydrospiro[[1,4]diazepino[6,7,1-ij]quinoline-8,1'-cyclopent[2]en]-6(7H)-one 2,2,2-trifluoroacetate Boc-deprotection of the compound obtained in step 2.1 analogously to example 1.4 yielded the title compound.
ESI-MS: m/z (%): 255 (100, [M+H]$^+$).

Example 3

8-Methyl-8-phenyl-3,4,7,8-tetrahydro-1H-[1,4]diazepino[6,7,1-ij]quinolin-6(2H)-one, hydrochloride (compound of the formula I.j, I.k or I.l in which the combination of R$^{5a}$, R$^{5b}$, R$^7$, R$^8$ and R$^{9a}$ is as in row B-161 of Table B)

392 mg (1 mmol) of tert-butyl 1-(3-phenylbut-2-enoyl)-2,3-dihydro-1H-benzo[e][1,4]diazepine-4(5H)-carboxylate were treated with 1 g of polyphosphoric acid. The mixture was heated to 90° C. for 2 hours and then quenched with a saturated solution of potassium carbonate at 0° C. The mixture was extracted three times with ethyl acetate (20 mL each), the combined organic fractions dried over magnesium sulfate and concentrated in vacuo. The residue was purified by column chromatography on silica (eluent: 10-30% methanol in dichloromethane) to yield 86 mg of the title compound as a yellow foam.

ESI-MS: m/z (%): 293.1 (100, [M+H]$^+$).
$^1$H-NMR (500 MHz, DMSO-d6): δ=10.05 (bs, 1H), 9.85 (bs, 1H), 7.40 (d, 1H), 7.35 (d, 1H), 7.25 (m, 2H), 7.20 (m, 2H), 7.10 (m, 2H), 4.55 (m, 1H), 4.35 (m, 1H), 4.15 (m, 1H), 3.55 (m, 1H), 3.25 (m, 2H), 3.10 (m, 1H), 2.70 (m, 1H), 1.60 (s, 3H).

The following example was prepared analogously to example 1.

Example 4

8,8-Dimethyl-3,4,7,8-tetrahydro-1H-[1,4]diazepino[6,7,1-ij]quinolin-6(2H)-one (compound of the formula I.j, I.k or I.l in which the combination of R$^{5a}$, R$^{5b}$, R$^7$, R$^8$ and R$^{9a}$ is as in row B-1 of Table B)

ESI-MS: m/z (%): 231 (100, [M+H]$^+$).
1H-NMR (500 MHz, CDCl$_3$): δ=7.20 (d, 1H), 7.00 (m, 2H), 4.10 (s, 4H), 3.20 (m, 2H), 2.50 (s, 2H), 1.30 (s, 6H).

The following examples 5 and 6 were prepared analogously to example 2.

Example 5

1,2,3,4-Tetrahydrospiro[[1,4]diazepino[6,7,1-ij]quinoline-8,1'-cyclopentan]-6(7H)-one (compound of the formula I.j, I.k or 1.1 in which the combination of R$^{5a}$, R$^{5b}$, R$^7$, R$^8$ and R$^{9a}$ is as in row B-281 of Table B)

ESI-MS: m/z (%): 257 (100, [M+H]$^+$).

Example 6

1,2,3,4,6,7-Hexahydrospiro[[1,4]diazepino[6,7,1-ij]quinoline-8,1'-cyclopentane] (compound of the formula I.g, I.h or I.i in which the combination of R$^{5a}$, R$^{5b}$, R$^7$, R$^8$ and R$^{9a}$ is as in row B-281 of Table B)

ESI-MS: m/z (%): 243 (100, [M+H]$^+$).
$^1$H-NMR (500 MHz, CDCl$_3$): δ=7.15 (d, 1H), 6.95 (d, 1H), 6.80 (m, 1H), 3.90 (s, 2H), 3.20 (m, 2H), 3.05 (m, 4H), 1.95-1.65 (m, 10H).

The following examples 7 to 13 were prepared analogously to example 1.

Example 7

12a-Methyl-4,5,6,7,10,11,12,12a-octahydrocyclopenta[c][1,4]diazepino[6,7,1-ij]quinolin-9(9aH)-one (racemic cis diastereomer of the compound of the formula I.j, I.k or I.l in which the combination of $R^{5a}$, $R^{5b}$, $R^7$, $R^8$ and $R^{9a}$ is as in row B-441 of Table B)

ESI-MS: m/z (%): 257 (100, [M+H]$^+$).

Example 8

8-Methyl-8-(trifluoromethyl)-2,3,4,6,7,8-hexahydro-1H-[1,4]diazepino[6,7,1-ij]quinoline (single enantiomer of the compound of the formula I.g, I.h or I.i in which the combination of $R^{5a}$, $R^{5b}$, $R^7$, $R^8$ and $R^{9a}$ is as in row B-81 of Table B)

ESI-MS: m/z (%): 271 (100, [M+H]$^+$).

The retention time according to method A is 1.396 min.

Example 9

8-Methyl-8-(trifluoromethyl)-2,3,4,6,7,8-hexahydro-1H-[1,4]diazepino[6,7,1-ij]quinoline (single enantiomer of the compound of the formula I.g, I.h or I.i in which the combination of $R^{5a}$, $R^{5b}$, $R^7$, $R^8$ and $R^{9a}$ is as in row B-81 of Table B)

ESI-MS: m/z (%): 271 (100, [M+H]$^+$).

The retention time according to method A is 1.396 min is 1.543 min.

Example 10

12a-Methyl-4,5,6,7,10,11,12,12a-octahydrocyclopenta[c][1,4]diazepino[6,7,1-ij]quinolin-9(9aH)-one (racemic trans diastereomer of the compound of the formula I.j, I.k or I.l in which the combination of $R^{5a}$, $R^{5b}$, $R^7$, $R^8$ and $R^{9a}$ is as in row B-441 of Table B)

ESI-MS: m/z (%): 257 (100, [M+H]$^+$).

Example 11

12a-Methyl-4,5,6,7,9,9a,10,11,12,12a-decahydrocyclopenta[c][1,4]diazepino[6,7,1-ij]quinoline (racemic cis diastereomer of the compound of the formula I.g, I.h or I.i in which the combination of $R^{5a}$, $R^{5b}$, $R^7$, $R^8$ and $R^{9a}$ is as in row B-441 of Table B)

ESI-MS: m/z (%): 243 (100, [M+H]$^+$).

$^1$H-NMR (500 MHz, CDCl$_3$): δ=7.15 (d, 1H), 6.90 (d, 1H), 6.80 (m, 1H), 3.90 (m, 2H), 3.15 (m, 1H), 3.05 (m, 3H), 2.95 (m, 1H), 2.80 (m, 1H), 1.95 (m, 1H), 1.90 (m, 1H), 1.80 (m, 2H), 1.60 (m, 1H), 1.55 (m, 1H), 1.30 (m, 1H), 1.20 (s, 3H).

Example 12

8-Methyl-8-(trifluoromethyl)-3,4,7,8-tetrahydro-1H-[1,4]diazepino[6,7,1-ij]quinolin-6(2H)-one (racemic mixture of compound of the formula I.j, I.k or 1.1 in which the combination of $R^{5a}$, $R^{5b}$, $R^7$, $R^8$ and $R^{9a}$ is as in row B-81 of Table B)

ESI-MS: m/z (%): 285 (100, [M+H]$^+$).

Example 13

12a-Methyl-4,5,6,7,9,9a,10,11,12,12a-decahydrocyclopenta[c][1,4]diazepino-[6,7,1-ij]quinoline hydrochloride (racemic trans diastereomer of the compound of the formula I.g, I.h or I.i in which the combination of $R^{5a}$, $R^{5b}$, $R^7$, $R^8$ and $R^{9a}$ is as in row B-441 of Table B)

ESI-MS: m/z (%): 243 (100, [M+H]$^+$).

$^1$H-NMR (500 MHz, CDCl$_3$): δ=9.45 (bs, 1H), 9.05 (bs, 1H), 7.05 (d, 1H), 7.00 (d, 1H), 6.70 (m, 1H), 4.30 (m, 1H), 3.95 (m, 1H), 3.55 (m, 2H), 3.35 (m, 1H), 3.25 (m, 2H), 2.95 (m, 1H), 1.95 (m, 1H), 1.85 (m, 1H), 1.80 (m, 1H), 1.70 (m, 1H), 1.55 (m, 1H), 1.40 (m, 1H), 1.25 (m, 1H), 0.90 (s, 3H).

The following examples 14 and 15 were prepared analogously to example 3.

Example 14

8-Methyl-8-phenyl-2,3,4,6,7,8-hexahydro-1H-[1,4]diazepino[6,7,1-ij]quinoline dihydrochloride (racemic mixture in form of the salt of the compound of the formula I.g, I.h or I.i in which the combination of $R^{5a}$, $R^{5b}$, $R^7$, $R^8$ and $R^{9a}$ is as in row B-161 of Table B)

ESI-MS: m/z (%): 279 (100, [M+H]$^+$)

$^1$H-NMR (500 MHz, CDCl$_3$): δ=7.22-7.27 (m, 2H), 7.11-7.19 (m, 3H), 6.95-7.04 (m, 2H), 6.78 (dd, J=8.0, 7.5 Hz, 1H), 3.99 (d, J=14.4 Hz, 1H), 3.87 99 (d, J=14.5 Hz, 1H), 3.20-3.26 (m, 1H), 3.01-3.08 (m, 4H), 2.87-2.94 (m, 1H), 2.09-2.15 (m, 1H), 1.92-1.99 (m, 1H), 1.73 (s, 3H) ppm.

Example 15

8-Methyl-8-phenyl-2,3,4,6,7,8-hexahydro-1H-[1,4]diazepino[6,7,1-ij]quinoline, bis hydrochloride (racemic mixture of compound of the formula I.g, I.h or I.i in which the combination of $R^{5a}$, $R^{5b}$, $R^7$, $R^8$ and $R^{9a}$ is as in row B-161 of Table B)

ESI-MS: m/z (%): 279 (100, [M+H]$^+$).

$^1$H NMR (CDCl$_3$, 500 MHz): [ppm]: 7.25 (m, 2H), 7.15 (m, 3H), 7.05 (d, 1H), 6.95 (d, 1H), 6.80 (m, 1H), 4.00 (m, 1H), 3.90 (m, 1H), 3.25 (m, 1H), 3.05 (m, 4H), 2.90 (m, 1H), 2.10 (m, 1H), 1.95 (m, 1H), 1.75 (s, 3H).

Example 16

(R)-5,6,7,9,9a,10,11,12-Octahydro-4H-[1,4]diazepino[1,7,6-de]pyrrolo[1,2-a]quinoxaline bis(2,2,2-trifluoroacetate) (R-enantiomer of the compound of the formula I.a, I.b or I.c in which the combination of $R^{5a}$, $R^{5b}$, $R^7$, $R^8$ and $R^{9a}$ is as in row A-121 of Table A)

16.1 Preparation of (R)-tert-butyl 9-oxo-6,7,9a,10,11,12-hexahydro-4H-[1,4]diazepino[1,7,6-de]pyrrolo[1,2-a]quinoxaline-5(9H)-carboxylate 65 mg of (R)-tert-butyl 9-chloro-1-(pyrrolidine-2-carbonyl)-2,3-dihydro-1H-benzo[e][1,4]diazepine-4(5H)-carboxylate was stirred together with 1.8 mg of 2'-(ditert-butylphosphino)-N,N-dimethylbiphenyl-2-amine, 2.5 mg Pd$_2$(dba)$_3$ and 19 mg sodium 2-methylpropan-2-olate at 100° C. over 10 hours in toluene. The reaction mixture was then cooled to room temperature and evaporated. The residue was purified by column chromatography on silica (eluent: 10-25% ethyl acetate in heptane) to yield 20 mg of the title compound as a beige solid.

ESI-MS: m/z (%): 288 (80, [M-C$_4$H$_9$+2H]$^+$, 344 (20, [M+H]$^+$).

16.2 Preparation of (R)-tert-butyl 6,7,9a,10,11,12-hexahydro-4H-[1,4]diazepino[1,7,6-de]pyrrolo[1,2-a]quinoxaline-5(9H)-carboxylate (R-enantiomer of the compound of the formula I.a, I.b or I.c in which the combination of $R^{5a}$, $R^{5b}$, $R^7$, $R^8$ and $R^{9a}$ is as in row A-121 of Table A, wherein however $R^1$ is not H, but Boc)

Reduction of the compound obtained in step 16.1 analogously to example 1.3 yielded the title compound.

16.3 Preparation of (R)-5,6,7,9,9a,10,11,12-octahydro-4H-[1,4]diazepino[1,7,6-de]pyrrolo[1,2-a]quinoxaline bis(2,2,2-trifluoroacetate) (R-enantiomer of the compound of the formula I.a, I.b or I.c in which the combination of $R^{5a}$, $R^{5b}$, $R^7$, $R^8$ and $R^{9a}$ is as in row A-121 of Table A)

Boc-deprotection of the compound obtained in step 2.1 analogously to example 1.4 yielded the title compound.
ESI-MS: m/z (%): 230 (100, [M+H]$^+$).
Example 17 was prepared analogously to example 16 employing (S)-tert-butyl 9-chloro-1-(pyrrolidine-2-carbonyl)-2,3-dihydro-1H-benzo[e][1,4]diazepine-4(5H)-carboxylate as starting material which was derived from (R)-1-(((9H-fluoren-9-yl)methoxy)carbonyl)pyrrolidine-2-carboxylic acid.

Example 17

(S)-5,6,7,9,9a,10,11,12-Octahydro-4H-[1,4]diazepino[1,7,6-de]pyrrolo[1,2-a]quinoxaline bis(2,2,2-trifluoroacetate) (S-enantiomer of the compound of the formula I.a, I.b or I.c in which the combination of $R^{5a}$, $R^{5b}$, $R^7$, $R^8$ and $R^{9a}$ is as in row A-121 of Table A)
ESI-MS: m/z (%): 230 (100, [M+H]$^+$).
The following examples 18 to 23 were prepared analogously to example 1.

Example 18

9-Chloro-8,8-dimethyl-2,3,4,6,7,8-hexahydro-1H-[1,4]diazepino[6,7,1-ij]quinoline bis(2,2,2-trifluoroacetate) (compound of the formula I.g in which the combination of $R^{5a}$, $R^{5b}$, $R^7$, $R^8$ and $R^{9a}$ is as in row B-3 of Table B)
ESI-MS: m/z (%): 251 (100, [M+H]$^+$).

Example 19

10-Chloro-8,8-dimethyl-2,3,4,6,7,8-hexahydro-1H-[1,4]diazepino[6,7,1-ij]quinoline bis(2,2,2-trifluoroacetate) (compound of the formula I.h in which the combination of $R^{5a}$, $R^{5b}$, $R^7$, $R^8$ and $R^{9a}$ is as in row B-3 of Table B)
ESI-MS: m/z (%): 251 (100, [M+H]$^+$).

Example 20

9-Chloro-8,8-dimethyl-3,4,7,8-tetrahydro-1H-[1,4]diazepino[6,7,1-ij]quinolin-6(2H)-one 2,2,2-trifluoroacetate (compound of the formula I.j in which the combination of $R^{5a}$, $R^{5b}$, $R^7$, $R^8$ and $R^{9a}$ is as in row B-3 of Table B)
ESI-MS: m/z (%): 265 (100, [M+H]$^+$).

Example 21

10-Chloro-8,8-dimethyl-3,4,7,8-tetrahydro-1H-[1,4]diazepino[6,7,1-ij]quinolin-6(2H)-one 2,2,2-trifluoroacetate (compound of the formula I.k in which the combination of $R^{5a}$, $R^{5b}$, $R^7$, $R^8$ and $R^{9a}$ is as in row B-3 of Table B)
ESI-MS: m/z (%): 265 (100, [M+H]$^+$).

Example 22

9-Fluoro-8,8-dimethyl-2,3,4,6,7,8-hexahydro-1H-[1,4]diazepino[6,7,1-ij]quinoline (compound of the formula I.g in which the combination of $R^{5a}$, $R^{5b}$, $R^7$, $R^8$ and $R^{9a}$ is as in row B-2 of Table B)
ESI-MS: m/z (%): 235 (100, [M+H]$^+$).

Example 23

10-Fluoro-8,8-dimethyl-2,3,4,6,7,8-hexahydro-1H-[1,4]diazepino[6,7,1-ij]quinoline bis(2,2,2-trifluoroacetate) (compound of the formula I.h in which the combination of $R^{5a}$, $R^{5b}$, $R^7$, $R^8$ and $R^{9a}$ is as in row B-2 of Table B)
ESI-MS: m/z (%): 235 (100, [M+H]$^+$).
The following examples 24 to 26 were prepared analogously to example 2.

Example 24

1,2,3,4,6,7-Hexahydrospiro[[1,4]diazepino[6,7,1-ij]quinoline-8,1'-cyclohexane](2,2,2-trifluoroacetate) (compound of the formula I.g, I.h or I.i in which the combination of $R^{5a}$, $R^{5b}$, $R^7$, $R^8$ and $R^{9a}$ is as in row B-321 of Table B)
ESI-MS: m/z (%): 257.2 (100, [M+H]$^+$).
$^1$H NMR (CDCl$_3$, 500 MHz): [ppm]: 8.85 (bs, 2H), 7.45 (d, 1H), 7.15 (d, 1H), 6.90 (m, 1H), 4.15 (s, 2H), 3.25 (m, 4H), 3.15 (m, 2H), 1.80 (m, 2H), 1.70 (m, 4H), 1.55 (m, 4H), 1.30 (m, 2H).

Example 25

1',2',3',4',6',7'-Hexahydrospiro[cyclobutane-1,8'-[1,4]diazepino[6,7,1-ij]quinoline], hydrochloride (compound of the formula I.g, I.h or I.i in which the combination of $R^{5a}$, $R^{5b}$, $R^7$, $R^8$ and $R^{9a}$ is as in row B-241 of Table B)
ESI-MS [M+H+]=229.20
$^1$H NMR (CDCl$_3$, 500 MHz): [ppm]: 8.80 (bs, 2H), 7.50 (d, 1H), 6.95 (d, 1H), 6.90 (m, 1H), 4.10 (s, 2H), 3.25 (m, 2H), 3.20 (m, 2H), 3.10 (m, 2H), 2.35 (m, 2H), 2.00 (m, 2H), 1.90 (m, 4H).

Example 26

9'-Fluoro-1',2',3',4',6',7'-hexahydrospiro[cyclobutane-1,8'-[1,4]diazepino[6,7,1-ij]quinoline], hydrochloride (compound of the formula I.g in which the combination of $R^{5a}$, $R^{5b}$, $R^7$, $R^8$ and $R^{9a}$ is as in row B-242 of Table B)
ESI-MS [M+H+]=247.15
$^1$H NMR (DMSO-d$_6$, 500 MHz): [ppm]: 9.00 (bs, 2H), 7.25 (m, 1H), 6.80 (m, 1H), 4.10 (s, 2H), 3.25 (m, 2H), 3.20 (m, 2H), 3.10 (m, 2H), 2.65 (m, 2H), 2.00 (m, 4H), 1.85 (m, 2H).
The following examples 27 and 28 were prepared analogously to example 1.

Example 27

Enantiomer of 7,8,8-trimethyl-1,2,3,4,7,8-hexahydro-6H-[1,4]diazepino[6,7,1-ij]quinoline (enantiomer of the compound of the formula I.g, I.h or I.i in which the combination of $R^{5a}$, $R^{5b}$, $R^7$, $R^8$ and $R^{9a}$ is as in row B-25 of Table B)
ESI-MS [M+H+]=231.20
$^1$H NMR (CDCl$_3$, 500 MHz): [ppm]: 7.25 (d, 1H), 7.00 (d, 1H), 6.85 (dd, 2H), 4.00 (m, 1H), 3.90 (m, 1H), 3.15 (m, 4H), 3.05 (m, 2H), 1.85 (m, 1H), 1.30 (s, 3H), 1.10 (s, 3H), 0.95 (d, 3H).

The retention time of the Boc-protected precursor according to method B is 10.363.

Example 28

Enantiomer of 7,8,8-trimethyl-1,2,3,4,7,8-hexahydro-6H-[1,4]diazepino[6,7,1-ij]quinoline]

(enantiomer of the compound of the formula I.g, I.h or I.i in which the combination of $R^{5a}$, $R^{5b}$, $R^7$, $R^8$ and $R^{9a}$ is as in row B-25 of Table B)
ESI-MS [M+H+]=231.20
$^1$H NMR (CDCl$_3$, 500 MHz): [ppm]: 7.25 (d, 1H), 7.00 (d, 1H), 6.85 (dd, 2H), 4.00 (m, 1H), 3.90 (m, 1H), 3.15 (m, 4H), 3.05 (m, 2H), 1.85 (m, 1H), 1.30 (s, 3H), 1.10 (s, 3H), 0.95 (d, 3H).

The retention time of the Boc-protected precursor according to method B is 11.410 min.
The following example 29 was prepared analogously to example 2.

Example 29

3-Methyl-1',2',3',4',6',7'-hexahydrospiro[cyclobutane-1,8'-[1,4]diazepino[6,7,1-ij]quinoline], hydrochloride (compound of the formula I.p, I.q or I.r in which the combination of $R^{5a}$, $R^{5b}$, $R^7$, $R^8$ and $R^{9a}$ is as in row B-241 of Table B)
ESI-MS [M+H+]=243.20
$^1$H NMR (DMSO-d$_6$, 500 MHz): [ppm]: 9.30 (bs, 2H), 8.55 (bs, 1H), 7.60 (d, 1H), 7.20 (d, 1H), 6.95 (dd, 1H), 4.20 (m, 1H), 4.05 (m, 1H), 3.35 (m, 1H), 3.20 (m, 2H), 2.90 (m, 1H), 2.40 (m, 1H), 2.25 (m, 1H), 2.05 (m, 1H), 1.95 (m, 6H), 1.2 (d, 3H).

Example 30

3-Benzyl-2',3',7',8',9',10'-hexahydro-1H-3',8',10a'-triaza-cyclohepta[de]naphthalene (compound of the formula I.a, I.b or I.c in which the combination of $R^{5a}$, $R^{5b}$, $R^7$, $R^8$ and $R^{9a}$ is as in row A-121 of Table A)

30.1 Preparation of 2-(4-benzyl-3,4-dihydro-2H-quinoxalin-1-yl)-acetamide

A solution of 1 g (4.46 mmol) 1-benzyl-1,2,3,4-tetrahydroquinoxaline in 10 ml of dimethylformamide was treated with 3.14 ml (18.15 mmol) of N-Ethyl-N-isopropylpropan-2-amine, and subsequently 863 mg (9.23 mmol) 2-chloroacetamide was added. The reaction mixture was heated in a microwave system at 100° C. for four hours. The resulting mixture was quenched with water and extracted once with ethylacetate. The aqueous phase was set to pH 10 with sodium hydroxide solution and extracted 3× with ethylacetate. The combined organic extracts were dried with magnesium sulfate, evaporated till dryness and directly purified by column chromatography on silica (eluent: starting with heptane and then up to 100% ethylacetate) to yield 1.224 g of the title compound.
ESI-MS: m/z (%): 282.10 (100, [M+H]+).

30.2 Preparation of 2-(4-Benzyl-3,4-dihydro-2H-quinoxalin-1-yl)-ethylamine

To 1.224 g (4.35 mmol) of 2-(4-benzyl-3,4-dihydro-2H-quinoxalin-1-yl)-acetamide were added 10.88 ml (21.75 mmol) borane dimethylsulfide THF solution and subsequently heated to 60° C. for six hours in a microwave system. The mixture was quenched with 1 molar hydrochloric acid and methanol and heated for 15 minutes at 60° C. in a microwave system. The reaction mixture was diluted with ethylacetate and extracted 3× with 1 molar hydrochlorid acid. The combined aqueous phases were set to pH 10 with sodium hydroxide solution and extracted 3× with dichloromethane. The combined organic phases were dried and evaporated to yield 1.089 g of the title compound as an oil.
ESI-MS: m/z (%): 268.15 (100, [M+H]+).

30.3 Preparation of 3-benzyl-2,3,7,8,9,10-hexahydro-1H-3,8,10a-triaza-cyclohepta[de]-naphthalene A solution of 1.089 g (4.07 mmol) of 2-(4-benzyl-3,4-dihydro-2H-quinoxalin-1-yl)ethylamine and 20 ml ethanol was treated with 122 mg (4.07 mmol) of formaldehyde and 511 mg (4.48 mmol) of trifluoroacetic acid and stirred over night at room temperature. The solvent was evaporated and dichloromethane was added to the crude mixture. The organic phase was washed with 1 molar sodium hydroxide solution. The organic phase was dried and purified by column chromatography on silica (eluent: starting with dichloromethane and then up to 100% methanol) to yield 448 mg of the title compound.
ESI-MS [M+H+]=280.10 (100, [M+H]+).
$^1$H NMR (CDCl$_3$, 500 MHz): [ppm]: 7.35 (m, 3H), 7.30 (m, 2H), 6.80 (dd, 1H), 6.65 (d, 1H), 6.60 (d, 1H), 4.55 (s, 2H), 4.10 (s, 2H), 3.30 (m, 4H), 3.25 (m, 2H), 3.10 (m, 2H).

Example 31

9-Fluoro-1-methyl-1,2,3,4,6,7-hexahydrospiro[[1,4]diazepino[6,7,1-ij]quinoline-8,1'-cyclobutane], trifluoroacetic acid salt (compound of the formula I.m in which the combination of $R^{5a}$, $R^{5b}$, $R^7$, $R^8$ and $R^{9a}$ is as in row B-242 of Table B)

31.1 Preparation of 2-cyclobutylidene-N-(3-fluorophenyl)-acetamide 1.5 g (13.50 mmol) of 3-fluoroaniline were dissolved in 20 ml of dichloromethane and treated with 5.19 g (29.7 mmol) of N-ethyl-N-isopropylpropan-2-amine. Within 10 min 12.82 g (16.20 mmol) of 2-cyclobutylideneacetyl chloride were added at 0° C. and the solution was stirred overnight at room temperature. The mixture was poured on ice water and extracted 2× with dichloromethane. The combined organic phases were washed once with saturated sodium chloride solution, dried with MgSO$_4$ and evaporated in vacuo. The crude oil was treated with heptane and decanted twice, redissolved in ether-dichloromethane and treated with heptane till crystallization, yielding 2.2 g (77%) of a beige solid.
ESI-MS: m/z (%): 206 (100, [M+H]+).

31.2 Preparation of 5'-fluoro-1'H-spiro[cyclobutane-1,4'-quinolin]-2'(3'H)-one A solution of 400 mg (1.94 mmol) of 2-cyclobutylidene-N-(3-fluorophenyl)-acetamide obtained in step 31.1 was dissolved in 19.5 ml of toluene and irradiated with a Hg middle pressure lamp in a suitable device till completion of the reaction indicated by liquid chromatography. The crude solution was concentrated in vacuo and the residue was purified by column chromatography on silica (eluent: 10-30% ethyl acetate in heptane) to yield 55 mg (14%) of the title compound as a beige solid.

ESI-MS: m/z (%): 206 (100, [M+H]+).

31.3 Preparation of 5'-fluoro-2',3'-dihydro-1'H-spiro[cyclobutane-1,4'-quinoline]

A solution of 50 mg (0.244 mmol) of 5'-fluoro-1'H-spiro[cyclobutane-1,4'-quinolin]-2'(3'H)-one obtained in step 31.2 in 1 mL of tetrahydrofuran was treated with 0.73 mL of 1 M solution of borohydride-tetrahydrofuran complex in tetrahydrofuran. The mixture was stirred at reflux for 2 h, quenched with water and evaporated till dryness. The crude compound was used in the subsequent step without purification.

ESI-MS: m/z (%): 192 (100, [M+H]+).

31.4 Preparation of 2-(5'-fluoro-2',3'-dihydro-1'H-spiro[cyclobutane-1,4'-quinolin]-1'-yl)-acetamide A solution of 50 mg (0.26 mmol) of 5'-fluoro-2',3'-dihydro-1'H-spiro[cyclobutane-1,4'-quinoline]obtained in step 31.3 in 1 ml of dimethylformamide was treated with 6.2 mg (0.26 mmol) of sodium hydride followed by 72 mg (0.52 mmol) 2-bromoacetamide and heated in a microwave system at 10° C. for one hour. The resulting mixture was quenched with water, evaporated till dryness and directly purified by column chromatography on silica (eluent: 10% methanol in dichloromethane) to yield 70 mg of the title compound with about 80% purity determined by LCMS.

ESI-MS: m/z (%): 249 (100, [M+H]+).

31.5 Preparation of 2-(5'-fluoro-2',3'-dihydro-1'H-spiro[cyclobutane-1,4'-quinolin]-1'-yl)ethanamine A solution of 40 mg (0.16 mmol) of 2-(5'-fluoro-2',3'-dihydro-1'H-spiro[cyclobutane-1,4'-quinolin]-1'-yl)-acetamide obtained in step 31.4 in 1 ml of tetrahydrofurane was treated with 38 µl (0.40 mmol) of borane dimethylsulfide and heated to 70° C. for two hours. The mixture was quenched with water and hydrochloric acid, diluted with dichloromethane and extracted twice with water. The combined aqueous phases were set to pH 10 with sodium hydroxide solution and extracted 3× with dichloromethane. The combined organic phases were dried and evaporated to yield 10 mg of the title compound as an oil.

ESI-MS: m/z (%): 235 (100, [M+H]+).

31.6 Preparation of 9-fluoro-1-methyl-1,2,3,4,6,7-hexahydrospiro[[1,4]diazepino[6,7,1-ij]quinoline-8,1'-cyclobutane], trifluoroacetic acid salt A solution of 10 mg (0.043 mmol) of 2-(5'-fluoro-2',3'-dihydro-1'H-spiro[cyclobutane-1,4'-quinolin]-1'-yl)ethanamine obtained in step 31.5 in 0.4 ml of acetonitrile/methanol was treated with 3.8 mg (0.085 mmol) of acetaldehyde and 6.5 µl (0.085 mmol) of trifluoroacetic acid and stirred over night at room temperature. The solvent was evaporated and the crude mixture purified with reversed phase liquid chromatography to yield 1.5 mg of the title compound as beige solid.

ESI-MS: m/z (%): 261 (100, [M+H]+).
$^1$H-NMR (500 MHz, pyridine-d$_5$): δ=7.06 (dd, J=8.3, 6.4 Hz, 1H), 6.79 (dd, J=11.8, 8.4 Hz, 1H), 4.18 (q, J=6.9, 13.8 Hz, 1H), 3.10-3.00 (m, 2H), 2.99-2.95 (m, 2H), 2.85-2.80 (m, 2H), 2.79-2.70 (m, 2H), 2.09-1.97 (m, 2H), 1.90-1.70 (m, 4H), 1.51 (d, J=6.9, 3H) ppm.

II. Biological Tests

Functional Activity

The functional activity of compounds of formula I was assayed by incubation with U2OS_HTR$_{2C}$ β-Arrestin cells (DiscoverX, 93-0289C3) to induce beta-arrestin2 recruitment to the 5-HT$_{2C}$ receptor. The agonist-induced recruitment and proximity of the receptor and beta-arrestin2 leads to complementation and formation of active β-galactosidase. The enzyme complementation results in enzyme activity, which is measured following the termination of the agonist incubation using DiscoveRx's detection reagent, which contains a chemiluminescent substrate which produces a high intensity signal. Cells were plated and a medium-change to a 1% serum containing medium was performed 24 h later. The next day, test compounds were added and incubated for 1.5 h before addition of detection reagent.

The response produced was measured and compared with the response produced by 10 [mu]M 5-HT or the maximal effect induced by 5-HT (defined as 100%) to which it was expressed as a percentage response (relative efficacy). Dose response curves were constructed using Graphpad Prism (Graph Software Inc.) or using in house adapted software using a 4 parameter dose response model with variable slope (fit=(Bottom+(Top−Bottom)/(1+10^((LogEC50−x)*HillSlope))res=(y−fit)). Results are compiled in the table below.

TABLE

| # | Potency (EC50) in functional assay | % efficacy |
|---|---|---|
| 1 | ++ | 71 |
| 6 | ++ | 63 |
| 8 | ++ | 40 |
| 9 | +++ | 61 |
| 16 | + | 55 |
| 17 | ++ | 84 |
| 19 | ++ | 25 |
| 22 | ++ | 69 |
| 25 | ++ | 90 |
| 26 | +++ | 107 |
| 27 | + | 87 |
| 28 | ++ | 55 |

Potency (EC50):
+ from 200 nM to <1 µM
++ from 20 nM to <200 nM
+++ <20 nM

We claim:
1. A compound of the formula I

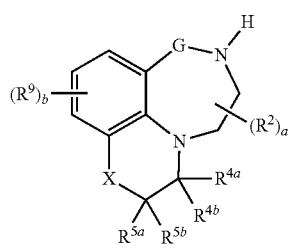

wherein
G is $(CR^{3a}R^{3b})_n$;
X is $CR^7R^8$;
R$^1$ is selected from the group consisting of hydrogen, cyano, C$_1$-C$_6$-alkyl, fluorinated C$_1$-C$_6$-alkyl, C$_2$-C$_6$-alkenyl, fluorinated C$_2$-C$_6$-alkenyl, C$_2$-C$_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, —C(=O)$R^{10}$, phenyl, phenyl-$C_1$-$C_2$-alkyl and a 3-, 4-, 5-, 6-, 7- or 8-membered saturated, partially unsaturated or maximally unsaturated heterocyclic ring containing 1, 2, 3 or 4 heteroatoms or heteroatom groups independently selected from N, O, S, NO, SO and $SO_2$ and optionally also 1 or 2 C=O and/or C=S groups as ring members, where the cyclic moieties in the three last-mentioned radicals may be substituted with one or more substituents $R^{11}$;

each $R^2$ is independently selected from the group consisting of cyano, nitro, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, —$NR^{12a}R^{12b}$, —$CH_2NR^{12a}R^{12b}$, —$NR^{12a}C(O)R^{10}$, —C(=O)$R^{10}$, $SO_2NR^{12a}R^{12b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{11}$;

$R^{3a}$ and $R^{3b}$, independently of each other, are selected from the group consisting of hydrogen, cyano, nitro, $C_1$-$C_6$-alkyl, fluorinated $C_1$-$C_6$-alkyl, $C_1$-$C_6$-alkoxy, and fluorinated $C_1$-$C_6$-alkoxy;

$R^{4a}$ and $R^{4b}$, independently of each other, are selected from the group consisting of hydrogen, cyano, nitro, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl,
—$NR^{12a}R^{12b}$, —$CH_2NR^{12a}R^{12b}$, —$NR^{12a}C(O)R^{10}$, —C(=O)$R^{10}$, $SO_2NR^{12a}R^{12b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{11}$; or $R^{4a}$ and $R^{4b}$ form together a group =O or =S;

$R^{5a}$ and $R^{5b}$, independently of each other, are selected from the group consisting of hydrogen, deuterium, halogen, cyano, nitro, hydroxy, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, —$NR^{12a}R^{12b}$, —$CH_2NR^{12a}R^{12b}$—$NR^{12a}C(O)R^{10}$, —C(=O)$R^{10}$, $SO_2NR^{12a}R^{12b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{11}$;

$R^7$ and $R^8$, independently of each other, are selected from the group consisting of deuterium, halogen, cyano, nitro, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl,
—$NR^{12a}R^{12b}$, —$CH_2NR^{12a}R^{12b}$, —$NR^{12a}C(O)R^{10}$, —C(=O)$R^{10}$, $SO_2NR^{12a}R^{12b}$, $C_1$-$C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N, O, S, NO, SO, $SO_2$, C=O and C=S as ring members, where the cyclic moieties in the six last-mentioned radicals may be substituted with one or more substituents $R^{11}$; or $R^7$ and $R^8$, together with the carbon atom they are bound to, form a 3-, 4-, 5-, 6-, 7-, or 8-membered saturated, partially unsaturated or maximally unsaturated carbocyclic ring, wherein the ring may be substituted with one or more substituents $R^{11}$;

each $R^9$ is independently selected from the group consisting of halogen, cyano, nitro, hydroxy, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_3$-$C_8$-cycloalkenyl, fluorinated $C_3$-$C_8$-cycloalkenyl, $C_1$-$C_6$-alkoxy, fluorinated $C_1$-$C_6$-alkoxy, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, —$NR^{12a}R^{12b}$, —$CH_2NR^{12a}R^{12b}$, —$NR^{12a}C(O)R^{10}$, —C(=O)$R^{10}$, $SO_2NR^{12a}R^{12b}$, $C_1C_6$-alkylcarbonyloxy, fluorinated $C_1$-$C_6$-alkylcarbonyloxy, phenyl, phenyl-$C_1$-$C_2$-alkyl, phenoxy, phenylsulfonyl, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N,O,S, NO, SO, $SO_2$, C=O and C=S as ring members, where the cyclic moieties in the six last-mentioned radicals may be substituted with one or more substituents $R^{11}$;

each $R^{10}$ is independently selected from the group consisting of hydrogen, cyano, hydroxy, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, —$NR^{12a}R^{12b}$, —$CH_2NR^{12a}R^{12b}$, phenyl, phenyl-$C_1$-$C_2$-alkyl, phenoxy, benzyloxy and a 3-, 4-, 5-, 6-, 7- or 8-membered saturated, partially unsaturated or maximally unsaturated ring containing 1, 2, 3 or 4 heteroatoms or heteroatom groups independently selected from N,O,S, NO, SO, $SO_2$, C=and C=S as ring members, where the cyclic moieties in the five last-mentioned radicals may be substituted with one or more substituents $R^{11}$;

each $R^{11}$ is independently selected from the group consisting of halogen, cyano, nitro, hydroxy, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkoxy -$C_1$-$C_4$-alkyl, $C_1$-$C_6$-hydroxyalkoxy, $C_1$-$C_6$-alkoxy-$C_1$-$C_4$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, —COOH, —$NR^{12a}R^{12b}$, $C_1$-$C_6$-alkylcarbonyl, fluorinated $C_1$-$C_6$-alkylcarbonyl, $C_1$-$C_6$-alkoxycarbonyl, fluorinated $C_1$-$C_6$-alkoxycarbonyl, $SO_2NR^{12a}R^{12b}$, $C_1$-$C_6$-alkylcarbonyloxy and fluorinated $C_1$-$C_6$-alkylcarbonyloxy;

$R^{12a}$ and $R^{12b}$, independently of each other and independently of each occurrence, are selected from the group consisting of hydrogen, cyano, $C_1$-$C_6$-alkyl, fluorinated $C_1$-$C_6$-alkyl, $C_2$-$C_6$-alkenyl, fluorinated $C_2$-$C_6$-alkenyl, $C_2$-$C_6$-alkynyl, fluorinated $C_2$-$C_6$-alkynyl, $C_3$-$C_8$-cycloalkyl, fluorinated $C_3$-$C_8$-cycloalkyl, $C_1$-$C_6$-alkoxy, fluorinated $C_1$-$C_6$-alkoxy, $C_1$-$C_6$-alkylcarbonyl, fluorinated $C_1$-$C_6$-alkylcarbonyl, $C_1$-$C_6$-alkoxycarbonyl, fluorinated $C_1$-$C_6$-alkoxycarbonyl, phenyl and benzyl, where the phenyl moieties in the two last-mentioned radicals may carry 1, 2 or 3 substituents selected from halogen, cyano, nitro, $C_1$-$C_6$-alkyl, fluorinated $C_1$-$C_6$-alkyl, $C_1$-$C_6$-alkoxy and fluorinated $C_1$-$C_6$-alkoxy; or, if $R^{12a}$ and $R^{12b}$ are bound to the same nitrogen atom, together with this nitrogen atom may form a 3-, 4-, 5-, 6-, 7- or 8-membered saturated, partially unsaturated or maximally unsaturated heterocyclic ring, where the ring may further contain 1, 2, 3 or 4 heteroatoms or heteroatom-containing groups selected from O,S,N, SO, $SO_2$, C=O and C=S as ring members, and where the ring may be substituted with one or more substituents selected from halogen, cyano, nitro, $C_1$-$C_6$-alkyl, fluorinated $C_1$-$C_6$-alkyl, $C_1$-$C_6$-alkoxy and fluorinated $C_1$-$C_6$-alkoxy;

a is 0, 1 or 2;
b is 0, 1, 2 or 3; and
n is 1;
or the N-oxides, tautomeric forms, stereoisomers or pharmaceutically acceptable salts thereof, or the compound of the general formula I, wherein at least one of the atoms has been replaced by its stable, non-radioactive isotope.

2. The compound as claimed in claim 1, wherein at least one hydrogen atom has been replaced by a deuterium atom.

3. The compound as claimed in claim 1, where $R^1$ is selected from hydrogen and $C_1$-$C_6$-alkyl.

4. The compound as claimed in claim 1, where $R^2$ is selected from cyano, nitro, $C_1$-$C_6$alkyl, fluorinated $C_1$-$C_6$-alkyl, $C_1$-$C_6$-alkoxy and fluorinated $C_1$-$C_c$alkoxy.

5. The compound as claimed in claim 1, where $R^{3a}$ is selected from hydrogen, cyano, nitro, $C_1$-$C_6$-alkyl, fluorinated $C_1$-$C_6$-alkyl, $C_1$-$C_6$-alkoxy and fluorinated $C_1$-$C_6$-alkoxy, and $R^{3b}$ is hydrogen.

6. The compound as claimed in claim 5, where $R^{3a}$ is selected from hydrogen and methyl, and $R^{3b}$ is hydrogen.

7. The compound as claimed in claim 6, where $R^{3a}$ and $R^{3b}$ are hydrogen.

8. The compound as claimed in claim 1, where $R^{4a}$ and $R^{4b}$, independently of each other, are selected from hydrogen, $C_1$-$C_6$-alkyl and fluorinated $C_1$-$C_6$-alkyl or form together a group =O.

9. The compound as claimed in claim 1, where
$R^{5a}$ is selected from hydrogen, cyano, nitro, hydroxy, $C_1C_6$-alkyl, fluorinated $C_1$-$C_6$-alkyl, $C_1$-$C_6$-alkoxy, halogen and fluorinated $C_1$-$C_6$-alkoxy; and
$R^{5b}$ is selected from hydrogen and deuterium.

10. The compound as claimed in claim 9, where
$R^{5a}$ is selected from hydrogen, $C_1$-$C_6$-alkyl and fluorinated $C_1$-$C_6$-alkyl; and in case that X is $CR^7R^8$ is further selected from halogen; and
$R^{5b}$ is selected from hydrogen and deuterium.

11. The compound as claimed in claim 1, where $R^7$ and $R^8$, together with the carbon atom they are bound to, form a 4-, 5- or 6-membered saturated or partially unsaturated carbocyclic ring, where the ring may be substituted with one or more substituents $R^{11}$.

12. The compound as claimed in claim 1, where each $R^9$ is independently selected from halogen, cyano, nitro, hydroxy, $C_1$-$C_6$-alkyl, fluorinated $C_1$-$C_6$-alkyl, $C_3$-$C_6$-cycloalkyl, fluorinated $C_3$-$C_6$-cycloalkyl, $C_1$-$C_6$-alkoxy, fluorinated $C_1$-$C_6$-alkoxy and a 3-, 4-, 5- or 6-membered saturated heterocyclic ring containing 1 or 2 heteroatoms or heteroatom groups independently selected from N,O,S, NO, SO and $SO_2$ as ring members, where the heterocyclic ring may be substituted with one or more substituents $R^{11}$.

13. The compound as claimed in claim 1, where each $R^{11}$ is independently selected from halogen, cyano, nitro, hydroxy, $C_1$-$C_6$-alkyl, fluorinated $C_1$-$C_6$-alkyl, $C_1$-$C_6$-alkoxy and fluorinated $C_1$-$C_6$-alkoxy.

14. The compound as claimed in claim 1, where a is 0 or 1.
15. The compound as claimed in claim 1, where b is 0 or 1.
16. The compound as claimed in claim 1, of formula I.1

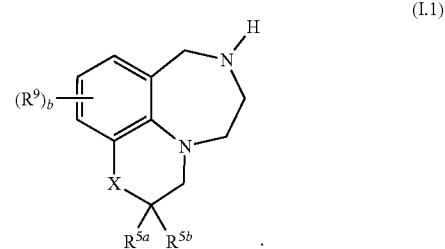

(I.1)

17. The compound as claimed in claim 16, of formula I.1.2

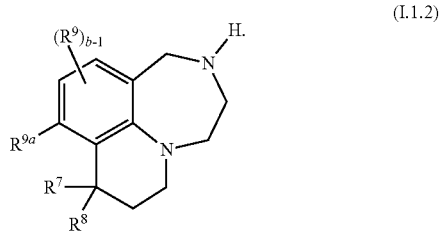

(I.1.2)

wherein
R⁷ is selected from C₁-C₄-alkyl and fluorinated C₁-C₄-alkyl;
R⁸ is selected from C₁-C₄-alkyl and fluorinated C₁C₄-alkyl; or
R⁷ and R⁸, together with the carbon atom they are bound to, form a 3-, 4-, 5-, 6- or 7-membered saturated or partially unsaturated carbocyclic ring, where the ring may be substituted with one or more substituents R¹¹; and
R⁹ᵃ is H or F.

18. The compound as claimed in claim 1, of formula I.2

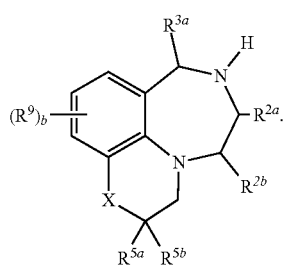

(I.2)

19. The compound as claimed in claim 18 of formula I.2.2

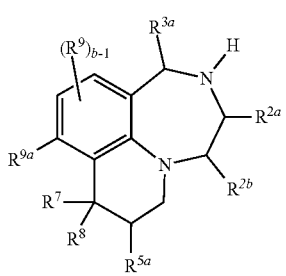

(I.2.2)

wherein
R²ᵃ, R²ᵇ, R³ᵃ and R⁵ᵃ, independently of each other, are selected from hydrogen and methyl;
R⁷ is selected from C₁-C₄-alkyl and fluorinated C₁-C₄-alkyl;
R⁸ is selected from C₁-C₄-alkyl and fluorinated C₁-C₄-alkyl; or
R⁷ and R⁸, together with the carbon atom they are bound to, form a 3-, 4-, 5-, 6- or 7-membered saturated or partially unsaturated carbocyclic ring, where the ring may be substituted with one or more substituents R¹¹; and
R⁹ᵃ is H or F.

20. The compound as claimed in claim 19, wherein R²ᵃ, R²ᵇ, R³ᵃ and R⁵ᵃ are selected from hydrogen and methyl, with the proviso that at most 2 of R²ᵃ, R²ᵇ, R³ᵃ and R⁵ᵃ are methyl.

21. The compound as claimed in claim 19, where R⁷ and R⁸, together with the carbon atom they are bound to, form a 4-, 5- or 6-membered saturated or partially unsaturated carbocyclic ring, where the ring may be substituted with one or more substituents R¹¹.

22. A compound of formula I as claimed in claim 1, selected from the group consisting of 8,8-dimethyl-2,3,4,6,7,8-hexahydro-1H-[1,4]diazepino[6,7,1-ij]quinoline;
1,2,3,4-tetrahydrospiro[[1,4]diazepino[6,7,1-ij]quinoline-8,1'-cyclopent[2]en]-6(7H)-one 2,2,2-trifluoroacetate;
8 -methyl-8 -phenyl-3,4,7,8 -tetrahydro-1H-[1,4]diazepino[6,7,1-ij]quinolin-6(2H)-one;
8,8-dimethyl-3,4,7,8-tetrahydro-1H-[1,4]diazepino[6,7,1-ij]quinolin-6(2H)-one;
1,2,3,4-tetrahydrospiro[[1,4]diazepino[6,7,1-ij]quinoline-8,1 '-cyclopentan]-6(7H)-one;
1,2,3,4,6,7-hexahydrospiro[[1,4]diazepino[6,7,1-ij]quinoline-8,1'-cyclopentane];
8-methyl-8-(trifluoromethyl)-2,3,4,6,7,8-hexahydro-1H-[1,4]diazepino[6,7,1-ij]quinolone;
8-methyl-8-(trifluoromethyl)-3,4,7,8-tetrahydro-1H- [1,4]diazepino[6,7,1-ij]quinolin-6(2H)-one;
8-methyl-8-phenyl-2,3,4,6,7,8-hexahydro-1H-[1,4]diazepino[6,7,1-ij]quinoline;
9-chloro-8,8-dimethyl-2,3,4,6,7,8-hexahydro-1H-[1,4]diazepino[6,7,1-ij]quinoline bis(2,2,2-trifluoroacetate);
10-chloro-8,8-dimethyl-2,3,4,6,7,8-hexahydro-1H-[1,4]diazepino[6,7,1-ij]quinoline bis (2,2,2-trifluoroacetate);
9-chloro-8,8-dimethyl-3,4,7,8-tetrahydro-1H-[1,4]diazepino[6,7,1-ij]quinolin-6(2H)-one 2,2,2-trifluoroacetate;
10-chloro-8,8-dimethyl-3,4,7,8-tetrahydro-1H-[1,4]diazepino[6,7,1-ij]quinolin-6(2H)-one 2,2,2-trifluoroacetate;
9-fluoro-8,8-dimethyl-2,3,4,6,7,8-hexahydro-1H-[1,4]diazepino[6,7,1-ij]quinoline;
10-fluoro-8,8-dimethyl-2,3,4,6,7,8-hexahydro-1H-[1,4]diazepino[6,7,1-ij]quinoline bis (2,2,2-trifluoroacetate);
1,2,3,4,6,7-hexahydrospiro[[1,4]diazepino[6,7,1-ij]quinoline-8,1'-cyclohexane] bis(2,2,2-trifluoroacetate);
1',2',3',4',6',7'-hexahydrospiro[cyclobutane-1,8'-[1,4]diazepino[6,7,1-ij]quinoline];
9'-fluoro-1',2',3',4',6',7'-hexahydrospiro [cyclobutane-1,8'-[1,4] diazepino [6,7,1-ij]quinoline];
7,8,8-trimethyl-1,2,3,4,7,8-hexahydro-6H-[1,4]diazepino [6,7,1-ij]quinoline;
9-fluoro-1 -methyl-1,2,3,4,6 ,7-hexahydrospiro [[1,4]diazepino [6,7,1 -ij]quinoline-8,1'-cyclobutane];and
3-methyl-1',2',3',4',6',7'-hexahydrospiro[cyclobutane-1, 8'-[1,4]diazepino[6,7,1-ij]quinoline];
or the stereoisomers or pharmaceutically acceptable salts thereof.

23. A pharmaceutical composition comprising a therapeutically effective amount of at least one compound as claimed in claim 1 or an N-oxide, a tautomeric form, a stereoisomer or a pharmaceutically acceptable salt thereof, or comprising at least one compound as defined in claim 1, wherein at least one of the atoms has been replaced by its stable, non-radioactive isotope, in combination with at least one pharmaceutically acceptable carrier and/or auxiliary substance.

* * * * *